(12) United States Patent
Pope et al.

(10) Patent No.: US 7,665,898 B2
(45) Date of Patent: *Feb. 23, 2010

(54) BEARINGS, RACES AND COMPONENTS THEREOF HAVING DIAMOND AND OTHER SUPERHARD SURFACES

(75) Inventors: Bill J. Pope, Springville, UT (US);
Jeffery K. Taylor, Loomis, CA (US);
Richard H. Dixon, Provo, UT (US);
Clayton F. Gardinier, American Fork, UT (US); Louis M. Pope, II, Provo, UT (US); Dean C. Blackburn, Springville, UT (US); Michael A. Vail, Genola, UT (US)

(73) Assignee: Diamicron, Inc., Orem, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/255,538

(22) Filed: Oct. 21, 2008

(65) Prior Publication Data

US 2009/0046967 A1 Feb. 19, 2009

Related U.S. Application Data

(63) Continuation of application No. 10/643,806, filed on Aug. 18, 2003, now Pat. No. 7,461,978, which is a continuation of application No. 09/840,634, filed on Apr. 22, 2001, now Pat. No. 6,655,845.

(51) Int. Cl.
*F16C 33/32* (2006.01)
(52) U.S. Cl. .................................. 384/492; 384/907.1
(58) Field of Classification Search ................. 384/492, 384/297, 303, 304
See application file for complete search history.

(56) References Cited

U.S. PATENT DOCUMENTS 2,947,608 A 8/1960 Hall (Continued)

FOREIGN PATENT DOCUMENTS

GB 2 283 772 5/1995

(Continued)

OTHER PUBLICATIONS

U.S. Appl. No. 11/435,383, filed May 16, 2006, Pope et al.

(Continued)

*Primary Examiner*—Thomas R Hannon
(74) *Attorney, Agent, or Firm*—Bateman IP Law Group

(57) ABSTRACT

Diamond bearings and bearing components are disclosed. Some embodiments of the bearings and bearing components include polycrystalline diamond compacts sintered under high pressure and high temperature to create a diamond table chemically and mechanically bonded to a substrate, the diamond table presenting a durable and thermally stable load bearing and articulation surface.

21 Claims, 30 Drawing Sheets

U.S. PATENT DOCUMENTS

| | | |
|---|---|---|
| 2,947,609 A | 8/1960 | Strong |
| 2,947,610 A | 8/1960 | Hall et al. |
| 2,947,611 A | 8/1960 | Bundy |
| 2,992,900 A | 7/1961 | Bovenkerk |
| 3,031,269 A | 4/1962 | Bovenkerk |
| 3,297,407 A | 1/1967 | Wentorf, Jr. |
| 3,423,177 A | 1/1969 | Bovenkerk |
| 3,488,153 A | 1/1970 | Bundy |
| 3,574,580 A | 4/1971 | Stromberg et al. |
| 3,597,158 A | 8/1971 | Horton |
| 3,702,573 A | 11/1972 | Nemeth |
| 3,819,814 A | 6/1974 | Pope |
| 3,864,409 A | 2/1975 | Pope |
| 3,865,585 A | 2/1975 | Rademacher |
| 4,012,229 A | 3/1977 | Herchenroeder et al. |
| 4,089,933 A | 5/1978 | Vereschagin et al. |
| 4,104,344 A | 8/1978 | Pope et al. |
| 4,104,441 A | 8/1978 | Fedoseev et al. |
| 4,163,769 A | 8/1979 | Pope et al. |
| 4,231,762 A | 11/1980 | Hara et al. |
| 4,259,072 A | 3/1981 | Hirabayashi et al. |
| 4,260,203 A | 4/1981 | Garner |
| 4,260,397 A | 4/1981 | Bovenkerk |
| 4,380,471 A | 4/1983 | Lee et al. |
| 4,410,054 A | 10/1983 | Nagel et al. |
| 4,454,612 A | 6/1984 | McDaniel et al. |
| 4,470,158 A | 9/1984 | Pappas et al. |
| 4,518,659 A | 5/1985 | Gigl et al. |
| 4,525,178 A | 6/1985 | Hall |
| 4,525,179 A | 6/1985 | Gigl |
| 4,604,106 A | 8/1986 | Hall |
| 4,610,699 A | 9/1986 | Yazu et al. |
| 4,662,348 A | 5/1987 | Hall et al. |
| 4,668,290 A | 5/1987 | Wang et al. |
| 4,714,468 A | 12/1987 | Wang et al. |
| 4,729,440 A | 3/1988 | Hall |
| 4,755,185 A | 7/1988 | Tarr |
| 4,778,486 A | 10/1988 | Csillag et al. |
| 4,802,539 A | 2/1989 | Hall |
| 4,808,185 A | 2/1989 | Penenberg et al. |
| 4,822,365 A | 4/1989 | Walker et al. |
| 4,822,366 A | 4/1989 | Bolesky |
| 4,865,603 A | 9/1989 | Noiles |
| 4,925,701 A | 5/1990 | Jansen et al. |
| 4,931,068 A | 6/1990 | Dismukes et al. |
| 4,979,957 A | 12/1990 | Hodorek |
| 5,002,577 A | 3/1991 | Bolesky et al. |
| 5,002,731 A | 3/1991 | Crook et al. |
| 5,009,673 A | 4/1991 | Cho |
| 5,011,515 A | 4/1991 | Frushour |
| 5,030,233 A | 7/1991 | Ducheyne |
| 5,037,423 A | 8/1991 | Kenna |
| 5,082,359 A | 1/1992 | Kirkpatrick |
| 5,092,687 A | 3/1992 | Hall |
| 5,108,432 A | 4/1992 | Gustavson |
| 5,128,146 A | 7/1992 | Hirayama et al. |
| 5,133,757 A | 7/1992 | Sioshansi et al. |
| 5,152,794 A | 10/1992 | Davidson |
| 5,152,795 A | 10/1992 | Sioshansi et al. |
| 5,154,023 A | 10/1992 | Sioshansi |
| 5,180,394 A | 1/1993 | Davidson |
| 5,181,926 A | 1/1993 | Koch et al. |
| 5,192,323 A | 3/1993 | Shetty et al. |
| 5,211,726 A | 5/1993 | Slutz et al. |
| 5,236,545 A | 8/1993 | Pryor |
| 5,248,317 A | 9/1993 | Tank et al. |
| 5,258,022 A | 11/1993 | Davidson |
| 5,284,394 A | 2/1994 | Lemelson |
| 5,308,412 A | 5/1994 | Shetty et al. |
| 5,310,408 A | 5/1994 | Schryver et al. |
| 5,322,735 A | 6/1994 | Fridez et al. |
| 5,330,481 A | 7/1994 | Hood et al. |
| 5,330,826 A | 7/1994 | Taylor et al. |
| 5,355,969 A | 10/1994 | Hardy et al. |
| 5,358,525 A | 10/1994 | Fox et al. |
| 5,370,694 A | 12/1994 | Davidson |
| 5,372,660 A | 12/1994 | Davidson et al. |
| 5,380,547 A | 1/1995 | Higgins |
| 5,383,934 A | 1/1995 | Armini et al. |
| 5,387,247 A | 2/1995 | Vallana et al. |
| 5,391,407 A | 2/1995 | Dearnaley |
| 5,391,408 A | 2/1995 | Piera |
| 5,391,409 A | 2/1995 | Shibata et al. |
| 5,391,422 A | 2/1995 | Omori et al. |
| 5,414,049 A | 5/1995 | Sun et al. |
| 5,415,704 A | 5/1995 | Davidson |
| 5,458,827 A | 10/1995 | Holly |
| 5,478,906 A | 12/1995 | Howard, Jr. |
| 5,480,683 A | 1/1996 | Chabrol et al. |
| 5,507,804 A | 4/1996 | Llanos |
| 5,507,814 A | 4/1996 | Gilbert et al. |
| 5,507,824 A | 4/1996 | Lennox |
| 5,508,368 A | 4/1996 | Knapp et al. |
| 5,512,235 A | 4/1996 | Cerutti et al. |
| 5,530,072 A | 6/1996 | Shirodkar |
| 5,554,415 A | 9/1996 | Turchan et al. |
| 5,560,716 A | 10/1996 | Tank et al. |
| 5,571,616 A | 11/1996 | Phillips et al. |
| 5,593,234 A | 1/1997 | Liston |
| 5,593,719 A | 1/1997 | Dearnaley et al. |
| 5,620,754 A | 4/1997 | Turchan et al. |
| 5,628,824 A | 5/1997 | Vohra et al. |
| 5,635,243 A | 6/1997 | Turchan et al. |
| 5,641,323 A | 6/1997 | Caldarise |
| 5,643,641 A | 7/1997 | Turchan et al. |
| 5,645,601 A | 7/1997 | Pope et al. |
| 5,702,448 A | 12/1997 | Buechel et al. |
| 5,725,573 A | 3/1998 | Dearnaley et al. |
| 5,766,394 A | 6/1998 | Anderson et al. |
| 5,773,140 A | 6/1998 | Cerutti et al. |
| 5,780,119 A | 7/1998 | Dearnaley et al. |
| 5,824,651 A | 10/1998 | Nanci et al. |
| 5,830,539 A | 11/1998 | Yan et al. |
| 5,855,996 A | 1/1999 | Corrigan et al. |
| 5,868,796 A | 2/1999 | Buechel et al. |
| 5,895,388 A | 4/1999 | Zobel |
| 5,916,269 A | 6/1999 | Serbousek et al. |
| 5,947,893 A | 9/1999 | Agrawal et al. |
| 5,981,827 A | 11/1999 | Devlin et al. |
| 6,010,533 A | 1/2000 | Pope et al. |
| 6,063,149 A | 5/2000 | Zimmer |
| 6,077,148 A | 6/2000 | Klein et al. |
| 6,183,818 B1 | 2/2001 | Vohra et al. |
| 6,207,218 B1 | 3/2001 | Layrolle et al. |
| 6,221,108 B1 | 4/2001 | Smith |
| 6,290,726 B1 | 9/2001 | Pope et al. |
| 6,340,245 B1 | 1/2002 | Horton et al. |
| 6,357,923 B1 | 3/2002 | Sato et al. |
| 6,398,815 B1 | 6/2002 | Pope et al. |
| 6,402,787 B1 | 6/2002 | Pope et al. |
| 6,410,877 B1 | 6/2002 | Dixon et al. |
| 6,425,922 B1 | 7/2002 | Pope et al. |
| 6,488,715 B1 | 12/2002 | Pope et al. |
| 6,494,918 B1 | 12/2002 | Pope et al. |
| 6,497,727 B1 | 12/2002 | Pope et al. |
| 6,514,289 B1 | 2/2003 | Pope et al. |
| 6,517,583 B1 | 2/2003 | Pope et al. |
| 6,596,225 B1 | 7/2003 | Pope et al. |
| 6,610,095 B1 | 8/2003 | Pope et al. |
| 6,655,845 B1 | 12/2003 | Pope et al. |
| 6,676,704 B1 | 1/2004 | Pope et al. |
| 6,709,463 B1 | 3/2004 | Pope et al. |
| 6,773,520 B1 | 8/2004 | Fehring et al. |
| 6,793,681 B1 | 9/2004 | Pope et al. |

| | | | | | | |
|---|---|---|---|---|---|---|
| 6,800,095 | B1 | 10/2004 | Pope et al. | GB | 2 290 327 | 12/1995 |
| 6,817,550 | B2 | 11/2004 | Taylor et al. | GB | 2 290 328 | 12/1995 |
| 7,077,867 | B1 | 7/2006 | Pope et al. | JP | 04 360077 | 12/1992 |
| 7,172,142 | B2 | 2/2007 | Taylor et al. | JP | 06 193637 | 7/1994 |
| 2003/0019106 | A1 | 1/2003 | Pope et al. | JP | 07 027138 | 1/1995 |
| 2003/0191533 | A1 | 10/2003 | Dixon et al. | JP | 07 127644 | 5/1995 |
| 2004/0111159 | A1 | 6/2004 | Pope et al. | JP | 07 282551 | 10/1995 |
| 2004/0199260 | A1 | 10/2004 | Pope et al. | JP | 9173437 | 7/1997 |
| 2004/0223676 | A1 | 11/2004 | Pope et al. | JP | 58 174718 | 10/1998 |
| 2005/0087915 | A1 | 4/2005 | Pope et al. | JP | 01 509570 | 7/2001 |
| 2005/0110187 | A1 | 5/2005 | Pope et al. | WO | WO 98/44270 | 10/1998 |
| 2005/0133277 | A1 | 6/2005 | Dixon et al. | WO | WO 99/02873 | 1/1999 |
| 2005/0146086 | A1 | 7/2005 | Pope et al. | WO | WO 99/14512 | 3/1999 |
| 2005/0158200 | A1 | 7/2005 | Pope et al. | | | |
| 2005/0203630 | A1 | 9/2005 | Pope et al. | | | |
| 2006/0121417 | A1 | 6/2006 | Dixon et al. | | | |
| 2006/0263233 | A1 | 11/2006 | Gardinier | | | |

FOREIGN PATENT DOCUMENTS

| | | | |
|---|---|---|---|
| GB | | 2 290 326 | 12/1995 |

OTHER PUBLICATIONS

U.S. Appl. No. 11/435,392, filed May 16, 2006, Pope et al.
U.S. Appl. No. 11/957,277, filed Dec. 14, 2007, Dixon et al.
ISTA Symposium Presentation, Sep. 1997.
ISTA Symposium Presentation, Oct. 1998.

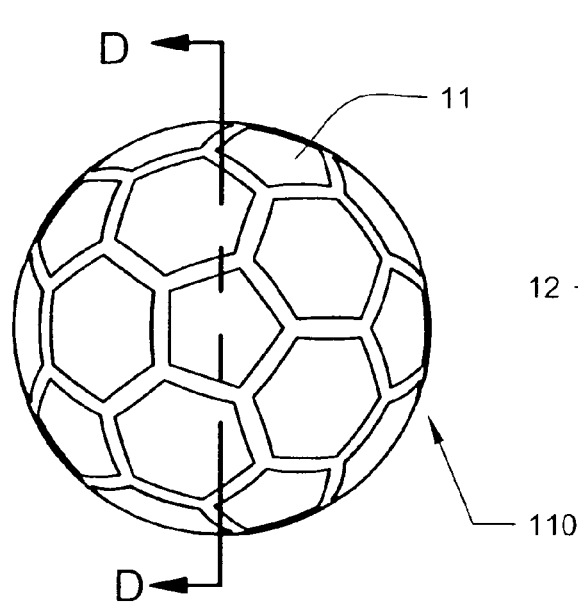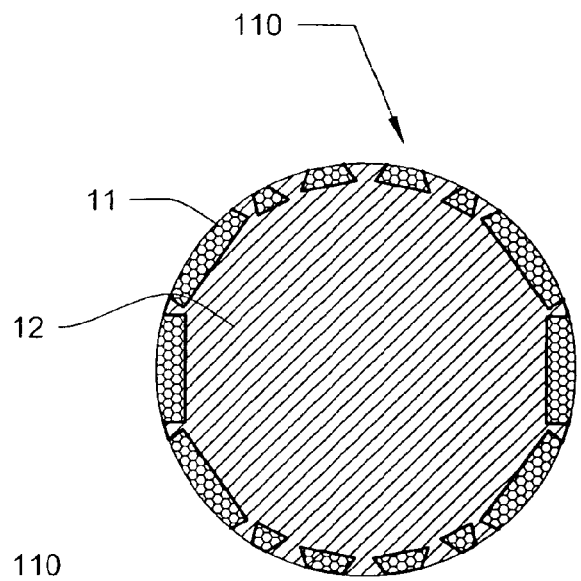
FIG. 2D-1          FIG. 2D-2
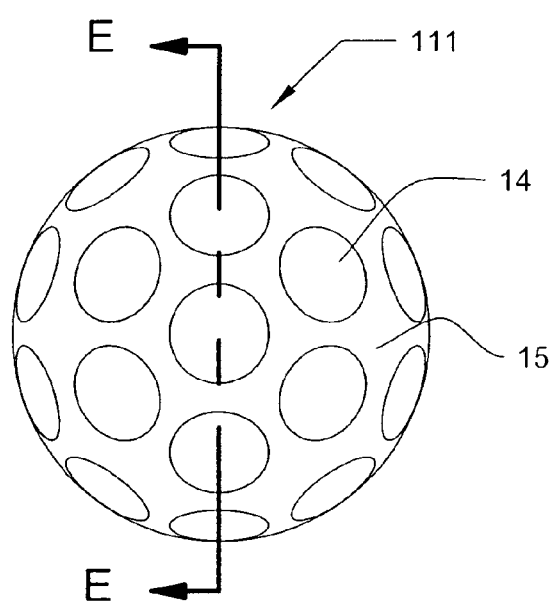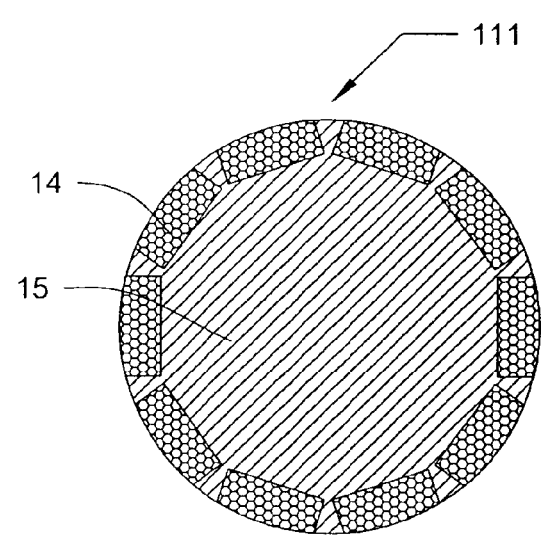
FIG. 2E-1          FIG. 2E-2

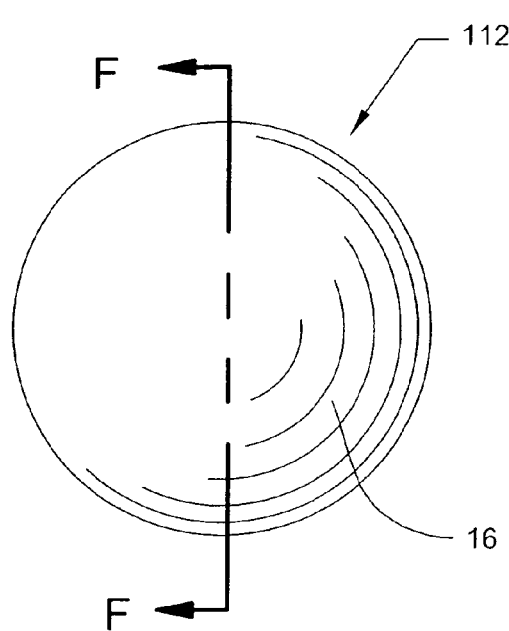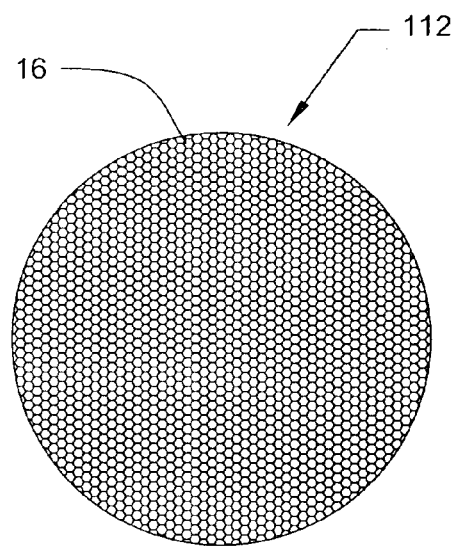# 
FIG. 2F-1    FIG. 2F-2
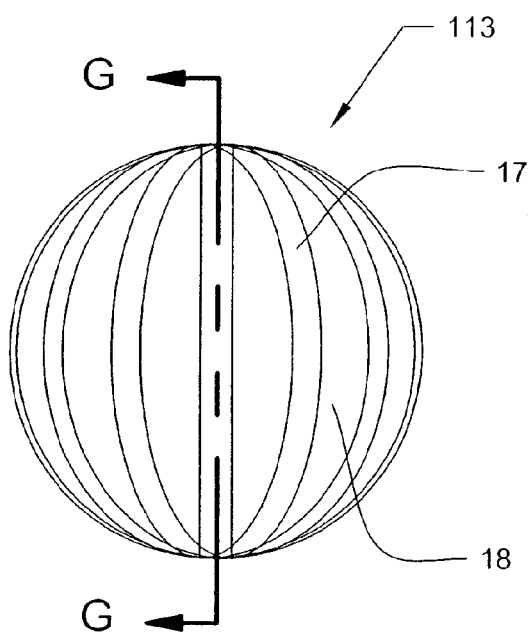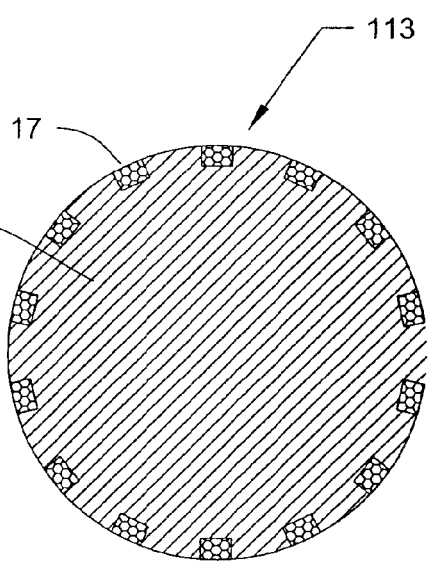
FIG. 2G-1    FIG. 2G-2

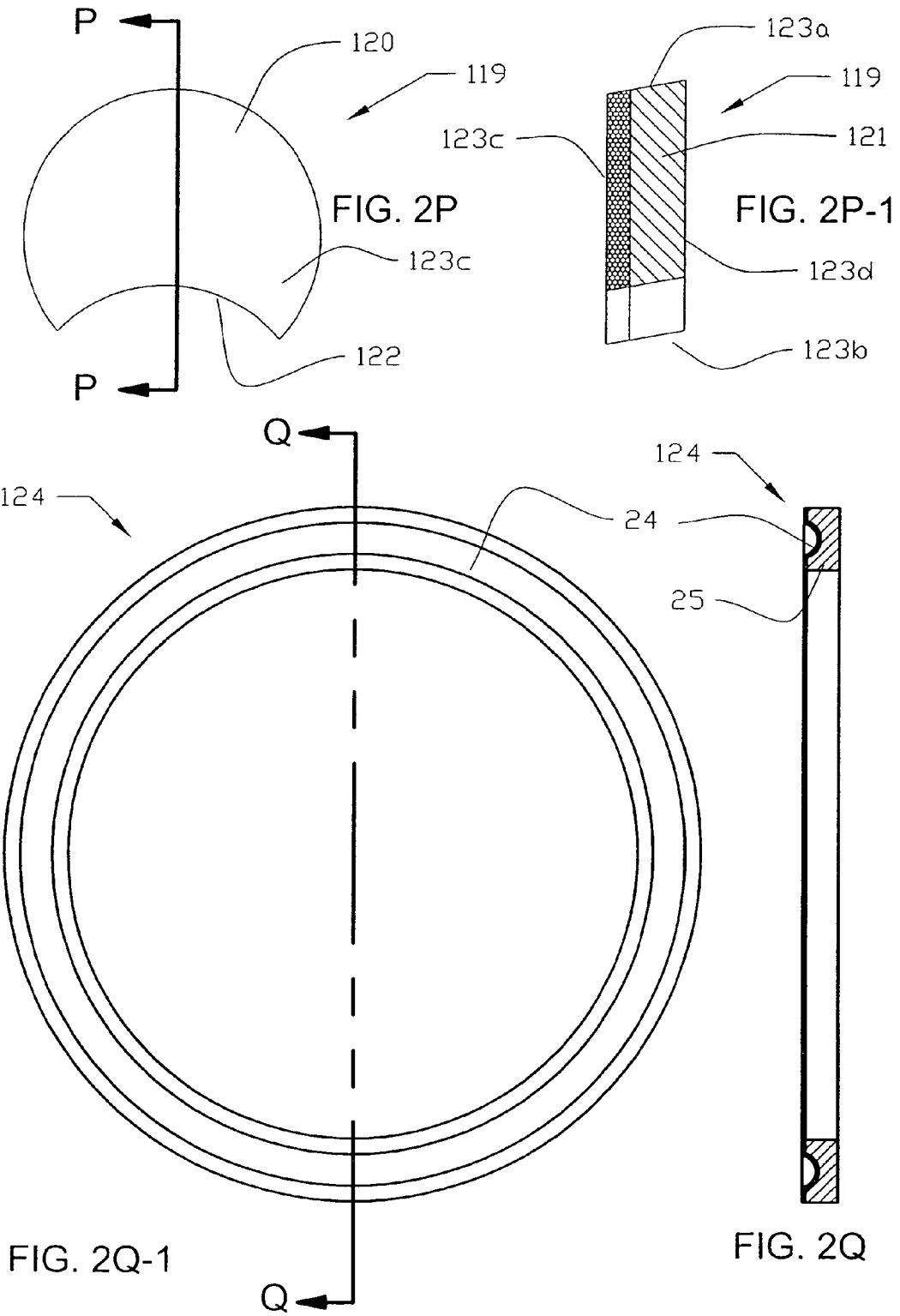

FIG. 2R-1
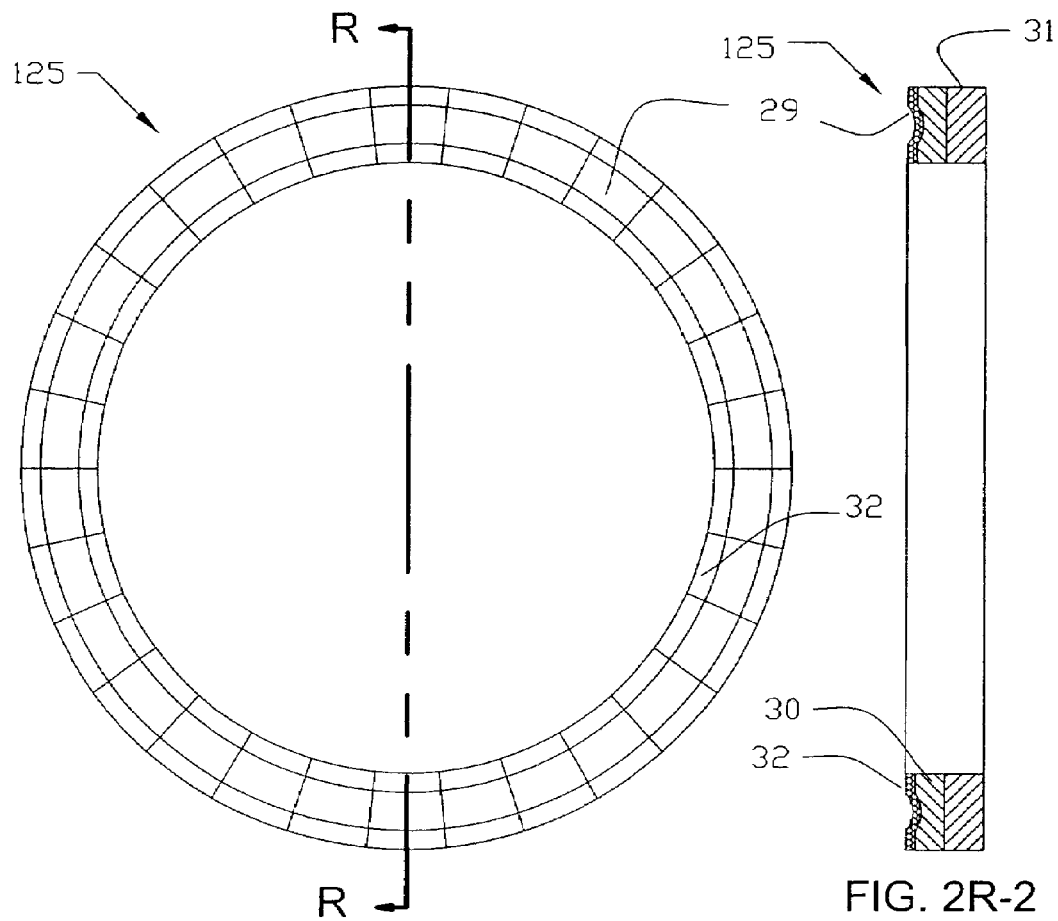
FIG. 2R-2
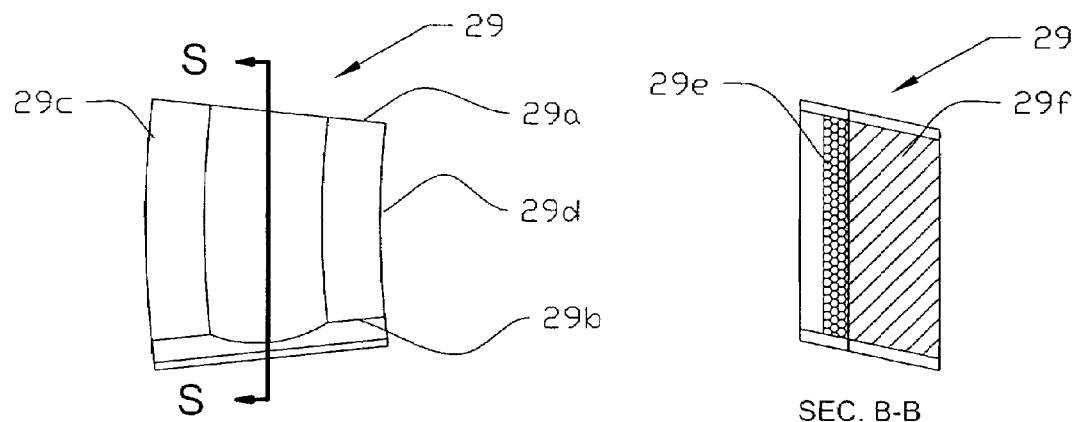
FIG. 2S-1
FIG. 2S-2

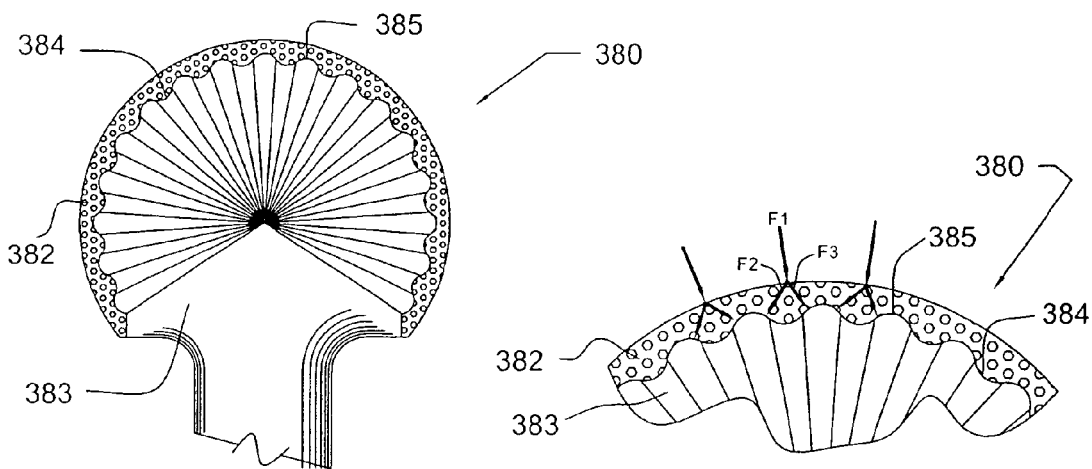
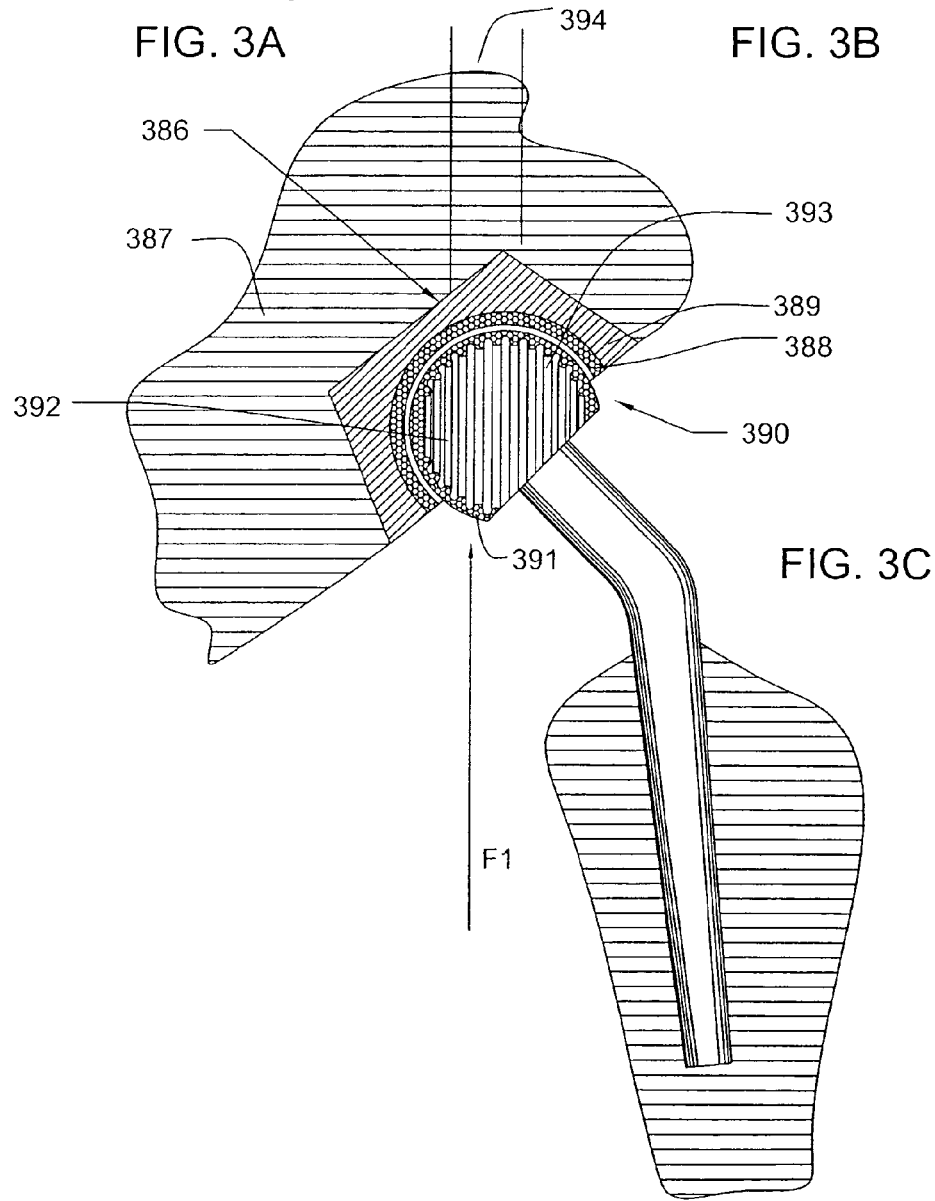
FIG. 3A
FIG. 3B
FIG. 3C

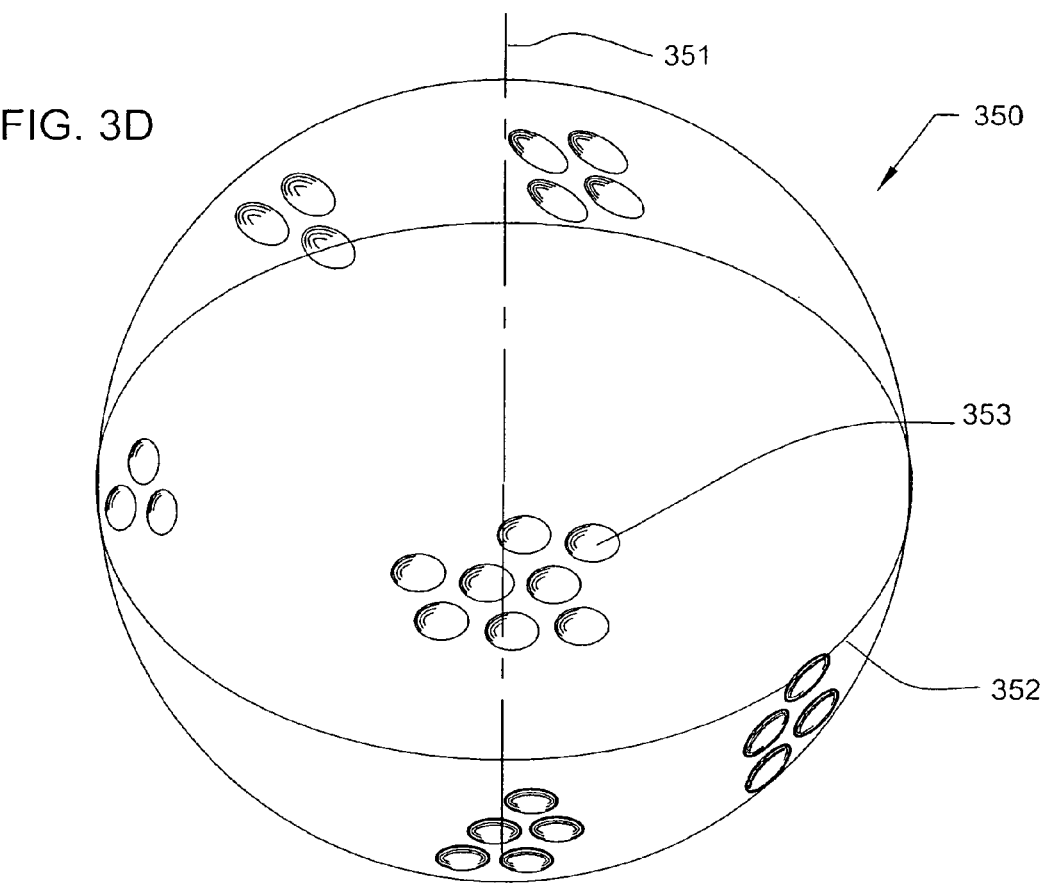
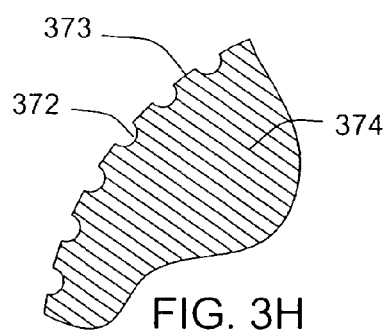
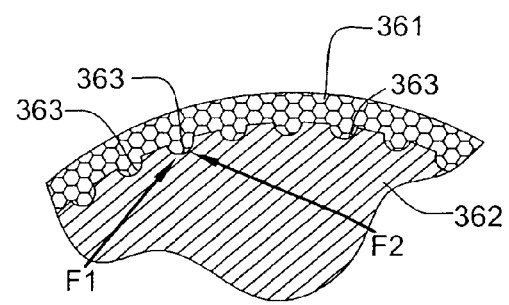
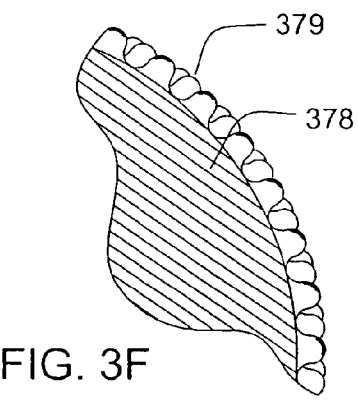
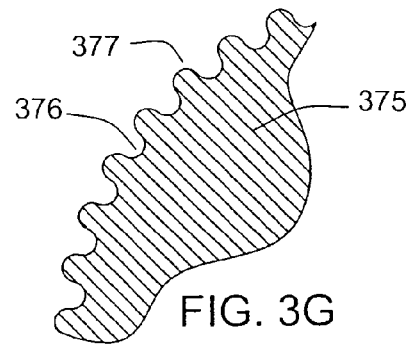

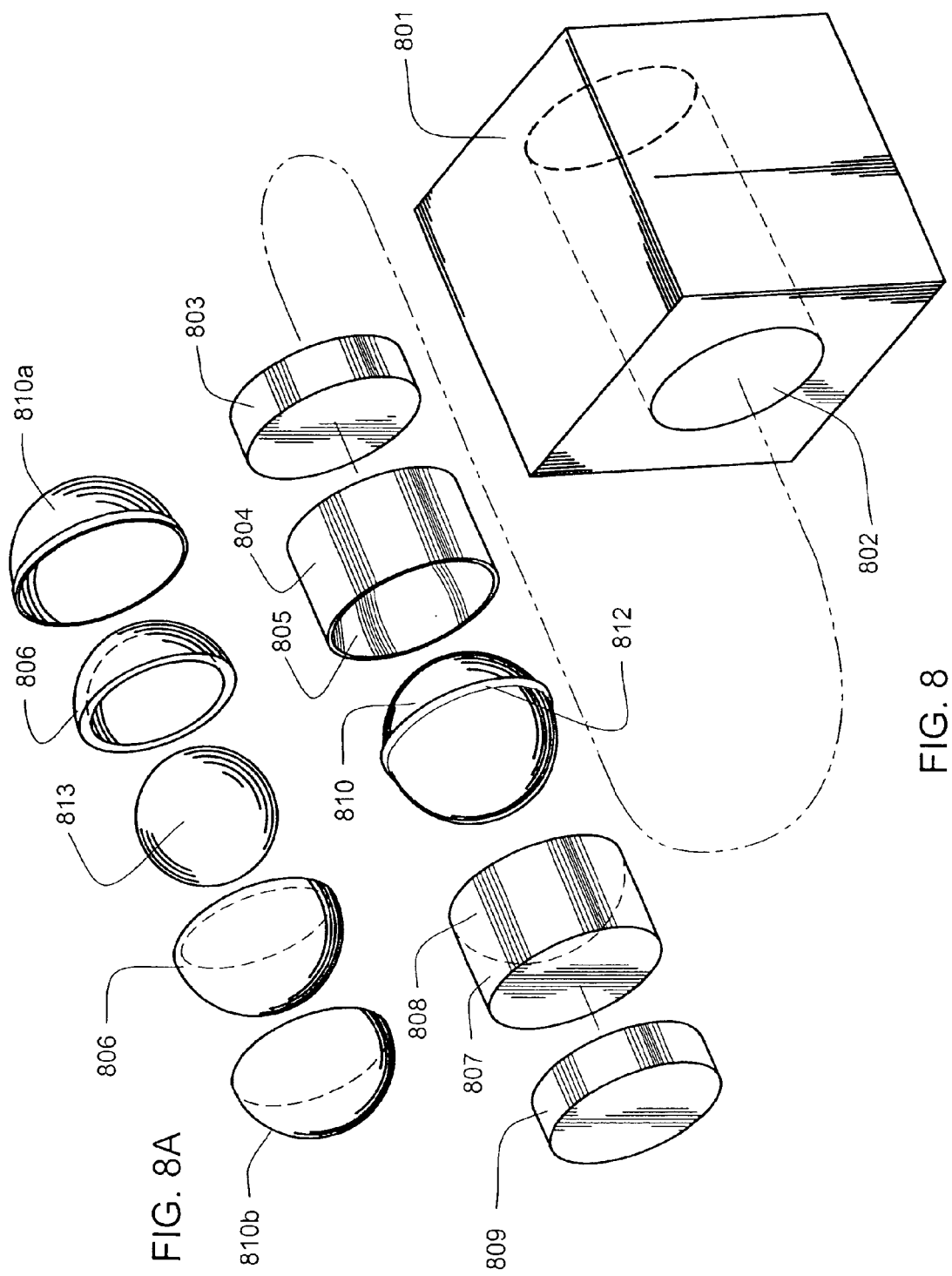

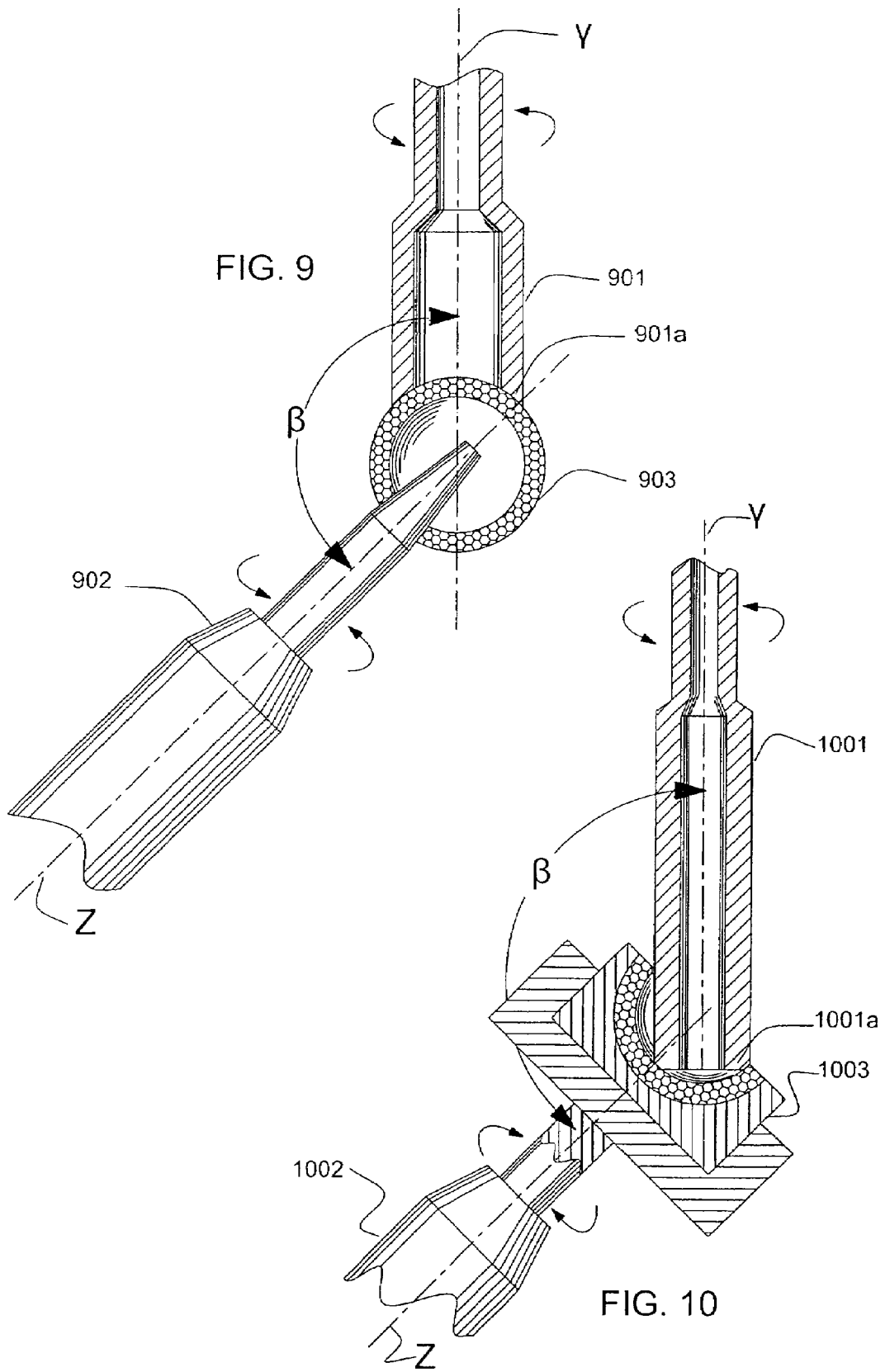

BEARINGS, RACES AND COMPONENTS THEREOF HAVING DIAMOND AND OTHER SUPERHARD SURFACES

CROSS-REFERENCE TO RELATED APPLICATIONS

This patent application is a continuation of U.S. patent application Ser. No. 10/643.806 filed on Aug. 18, 2003 now U.S. Pat. No. 7,461,978 which is incorporated herein by reference in its entirety and which is a continuation of U.S. patent application Ser. No. 09/840,634 filed on Apr. 22, 2001 now U.S. Pat. No. 6,655,845, and priority is claimed thereto.

BACKGROUND OF THE INVENTION

1. Field of the Invention

Various embodiments of the invention relate primarily to non-planar bearings, bearing components, races, race components, and methods for making the same. More specifically, some embodiments of the invention include bearings and/or bearing races which have contact, rolling or sliding (or a combination of them) surfaces manufactured in whole or in part from diamond, cubic boron nitride and other superhard materials. Many types of diamond can be used, including natural diamond, monocrystalline diamond, polycrystalline diamond compacts, and diamond produced by chemical vapor deposition and physical vapor deposition processes. Embodiments of the invention include methods for making, shaping and polishing the diamond portion of the bearing or race, including diamond surfaces thereof. As used generally herein, the term "bearing unit" may include a bearing, race, balls, rollers, cups, cage, bushings, shafts, journals and/or any related components useful for rolling or sliding (or a combination of them) articulation with another part.

2. Description of Related Art

This section will discuss art related to non-planar bearings, bearing components, races, race components.

Various embodiments of this invention relate to the application of diamond and other super hard surfaces to bearings and bearing elements. These bearings and bearing elements include both sliding and rolling bearing elements and bearing races. Bearings are an essential part of a vast array of mechanical devices. In these various applications, bearings withstand high concentrated forces, direct impact loads, and must reduce friction and energy loss in mechanical devices. In addition, they must maintain mechanical alignment of parts and maintain precision and accuracy of mechanical devices. Any bearing application, whether a sliding or rolling (or a combination of sliding and rolling) bearing, which is subject to wear, high loads, high maintenance, and/or complex lubrication requirements will benefit from embodiments in the invention. Although embodiments of the invention have other applications as well.

Typical bearing types may include ball bearing with races, roller bearings with races or tracks, and sliding element bearings. All bearings may include radial or sleeve type bearings to maintain shaft alignment and thrust bearings to provide for axial force transmission. Roller bearings may perform the same types of functions and can include cylinder rollers, tapered rollers, needle rollers, barrel rollers (both symmetrical and asymmetrical). Sliding element bearings may include devices such as bushings, journals and ball bearing components and constrained articulating bearing components within mechanical devices.

Materials from which bearing components are fabricated depend upon the mechanical requirements for a specific application. Desirable properties for these materials include durability, resistance to fracture and wear, resistance to heat, low coefficient of thermal expansion especially compared to typical metals used in bearings, low coefficient of friction for sliding contact with no lubricant and affinity for any lubricants which may be required to enhance the mechanical operation of the bearing. Various types of lubricants and lubrication systems may be used to enhance bearing operation and may increase the durability and longevity of function. The ability to function with little or no lubrication is desirable as lubricants add complexity to bearing systems.

Lubricants that might be used include; solid media such as graphite, molybdenum, PTFE, powdered media of the same compositions, fluid media, including water, hydrocarbons, fluorocarbons, halogenated hydrocarbons, complex hydrocarbons such as fats and fatty acids, silicone based lubricants and any other fluid. In some applications, fluids used for lubrication may be abrasive and/or corrosive, such as in oil well drilling apparatus, or corrosive fluid pumping systems.

Bearings may be called upon to perform many functions in a rotating, articulating or sliding animate or inanimate mechanical devices. These include, but are not limited to, sustaining high loads, maintaining precision of alignment, preserving a low coefficient friction for mechanical motion and enduring high impact shock loads. In addition, they must perform these various functions often in stressful environments, such as those entailing high temperature and or the presence of corrosive chemical agents, erosive environments or any other hostile environment.

An ideal material for bearing application would include having high hardness, high fracture toughness, low coefficient of mechanical friction, chemical inertness, thermal stability and high thermal conductivity. Current materials used to produce bearings and races include hard non ferrous alloys, hardened steels, ceramics, plastics (including polyethylene), and crystalline materials such as silicon carbide, titanium nitride and aluminum oxide. All of these materials are limited in their utility for this application due to their susceptibility to wear, deformation under load, susceptibility to fracture, degradation in corrosive environments and thermal breakdown.

Bearing wear or degradation results in loss of alignment of mechanical parts leading to further acceleration of wear and or disruption of other mechanical components, increased heat generation, further acceleration of bearing wear, with final catastrophic failure.

The ability of diamond to resistance wear exceeds that of all other materials. Further, diamond has desirable thermal stability, thermal conductivity, chemical inertness, and facture toughness to enhance bearing performance. The table below compares properties of polycrystalline diamond compact with some other materials from which bearing surfaces can be made.

TABLE 1

COMPARISON OF DIAMOND TO OTHER MATERIALS

| Material | Specific Gravity | Hardness (Knoop) | Thermal Conductivity (W/m K) | CTE ($\times 10^{-6}$ in/in ° C.) | Young's Modulus ($\times 10^6$ psi) | Possion's Ratio | Bulk Modulus ($\times 10^6$ psi) |
|---|---|---|---|---|---|---|---|
| Sintered Polycrystalline Diamond | 3.5-4.0 | 7500-10,400 | 900-2600 | 1.0-4.8 | 120 | 0.7-0.22 | 65-82 |
| Sintered Cubic Boron Nitride | 3.48 | 3500-4500 | 800 | 1.0-4.0 | 100-110 | 0.20-0.22 | 55-65 |
| Silicon Carbide | 3.00 | 2500 | 84 | 4.7-5.3 | 58 | 0.17 | 30 |
| Aluminum Oxide | 3.50 | 2000 | 8 | 7.8-8.8 | 53-55 | 0.24 | 34-35 |
| Tungsten Carbide (10% Co) | 14.6 | 2200 | 112 | 6.0 | 80-90 | 0.22 | 48-54 |
| Cobalt Chrome | 8.20 | 278-351 | 11.2-14.3 | 11-16 | 33-35 | 0.293-0.306 | 27-30 |
| Ti6Al4V | 4.43 | 309 | 6.6-17.5 | 11 | 15-17 | 0.26-0.36 | 11-20 |
| Silicon Nitride | 3.20 | 14.2 | 15.7 | 1.8-3.7 | 27-46 | 0.2-0.27 | 15-33 |

A particular problem with prior art bearings is a tendency to develop catastrophic accelerated wear when a third body wear particle of sufficient hardness is introduced into the bearing environment.

The failures and pervasive limitations of the prior art show a clear need for improved bearings, bearing components, races, race components, and methods for making the same.

SUMMARY OF THE INVENTION

Polycrystalline diamond compact is, in many ways, an ideal material for bearing applications. Currently polycrystalline diamond compacts are employed in the most demanding of mechanical application such as earth boring and rock cutting. Unfortunately, no one has developed the technology to fabricate polycrystalline diamond compacts of this invention for typical non-planar bearing applications.

It is the object of some embodiments of this invention to provide components for non-planar rolling or sliding (or a combination of rolling and sliding) bearings which have increased wear resistance, decreased coefficient of friction, increased resistance to hostile environments and increased ability to sustain high loads and high impact forces without undergoing degradation compared to prior art bearings. It is a feature of this invention that bearings and/or races are provided that utilize diamond and other superhard materials in or on their articulating surfaces.

It is an object of some preferred embodiments of the invention to provide bearings and races which can function well in the absence of lubrication or with significantly diminished lubrication compared to prior art bearings used in similar applications. Diamond is known to transfer heat very well and even in its ordinary state, sintered polycrystalline diamond exhibits excellent thermal stability. When metal located in interstitial spaces in polycrystalline diamond compacts is removed, ability of the part to withstand heat is improved. In some embodiments of the invention, superior thermally stable diamond may be created by using the processes disclosed in U.S. Pat. Nos. 5,127,923; 4,163,769 and 4,104,344, each of which is hereby incorporated by reference.

It is a further object of some embodiments of this invention to provide bearings and bearing elements with high chemical and thermal stability, which function in a superior way compared to prior art bearings and similar applications. Accordingly, not only do the invented bearings and races avoid heat buildup because of their low coefficient of friction and high thermal conductivity, they also resist heat damage due to their superior thermal stability.

It is a further object of some embodiments of this invention to provide bearings fabricated with diamond and other superhard materials. Diamond and the other superhard materials of the invention achieve various objects stated herein.

It is also an object of some embodiments of the invention to provide bearings and races that have a high affinity for lubricants of both polar and non polar varieties, with lower frictional losses than prior art bearings and races. Diamond is known to have extremely high surface energy, rendering it very wettable and easy to lubricate. This feature provides improved utility, durability, and function in the invented devices compared to the prior art.

It is a further object of this invention to provide bearings, bearing elements and races with extremely high thermal transfer so that heat may be transferred away from contact surfaces more efficiently, improving bearing durability, utility, and longevity. Consequently, bearing life is increased and integrity of any lubricants is preserved.

It is a further object of some embodiments of this invention to provide precision bearings for use and applications where high precision and high accuracy are required. The invented bearings and races maintain precision and accuracy for longer periods due to their extreme low wear, high hardness and high toughness compared to prior art bearings.

It is a further object of some embodiments of this invention to provide rotating or rolling bearings of ball, barrel, shaft, sleeve and pin types, which articulate against races or other counter bearing surfaces, in which at least some of the contact surface is diamond or another superhard material. The diamond or superhard material may be provided across the entire contact surface or only a portion thereof, such as through the use of diamond segments on a contact surface.

It is a further object of some preferred embodiments of this invention to provide bearings that include rolling elements consisting of either continuous or segmented diamond or other super hard material. These bearings and rolling elements may articulate with races or other counter bearing surfaces which are fabricated from non-diamond materials, such as aluminum oxide, steel, tungsten carbide, silicon carbide, polymers, etc.

It is a further object of some embodiments of this invention to use races with diamond or other superhard materials articulating against rolling elements that have non-diamond surfaces, such as aluminum oxide, steel, tungsten carbide, hardened steels, silicon carbide, polymers, and others.

It is a further object of some preferred embodiments of this invention to use races that have diamond or other superhard material inlaid on them in segmented fashion. The diamond or superhard segments may be round or adjacent round nested components, parallelograms, hexagonal components, tetragonal components, radial tetragonal components, combinations of these and other geometries.

It is another object of some preferred embodiments of this invention to use rolling elements which have segmented diamond or other super hard material bearing surfaces including circular or polyhedral geometries. The circular or polyhedral geometries may include strips or veins of superhard material on the surface of the bearing element, the strips or veins being arranged in various desired geometries, such as longitudinal or latitudinal lines, spirals, concentric circles, straight lines, or otherwise.

It is another object of some embodiments of this invention to provide roller bearings for radial and thrust applications consisting of cylindrical rollers, barrel rollers, asymmetrical barrel rollers and conical section-tapered rollers.

It is another object of some embodiments of this invention to provide bearings which are resistant to chemical attack and degradation in hostile environments, such as corrosive or erosive environments. The nature of diamond and other preferred superhard materials is such that resistance is provided to hostile environments.

It is another object of some embodiments of this invention to provide bearings of geometries that are resistant to fracture under impact loads.

It is another object of some embodiments of this invention to provide bearings of geometries that can sustain high loads per unit size without degradation.

It is another object of some embodiments of this invention to provide bearings of geometries that can sustain high loads for long service cycles without significant wear, degradation and accuracy or precision, while maintaining a low coefficient of friction.

It is another object of some embodiments of this invention to provide methods of manufacturing and finishing of bearings, races and bearing components.

It is an object of some embodiments of the invention to provide components for bearings having increased wear resistance and a decreased coefficient of friction even in the absence of lubricant, therefore maximizing life of the bearing component. It is a feature of some embodiments of the invention that diamond of various types and other superhard materials are used for the bearing surfaces, the superhard materials including diamond being very resistant to wear and having a very low coefficient of friction. For the purposes of this document, a superhard material is a material that has a Knoop hardness of at least about 4000. This includes sintered polycrystalline diamond and other diamond, diamond-like materials, cubic boron nitride and wurzitic boron nitride.

It is an object of some embodiments of the invention to provide a bearing component that does not shed significant amounts of debris or wear particles as a result of use or wear. It is a feature of some embodiments of the invention that polycrystalline diamond compacts or other superhard materials are used to form at least one of the articulation surfaces of the bearing component, resulting in a low friction and long wearing bearing component that sheds little to no debris or particles during use, and which destroys abrasive third bodies with minimal or no damage to the bearings.

It is another object of some preferred embodiments the invention to use the hardest materials known to man, namely diamond, cubic boron nitride and other superhard materials to give bearing components the highest resistance to wear currently known to man. It is a feature of the invention that some preferred embodiments use sintered polycrystalline diamond ("PCD") and sintered polycrystalline diamond compacts ("PDC") for bearing surfaces. For the purposes of this document, a polycrystalline diamond compact includes a volume of PCD attached to a substrate material, whether chemically or physically bonded to the substrate, or both. The polycrystalline diamond is extremely hard and, when polished, has one of the lowest coefficients of friction of any known material. It is a consequent advantage of the invention that the bearing component life far exceeds that of prior art metal and/or ceramic bearings. The polycrystalline diamond compact may be manufactured by a variety of methods, including high pressure and high temperature sintering in a press, chemical vapor deposition, physical vapor deposition, and others.

It is an object of some embodiments of the invention to provide non-planar diamond and superhard bearing component surfaces. Various embodiments of the invention provide novel bearing surfaces that are non-planar and may be manufactured as polycrystalline diamond compacts.

It is an object of some embodiments of the invention to provide a method for manufacturing non-planar polycrystalline diamond compact bearing surfaces. Various methods are disclosed for materials preparation and polycrystalline diamond compact manufacturing that will produce non-planar polycrystalline diamond compact bearing surfaces, including but not limited to concave and convex spherical bearing surfaces.

It is an object of some embodiments of the invention to provide methods for rough shaping of non-planar superhard bearing surfaces. Novel machining techniques are disclosed which accomplish such shaping.

It is an object of some embodiments of the invention to provide methods for finish polishing of non-planar superhard bearing surfaces. Novel polishing techniques are disclosed which permit polishing of superhard compact bearing surface to be highly polished to a low coefficient of friction.

The objects, features and advantages of the inventions mentioned above are exemplary and illustrative only so that the reader may begin to perceive advantages to be accrued by use of the invention alone or in combination with other technology. Additional objects, features and advantages of the invention will become apparent to persons of ordinary skill in the art upon reading the specification and claims and viewing the drawings.

BRIEF DESCRIPTION OF THE DRAWINGS

FIGS. 2B-1 and 2B-2 depict a roller thrust bearing.

FIGS. 2C-1 and 2C-2 depict a ball bearing with a surface volume of diamond on a substrate.

FIGS. 2D-1 and 2D-2 depict a ball bearing with segmented bearing inserts or patches on its surface.

FIGS. 2E-1 and 2E-2 depict a ball bearing with segments having a surface of polycrystalline diamond compact or other superhard material fixed securely into a spherical substrate ball.

FIGS. 2F-1 and 2F-2 depict a ball constructed of polycrystalline diamond or other superhard material.

FIGS. 2G-1 and 2G-2 depict a ball bearing with strips, veins or a discontinuous pattern of diamond fixed into a substrate ball.

FIGS. 2H, 2H-1 and 2H-2 depict a radial ball bearing assembly.

FIGS. 2K and 2K-1 depict a cylindrical roller bearing assembly.

FIG. 2L-1 and 2L-2 depict a radial ball bearing assembly with radial tetragonal segmented bearing races.

FIGS. 2M-1 and 2M-2 depicts a thrust bearing.

FIGS. 2P and 2P-1 depict a diamond compact insert for the race of FIGS. 2M-1 and 2M-2.

FIGS. 2Q and 2Q-1 depict a thrust bearing of the invention.

FIGS. 2R-1 and 2R-2 depict a thrust bearing with angular inlaid segments of diamond or other superhard material.

FIGS. 2S-1 and 2S-2 depict an angular segment for use in the thrust bearing of FIGS. 2R-1 and 2R-2.

FIGS. 2T-1 and 2T-2 depict a thrust bearing race with multiple circular or oval segment bearing elements inlayed into the appropriate thrust bearing race substrate.

FIG. 4BB depicts a sintered polycrystalline diamond compact in which there is a continuous gradient transition from substrate metal through the diamond table.

FIGS. 6A-1 and 6A-2 depict an assembly useful for making a convex spherical polycrystalline diamond compact.

FIGS. 6B-1 and 6B-2 depict a substrate useful for making concave spherical polycrystalline diamond compacts.

FIGS. 8 and 8A depict a precompaction assembly, which may be used to reduce porosity or free space in diamond feedstock prior to sintering.

FIG. 9 depicts EDM rough finishing of a convex spherical part, such as a ball bearing.

FIG. 10 depicts EDM rough finishing of a concave spherical part, such as a race or a portion thereof.

DETAILED DESCRIPTION OF THE PREFERRED EMBODIMENTS

Reference will now be made to the drawings in which the various elements of the present invention will be discussed. It will be appreciated that the structures and principles of the invention can be applied not only to the illustrated examples, but also to many other types of articulation surfaces, to the manufacture, shaping and finishing of superhard materials and superhard components, and to the manufacture, shaping and finishing of devices using superhard articulation surfaces and superhard components. Persons skilled in the design of bearing components and other bearing surfaces will understand the application of the various embodiments of the invention and their principles to bearing components, bearing surfaces and devices other than those exemplified herein.

A. Bearing and Race Structures of the Invention

Below, some preferred bearing and race structures that may be made according to the principles of the invention are described as examples. In later sections of this document, details on appropriate materials for making the bearings and races, manufacturing, shaping and finishing processes are described in greater detail. It will be appreciated to those accustomed to the art that the structures and principles of the invention can be applied not only to the specific illustrated examples, but also to other types of articulating surfaces, both sliding and rolling bearings, and to the manufacture of super hard materials and super hard components for other applications.

Figure 1A:
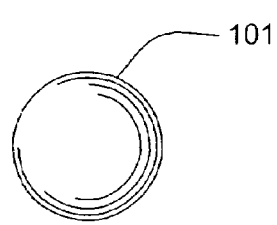
FIG. 1A depicts a ball bearing element of the invention.

FIG. 1A depicts a ball bearing element 101 of the invention.

Figure 1B:
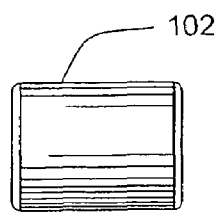
FIG. 1B depicts a cylindrical roller bearing element of the invention.

FIG. 1B depicts a cylindrical roller bearing element 102 of the invention.

Figure 1C:
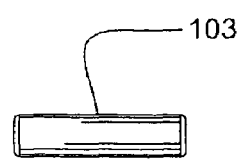
FIG. 1C depicts a needle roller bearing element of the invention.

FIG. 1C depicts a needle roller bearing element 103 of the invention.

Figure 1D:
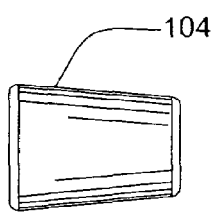
FIG. 1D depicts a tapered roller bearing element of the invention.

FIG. 1D depicts a tapered roller bearing element 104 of the invention.

Figure 1E:
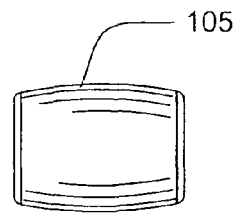
FIG. 1E depicts a symmetrical barrel roller bearing element of the invention.

FIG. 1E depicts a symmetrical barrel roller bearing element 105 of the invention.

Figure 1F:
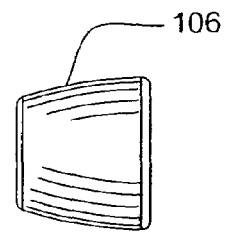
FIG. 1F depicts an asymmetrical barrel roller bearing element of the invention.

FIG. 1F depicts an asymmetrical barrel roller bearing element 106 of the invention.

Each of the bearing elements 101-106 may be made from solid PCD, a polycrystalline diamond compact, or other diamond or superhard materials, as desired.

Figures 2, 2A:
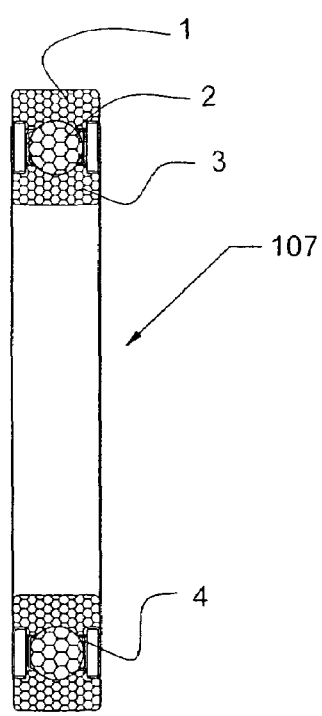
FIGS. 2A-1 and 2A-2 depict a radial ball bearing assembly with inner and outer races and cages.
Figures 1, 2A:
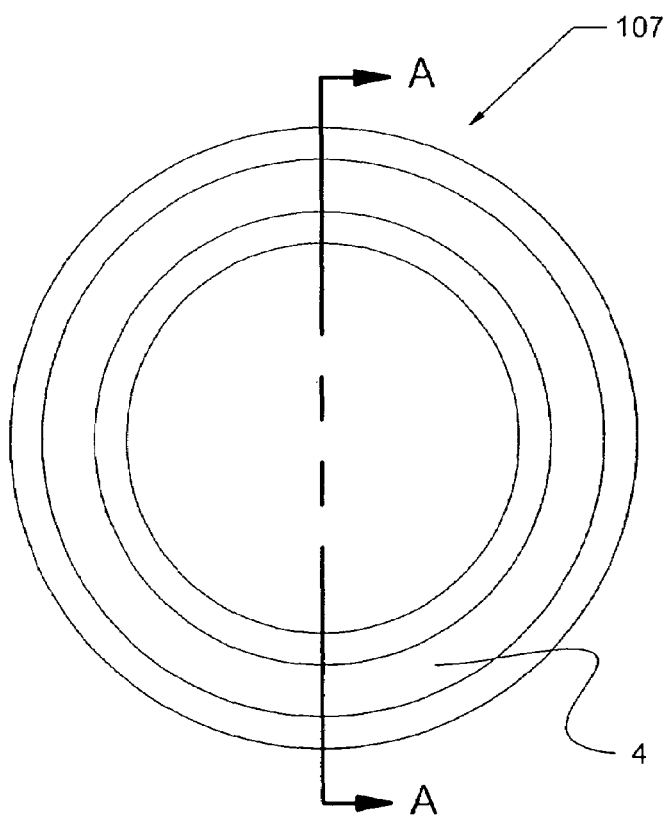

FIGS. 2A-1 and 2A-2 depict a radial ball bearing assembly 107 with inner and outer race cages. An outer race 1, and inner race 3, a bearing rolling ball element 2 and a cage 4 to contain the bearings inside the bearing assembly while articulating are depicted. Contact surfaces of the balls 2 or the races 1 and 3 may be diamond or superhard material in whole or in part.

Figures 1, 2, 2B:
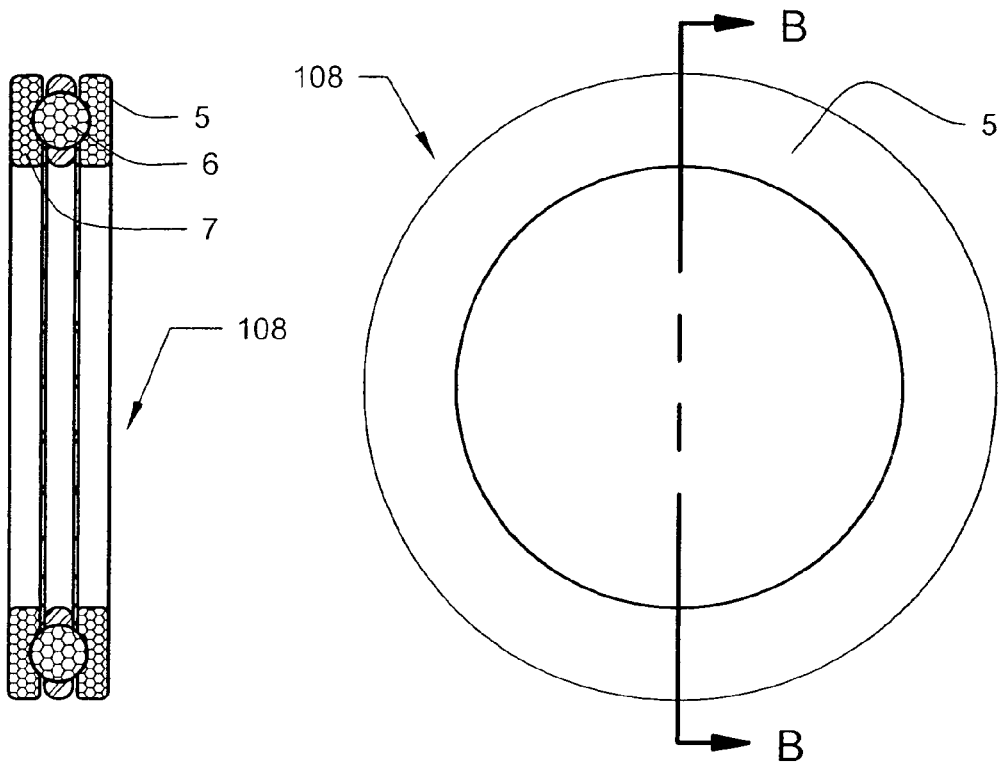

FIGS. 2B-1 and 2B-2 depict a roller thrust bearing. Bearing rolling ball elements 6 roll and articulate with races 5 and 7 and the bearing cage 8. Contact surfaces of the balls or the races may be diamond or superhard material in whole or in part.

Figures 1, 2, 2C:
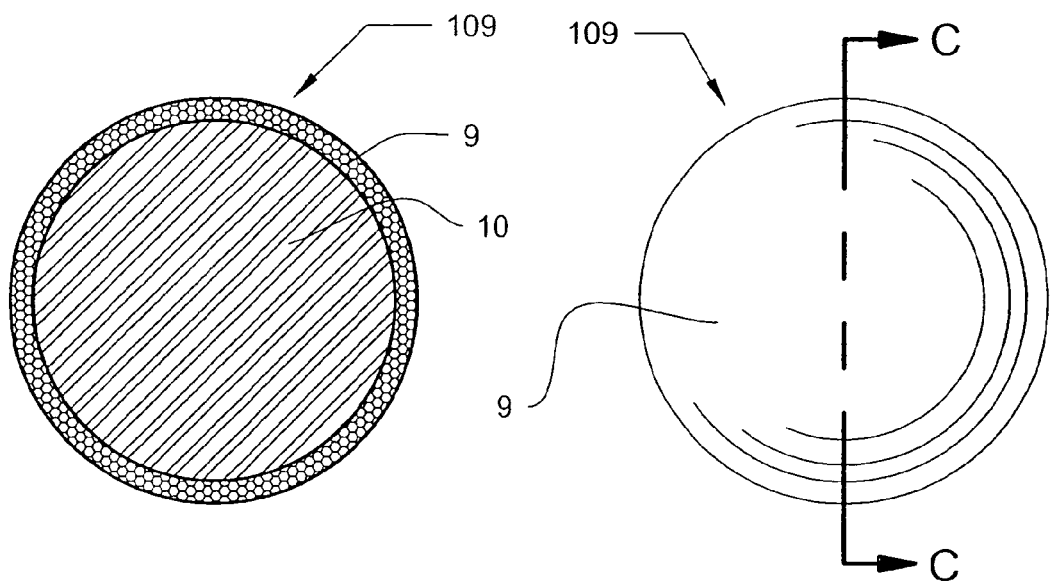

FIG. 2C-1 and 2C-2 depict a ball bearing 109. The ball bearing 109 depicted may be a polycrystalline diamond compact that includes a surface volume of diamond 9 on a substrate 10. This embodiment includes a continuous surface layer of diamond, although the diamond surface may be discontinuous as well. The substrate may be any suitable substrate as described elsewhere herein.

Some embodiments of the invention may include a surface volume of polycrystalline diamond compact, diamond applied through vapor deposition means (such as chemical vapor deposition or physical vapor deposition), polycrystalline cubic boron nitride compact or other super hard material. The surface volume of diamond or superhard material may be applied to an appropriate durable substrate, which may include an appropriate durable metal, ceramic material, composite material, or crystalline material. In one preferred implementation the surface layer consists of polycrystalline diamond compact applied to a metallic substrate. This means that the diamond is chemically bonded to the substrate to provide an extremely hard low friction durable long lasting articulating surface for the bearing. In bearing applications the surface geometry would be finished to a suitable precision and accuracy conducive to smooth glass like finish with a very low coefficient of friction. Diamond is extremely hard and possesses an extremely low coefficient of friction. Consequently, when diamond is used, the wear between the surface layer of diamond and any part which it articulates against would be negligible over time resulting in an extremely long lasting durable part. In addition, because of the extreme toughness of the diamond surface on metal substrate constructed as a compact, the rolling bearing element has extremely high fracture toughness making it desirable as a bearing element where peak loads and impacts are experienced as part of duty cycle.

FIGS. 2D-1 and 2D-2 depict a ball bearing 110 with bearing inserts 11 on the surface 12 to form a discontinuous diamond surface. The inserts 11 may be located on the substrate material with great precision and accuracy. The bearing surface of the ball bearing depicted may be divided into areas of diamond or other superhard material separate by veins of substrate material. Fabrication of balls with this vein and patch structure (such as a polyhedral or round segmented surface) offer some advantages to the manufacturing process for certain substrate metals as well as provide some advantages in high impact situations. Each bearing segment of diamond or superhard material independently accommodate transient deformations under peak load without resulting in fracture of the segments of diamond or superhard material.

FIGS. 2E-1 and 2E-2 depicts a cross-sectional view of a ball bearing 111 with plugs 14. The plugs 14 may be a polycrystalline diamond compact having a surface of polycrystalline diamond or other superhard material. The plugs 14 may be fixed securely into receptacles on spherical substrate ball 15 or other desired structure. The plugs or segments may be fashioned as polycrystalline diamond compacts or other superhard material. Each plug may be a continuous phase of superhard material, or a compact formed from a bearing surface of superhard material on a substrate, such as a polycrystalline diamond compact. The plugs may be bonded, welded, or mechanically fastened to the substrate structure, preferably in an appropriate receptacle, leaving the superhard bearing surface exposed. High quality curvilinear and spherical surface finishes that are obtained by terminal finishing processes described later in this document. This approach to segmented bearing surfaces permits the fabrication of extremely large spherical and or curvilinear bearing surfaces not possible with continuous bearing surfaces. Size limitations in the manufacturing of polycrystalline diamond compact elements might otherwise prevent manufacture of such large bearing elements.

FIGS. 2F-1 and 2F-2 depict a ball 112 constructed of solid or continuous phase polycrystalline diamond or other superhard material. This ball 112 is made of solid diamond or superhard material without a separate substrate. The ball 112 has a continuous phase of diamond throughout its interior. Embodiments of such a continuous phase bearing element may be made from polycrystalline diamond, polycrystalline cubic boron nitride, or other superhard material. This structure has certain advantages from a chemical electromagnetic and structural standpoint.

FIGS. 2G-1 and 2G-2 depict a ball bearing 113 with strips, veins or a discontinuous pattern of diamond 17 or another superhard material located on a substrate 18. The diamond on the ball 113 surface may be in a regular or irregular discontinuous pattern in any desired geometry, such a concentric circles, spirals, latitudinal or longitudinal lines or otherwise. This structure possesses some of the advantages common to the segmented bearing surface described above.

Figure 2H:
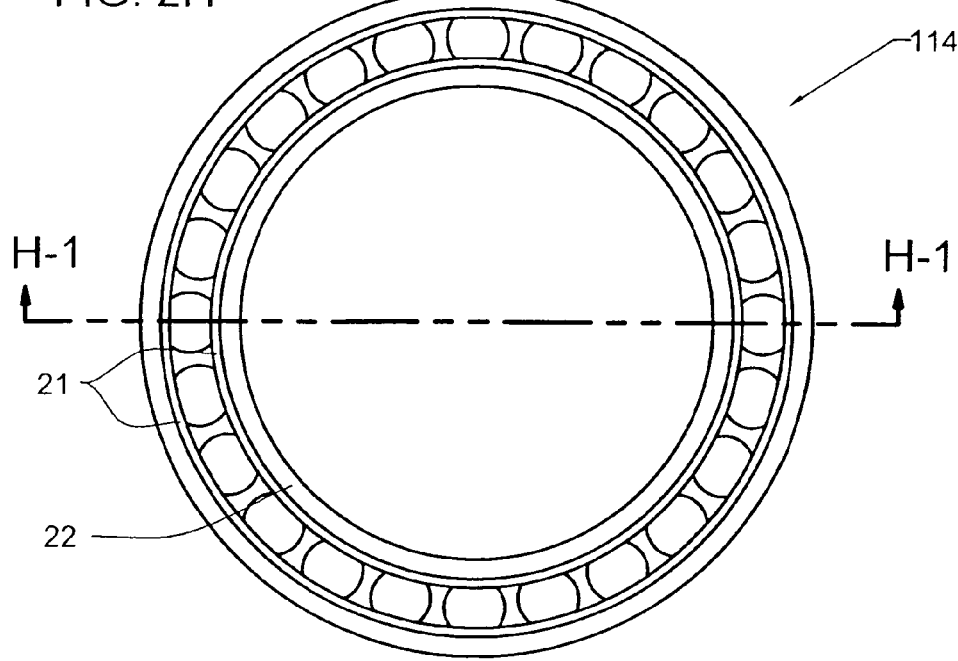
Figures 1, 2H:
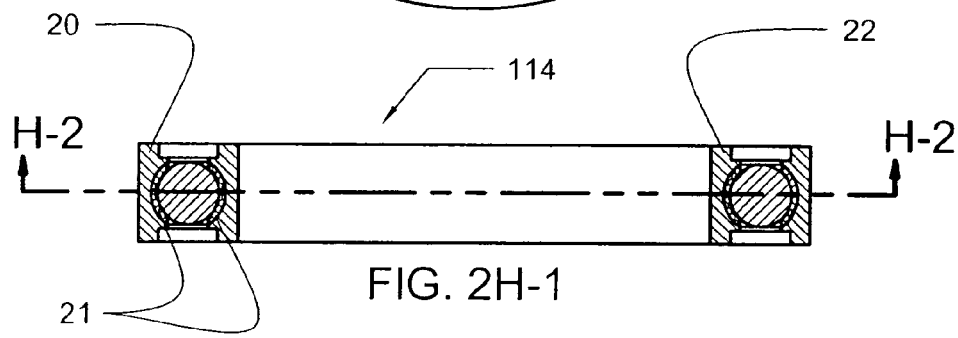
Figures 2, 2H:
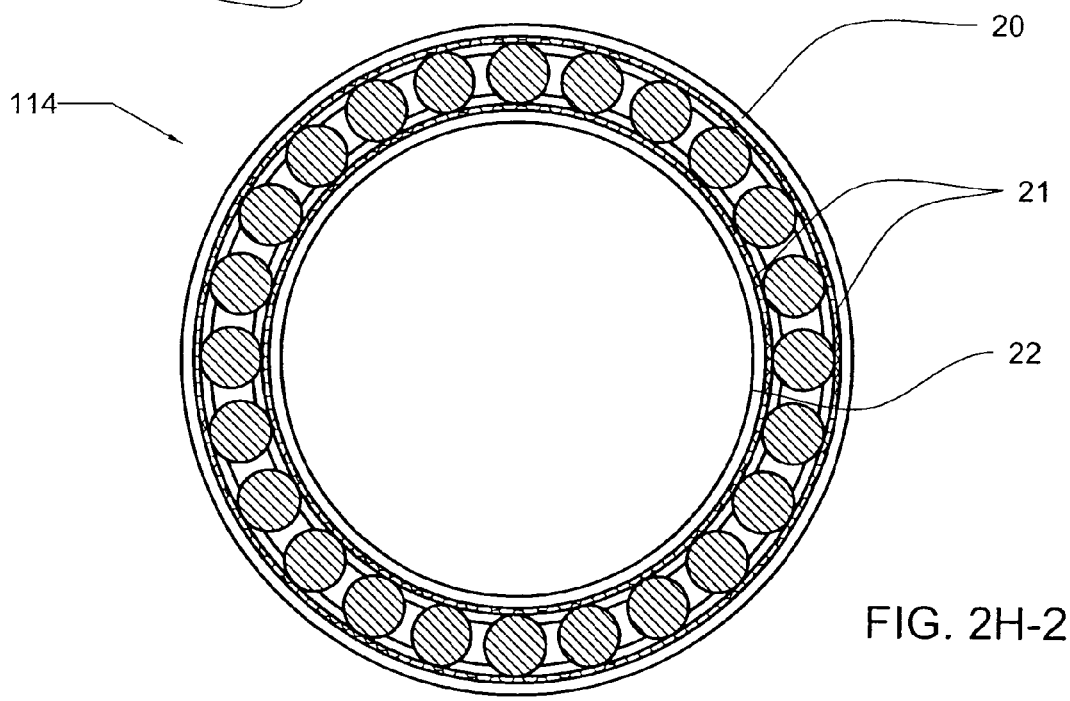

FIGS. 2H, 2H-1 and 2H-2 depict a radial ball bearing assembly 114. The bearing assembly 114 includes an outer race 20 and an inner race 22, each of which may have continuous diamond or other superhard articulating surfaces 21. Various manufacturing technologies can be used to apply a diamond layer to bearing surfaces, including direct fabrication of PDC at the race surfaces, chemical vapor deposition and physical vapor deposition. Additionally, where needed or desired, the inner race, outer race or both may be fabricated entirely of PDC structure. When the race is PDC, the roller bearing element may also be PDC or it may be another superhard material or another non-superhard material.

Figure 2K:
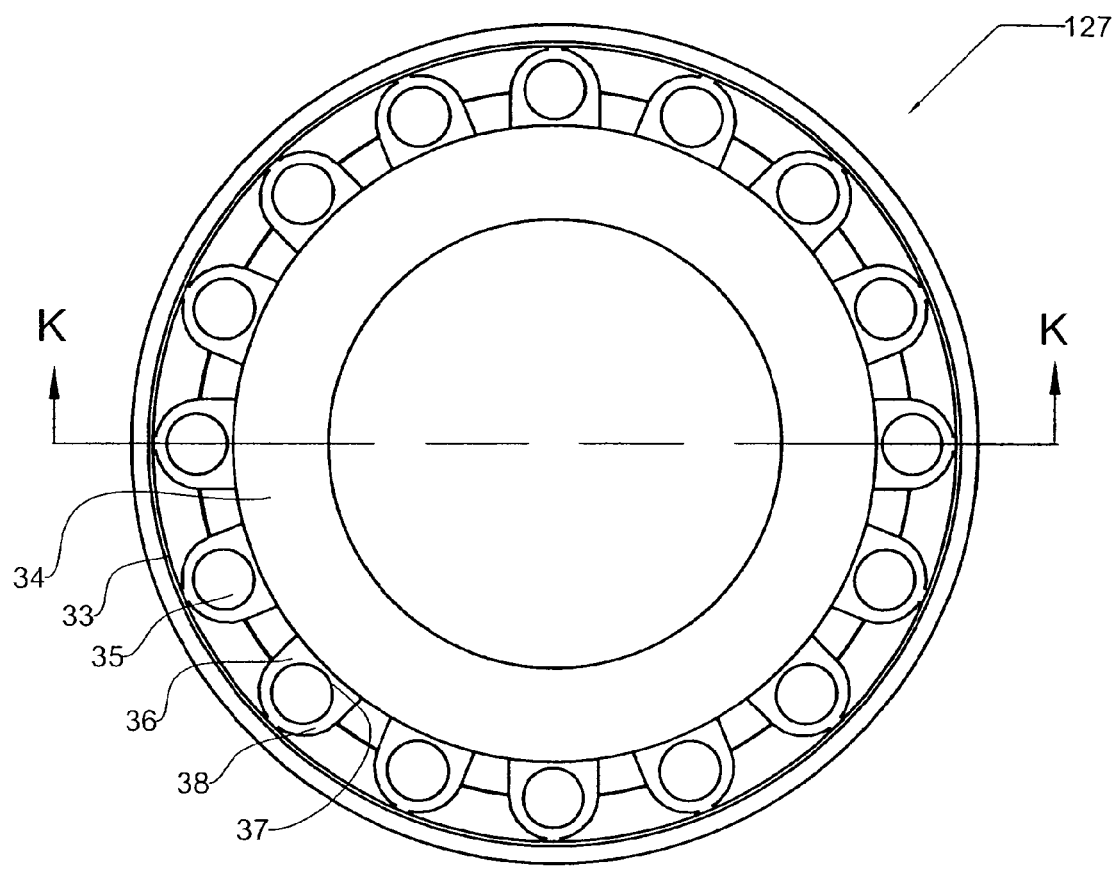
Figures 1, 2K:
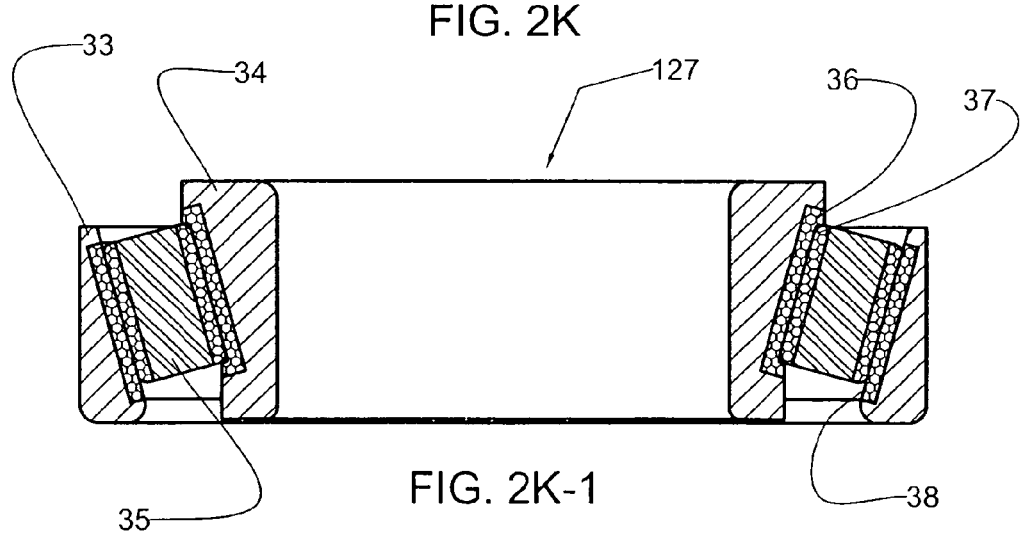

FIGS. 2K and 2K-1 depict a cylindrical roller bearing assembly 127. The bearing assembly 127 includes inner race 34, outer race 33 and cylindrical bearing member 35. Cylindrical bearing member 35 includes a substrate and an outer superhard articulation surface 37. The bearing member 35 turns in a sleeve 36 with a superhard articulation surface. The sleeve and bearing member are held buy a retainer 38.

Figures 1, 2, 2L:
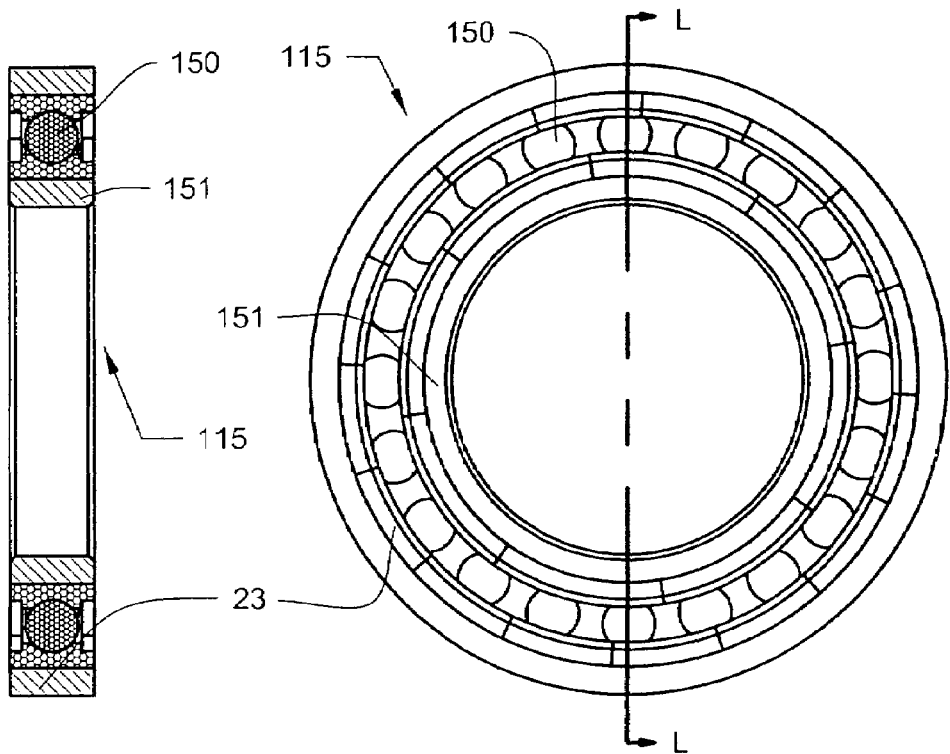

FIGS. 2L-1 and 2L-2 depict a radial ball bearing assembly 115 with radial tetragonal segmented bearing races. Radial tetragonal segmented bearing surfaces 23 are shown having a superhard bearing surface. Inner race 151 is depicted and ball bearings 150 are shown. Either the ball bearing elements or the tetragonal segmented bearing surfaces or both may be made from diamond or other superhard materials. Use of individual bearing surfaces such as tetragonal segments provides an advantage from a manufacturing standpoint. In some manufacturing environments, it may be easier and cheaper to make individual PDC or superhard segments and later assemble them on an appropriate substrate as the bearing surface of a race, rather than making the entire bearing surface of the race as a unitary PDC or superhard component.

Figures 1, 2, 2M:
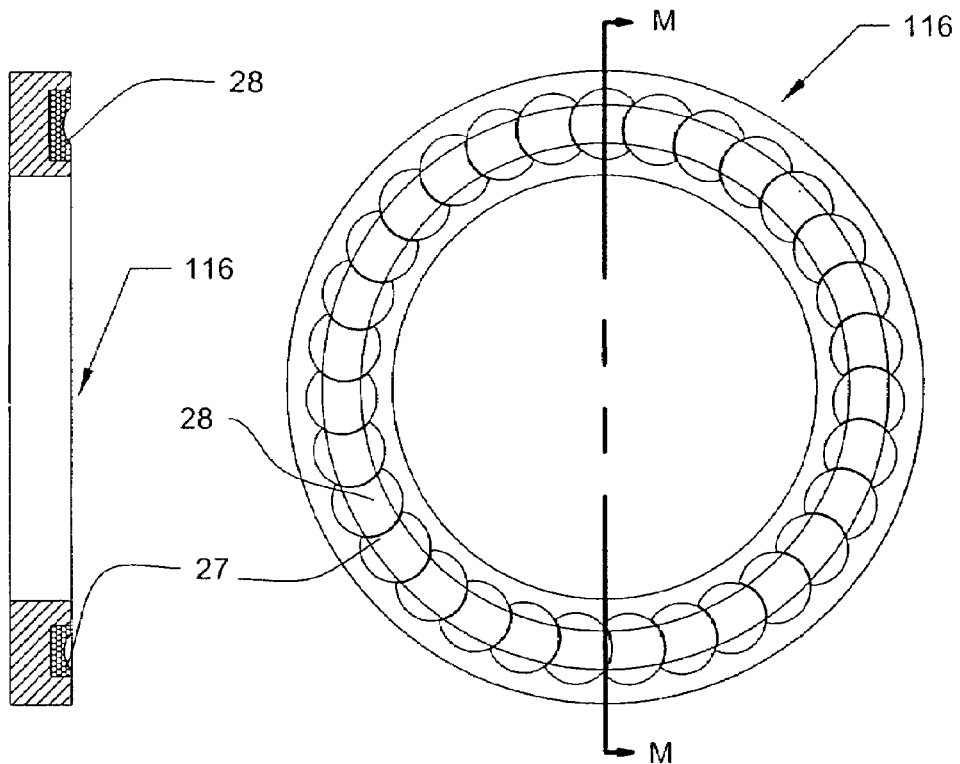

FIGS. 2M-1 and 2M-2 depict a thrust bearing race 116 with a segmented diamond other superhard material bearing surface present in round nested inlays 28 (circular segments) on a substrate. The nested inlays 27 are formed to each have an arcuate depression 27 therein. Each of the inlays may be made as a polycrystalline diamond compact having a volume of diamond on its own substrate. The inlays may be installed on a substrate in nested juxtaposition. Alternatively, the inlays may be made from a continuous phase of material. For some bearing applications and some manufacturing environments, it may be easier and cheaper to manufacture inlays and assemble them on a substrate than to form the entire bearing surface as a unitary component.

FIGS. 2P and 2P-1 depict an individual bearing segment that may be used in an application such as that depicted in the previous figures. The segment 119 includes a volume of diamond 123*c* or other superhard material on a substrate 121, although the segment 119 could be formed from a continuous phase of superhard material. The geometry of the segment 119 depicted is generally circular with a concave arcuate section 122 to accommodate nesting with other segments and present a continuous bearing surface 120. The sides of the segment 119 as shown by numerals 123*a* and 123*b* are generally parallel but are not square with the bearing surface or bottom 123*d* or the segment 119 to provide a better fit and grip with adjacent segments in a bearing or race.

FIGS. 2Q and 2Q-1 depict a thrust bearing 124 with continuous diamond 24 or other superhard material bonded to a substrate 25.

FIGS. 2R-1 and 2R-2 depict a thrust bearing 125 with angular inlaid segments 29 using diamond or other superhard material. Each angular inlayed race bearing segment or element 29 is juxtaposed to adjacent bearing elements and fixed suitably, such as by brazing to the thrust bearing substrate 31. Each segment 29 may be a continuous phase of superhard material or it may include a layer of superhard material 32 on a substrate 30, such as a polycrystalline diamond compact.

Figures 1, 2, 2T:
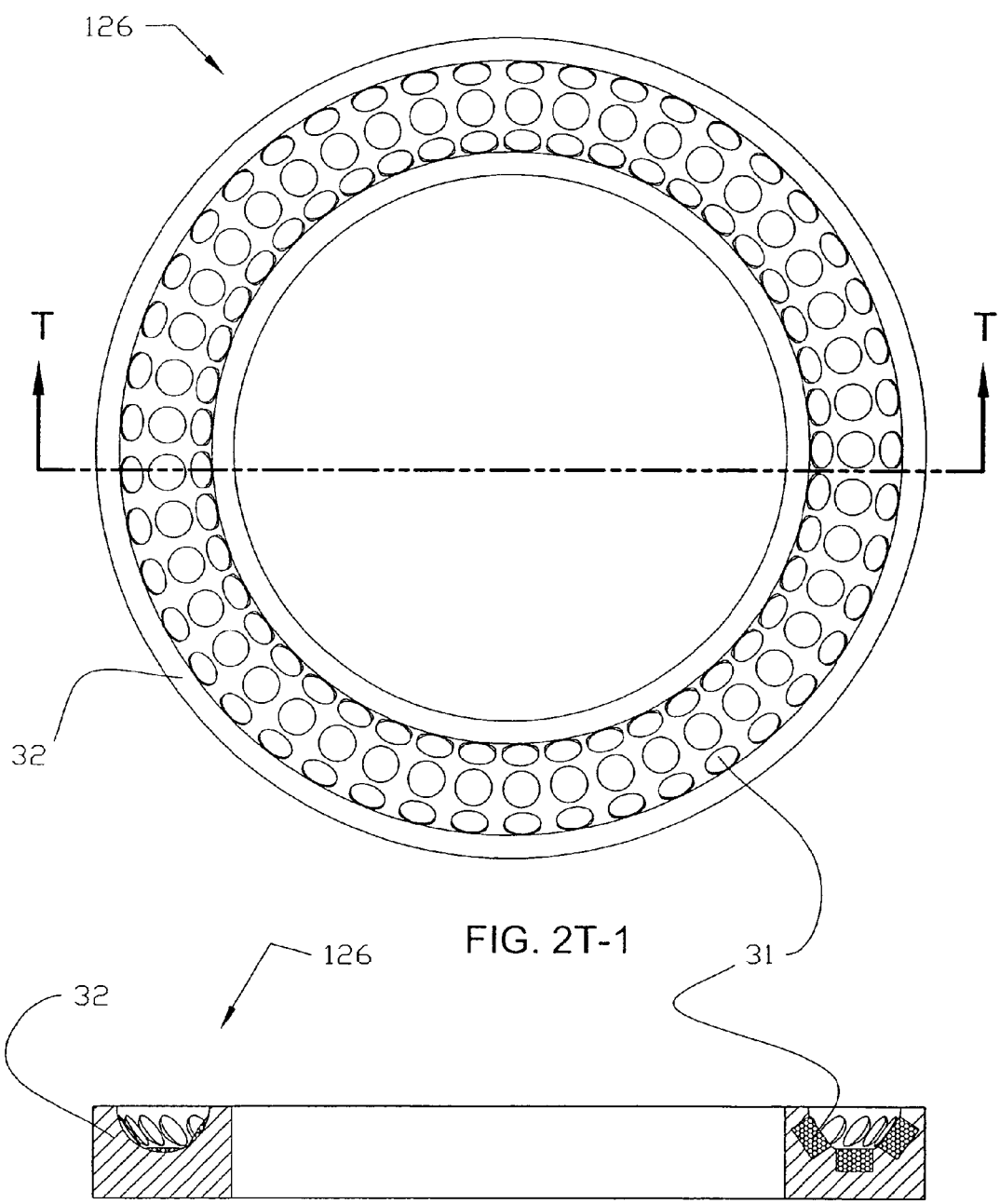

FIGS. 2S-1 and 2S-2 depict a front and section view of a single angular segment 29 for use in the bearing of FIGS. 2*t* and 2*u* or other applications. The bearing segment 29 has angular sides 29*a* and 29*b* for inlaying on a substrate in juxtaposition with other bearing segments. The top 29*c* and bottom 29*d* edges of the bearing segment 29 are depicted as being arcuate but may be configured otherwise.

The segment 29 may be a continuous phase of superhard material or it may include a volume of superhard material 29*e* on a substrate 29*f* such as in a polycrystalline diamond compact.

FIGS. 2T-1 and 2T-2 depict a thrust bearing race 126 with multiple segmented bearing elements 31 inlayed into the appropriate thrust bearing race substrate 32. The bearing elements 31 may be circular, oval, or any other desired shape. The bearing elements may be polycrystalline diamond compacts, continuous phase polycrystalline diamond, other continuous phase superhard material, or superhard material on a substrate. The bearing elements 31 may be affixed to the substrate 32 by an appropriate technique, such as brazing, bonding, cementing, pressing, welding, mechanical fit, mechanical attachment or otherwise. The bearing elements 31 may be directly adjacent each other to provide a continuous superhard bearing surface, or they may be spaced apart so that veins of substrate 31 exist between them.

One purpose of this invention to incorporate diamond and or other super hard materials onto the bearing surfaces of the rolling elements and or races in various geometries in order to improve the durability, reliability, and precision of mechanical devices incorporating bearing elements. In addition, implementation of the inventive concepts should diminish susceptibility to degradation of mechanical function of bearings and/or races in corrosive environments, increase resistance to wear, diminish the requirements for complex lubricating systems as part of bearing units and increase resistance to a high loads and to impact loads.

Bearings made using the inventive concepts and preferred materials may be made with excellent thermal and dimensional stability and excellent corrosion resistance, and having a low coefficient of friction and extreme resistance to wear and dimensional degradation.

The invented structures and methods may be applied to an infinite variety of bearings and races and bearing and articulation surfaces in any field. Some additional examples of products that may be made according to the inventive concepts include radial ball bearings, radial roller bearings, ball thrust bearings, roller thrust bearings, bushings, sleeves, races, and any other articulation surface.

Some embodiments of the invention that include a diamond table on one of the articulation surfaces, the diamond table will typically be from submicron thickness to about 3000 microns thick or more. Some embodiments of the invention utilize a solid polycrystalline diamond component, such as a solid polycrystalline diamond ball or a solid polycrystalline diamond socket. In those cases, the diamond table dimension will equal the component dimension.

For ball and socket bearing components using a polycrystalline diamond compact with a substrate, it is expected that for ease of manufacturing, the polycrystalline diamond table will be from less than about 5 microns thick to more than about 2 millimeters thick in the most preferred embodiments of the invention. Other diamond bearing component surfaces and other superhard bearing surfaces might have thickness in the range of less than about 1 micron to more than about 100 microns, or solid polycrystalline diamond components could be used as described above.

In various embodiments of the invention, the geometry and dimensions of the bearing surface of the component may be designed to meet the needs of a particular application and may differ from that which is described herein.

B. Attachment of Diamond in the Preferred Bearing component

1. Nature of the Diamond-Substrate Interface

In the preferred embodiment of the invention, a polycrystalline diamond compact provides unique chemical bonding and mechanical grip between the articulation surface and the substrate material.

Some preferred bearing component structures of the invention uses a polycrystalline diamond compact for at least one of the bearing and race components. A bearing or race component which utilizes polycrystalline diamond compact will have a chemical bond between substrate material and the diamond crystals. The result of this structure is an extremely strong bond between the substrate and the diamond table.

A method by which PDC is preferably manufactured is described later in this document. Briefly, it involves sintering diamond crystals to each other, and to a substrate under high pressure and high temperature. In the most preferred embodiment, the finished part will have residual stresses at the diamond to substrate interface that do not exceed the tensile strength of the substrate, the diamond or the diamond to substrate interface.

Figure 4A:
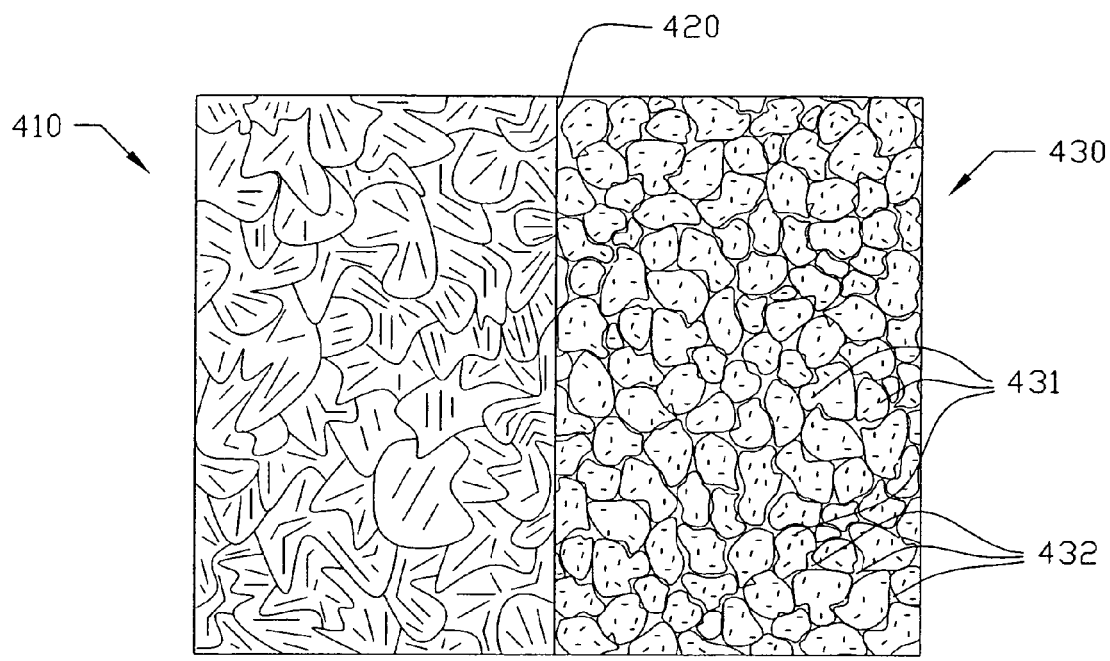
FIG. 4A depicts a quantity of diamond feedstock adjacent to a metal alloy substrate prior to sintering of the diamond feedstock and the substrate to create a polycrystalline diamond compact.
Figure 4B:
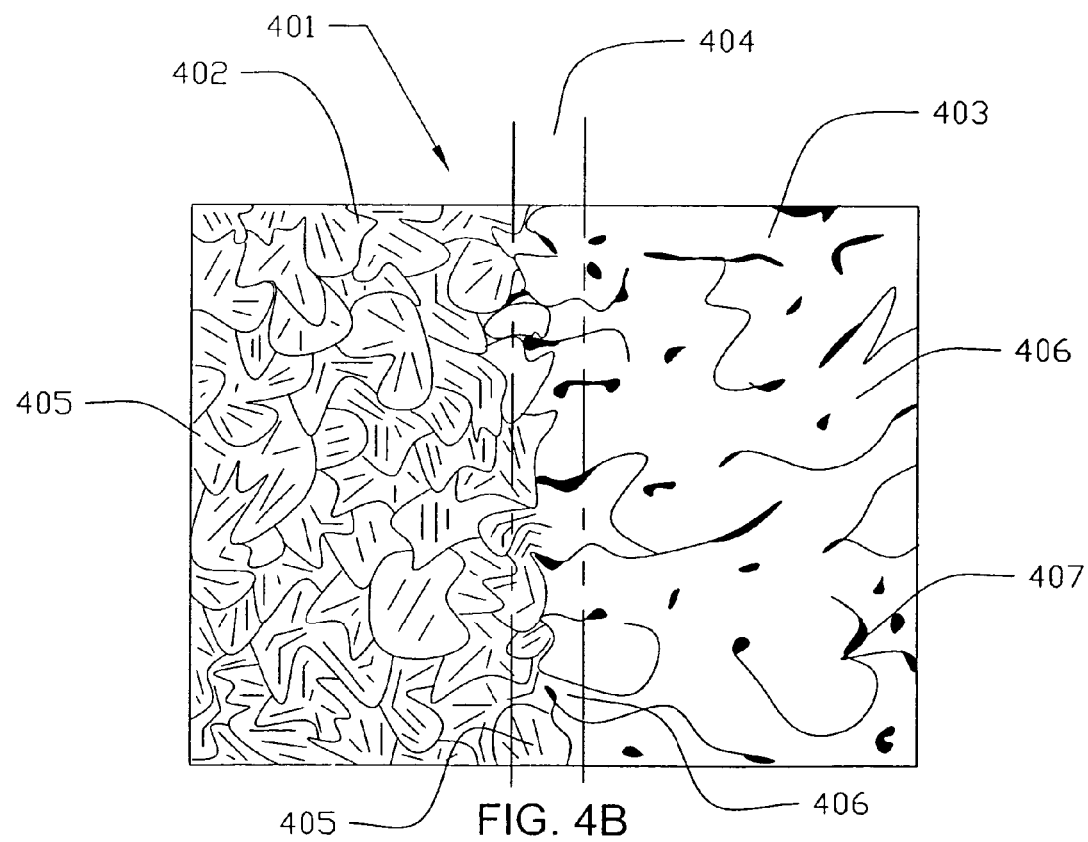
FIG. 4B depicts a sintered polycrystalline diamond compact in which the diamond table, the substrate, and the transition zone between the diamond table and the substrate are shown.
Figure 4B:
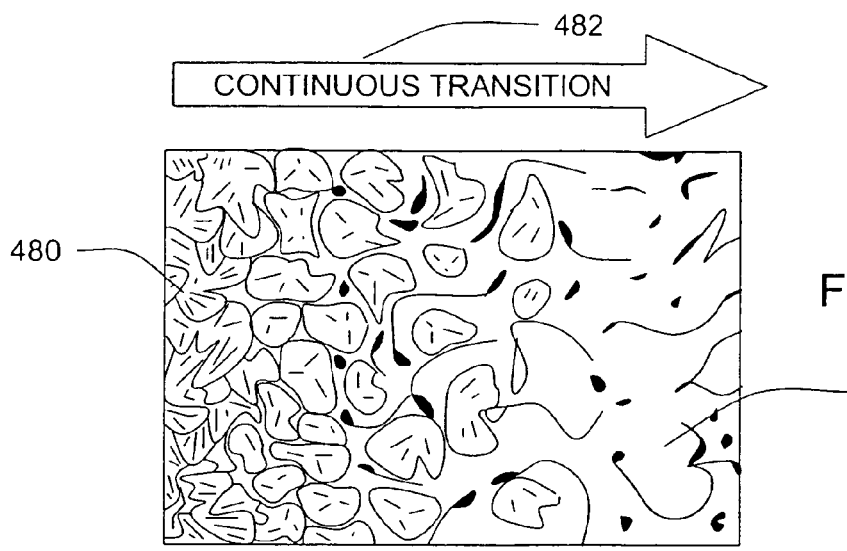

FIGS. 4A and 4B illustrate the physical and chemical processes involved manufacturing polycrystalline diamond compacts.

In FIG. 4A, a quantity of diamond feedstock 430 (such as diamond powder or crystals) is placed adjacent to a metal-containing substrate 410 prior to sintering. In the region of the diamond feedstock 430, individual diamond crystals 431 may be seen, and between the individual diamond crystals 431 there are interstitial spaces 432. If desired, a quantity of solvent-catalyst metal may be placed into the interstitial spaces 432.

The substrate 410 may be a suitable pure metal or alloy, 2 or more metals or alloys, a composite structure of metals and alloys, or a cemented carbide containing a suitable metal or alloy such as a cementing agent such as cobalt-cemented tungsten carbide. Preferably the substrate will be a metal with high tensile strength. When the residual stresses in the finished part at the diamond to substrate interface that do not exceed the tensile strength of the substrate, the diamond or the diamond to substrate interface, the result is a very strong and durable component. Contributing to this is the use of a substrate that will expand during the sintering process and contract at the conclusion of sintering to yield a substrate in the finished part that is dimensionally 0.01% to 1.0% smaller than it was prior to sintering.

The illustration shows the individual diamond crystals and the contiguous metal crystals in the metal substrate. The interface 420 between diamond powder and substrate material is a critical region where bonding of the diamond table to the substrate must occur. In some embodiments of the invention, a boundary layer of a third material different than the diamond and the substrate is placed at the interface 420. This interface boundary layer material, when present, may serve several functions including, but not limited to, enhancing the bond of the diamond table to the substrate, and mitigation of the residual stress field at the diamond-substrate interface.

Once diamond powder or crystals and substrate are assembled as shown in FIG. 4A, the assembly is subjected to high pressure and high temperature as described later herein in order to cause bonding of diamond crystals to diamond crystals and to the substrate. The resulting structure of sintered polycrystalline diamond table bonded to a substrate is called a polycrystalline diamond compact (PDC). A compact, as the term is used herein, is a composite structure of two different materials, such as diamond crystals, and a substrate metal. The analogous structure incorporating cubic boron nitride crystals in the sintering process instead of diamond crystals is called polycrystalline cubic boron nitride compact (PCBNC). Many of the processes described herein for the fabrication and finishing of PDC structures and parts work in a similar fashion for PCBNC. In some embodiments of the invention, PCBNC may be substituted for PDC.

FIG. 4B depicts a polycrystalline diamond compact 401 after the high pressure and high temperature sintering of diamond feedstock to a substrate. Within the PDC structure, there is an identifiable volume of substrate 402, an identifiable volume of diamond table 403, and a transition zone 404 between diamond table and substrate containing diamond crystals and substrate material. Crystalline grains of substrate material 405 and sintered or bonded crystals of diamond 406 are depicted.

On casual examination, the finished compact of FIG. 4B will appear to consist of a solid table of diamond 403 attached to the substrate 402 with a discrete boundary. On very close examination, however, a transition zone 404 between diamond table 403 and substrate 402 can be characterized. This zone represents a gradient interface between diamond table and substrate with a gradual transition of ratios between diamond content and metal content. The composition of the transition zone will range from low diamond content at the substrate side to nearly pure diamond at the nearly pure diamond at the sintered diamond side. The presence of such a transition zone distributes the stress between the diamond table and the substrate.

In the transition zone where diamond crystals and substrate metal are intermingled, chemical bonds are formed between the diamond and metal. From the transition zone 404 into the diamond table 403, the metal concentration diminishes and is limited to solvent-catalyst metal that fills the three-dimensional vein-like structure of interstitial voids or openings 407 within the sintered diamond table structure 403. The solvent-catalyst metal found in the voids or openings 407 may have been swept up from the substrate during sintering or may have been solvent-catalyst metal added to the diamond feedstock before sintering.

During the sintering process, there are three types of chemical bonds that are created: diamond-to-diamond bonds, diamond-to-metal bonds, and metal-to-metal bonds. In the diamond table, there are diamond-to-diamond bonds ($sp_3$ carbon bonds) created when diamond particles partially solvate in the solvate-catalyst metal and then are bonded together. In the substrate and in the diamond table, there are metal-to-metal bonds created by the high pressure and high temperature sintering process. And in the transition zone, diamond-to-metal bonds are created between diamond and solvent-catalyst metal.

The combination of these various chemical bonds and the mechanical grip exerted by solvent-catalyst metal in the diamond table such as in the interstitial spaces of the diamond structure diamond table provide extraordinarily high bond strength between the diamond table and the substrate. Interstitial spaces are present in the diamond structure and those spaces typically are filled with solvent-catalyst metal, forming veins of solvent-catalyst metal within the polycrystalline diamond structure. This bonding structure contributes to the extraordinary fracture toughness of the compact, and the veins of metal within the diamond table act as energy sinks halting propagation of incipient cracks within the diamond structure. The transition zone and metal vein structure provide the compact with a gradient of material properties between those of the diamond table and those of substrate material, further contributing to the extreme toughness of the compact. The transition zone can also be called an interface, a gradient transition zone, a composition gradient zone, or a composition gradient, depending on its characteristics. The transition zone distributes diamond/substrate stress over the thickness of the zone, reducing zone high stress of a distinct linear interface. The subject residual stress is created as pressure and temperature are reduced at the conclusion of the high pressure/high temperature sintering process due to the difference in pressure and thermal expansive properties of the diamond and substrate materials.

The diamond sintering process occurs under conditions of extremely high pressure and high temperature. According to the inventors' best experimental and theoretical understanding, the diamond sintering process progresses through the following sequence of events. A pressure cell containing feedstock of unbonded diamond powder or crystals (diamond feedstock) and a substrate is heated to a temperature above the melting point of the binder metal of the substrate 410 and flows or sweeps into the interstitial voids 407 between the adjacent diamond crystals 406. It diffuses under the driving forces of the pressure differential to fill the voids as well as being pulled in by the surface energy or capillary action of the large surface area of the diamond crystals 406. As the temperature continues to rise, carbon atoms from the surface of diamond crystals dissolve into this interstitial molten metal, forming a carbon solution.

At the proper threshold of temperature and pressure, diamond becomes the thermodynamically favored crystalline allotrope of carbon. As the solution becomes super saturated with respect to $C_d$ (carbon diamond), carbon from this solution begins to crystallize as diamond onto the surfaces of diamond crystals bonding adjacent diamond crystals together with diamond-diamond bonds into a sintered polycrystalline diamond structure 406. The interstitial metal fills the remaining void space forming the vein-like lattice structure 407 within the diamond table by capillary forces and pressure driving forces. Because of the crucial role that the interstitial metal plays in forming a solution of carbon atoms and reducing the activation energy for the solution/precipitation reaction in which the polycrystalline diamond structure is formed, the metal is referred to as a solvent-catalyst metal.

FIG. 4BB depicts a polycrystalline diamond compact having both substrate metal 480 and diamond 481, but in which there is a continuous concentration gradient or transition 482 from substrate metal to diamond. In such a compact, the gradient transition zone may be the entire compact or a portion of it.

In some embodiments of the invention, a quantity of solvent-catalyst metal may be combined with the diamond feedstock prior to sintering. This is found to be necessary when forming thick PCD tables, solid PDC structures, or when using multimodal fine diamond where there is little residual free space within the diamond powder. In each of these cases, there is insufficient ingress of solvent-catalyst metal via the sweep or diffusion mechanism to adequately mediate the sintering process as a solvent-catalyst. The metal may be added by direct addition of powder, or by generation of metal powder in situ with an attritor mill or by the well-known method of chemical reduction of metal salts deposited on diamond crystals. Added metal may constitute any amount from less than 1% by mass, to greater than 35%. This added metal may consist of the same metal or alloy as is found in the substrate, or may be a different metal or alloy selected because of its material and mechanical properties. Example ratios of diamond feedstock to solvent-catalyst metal prior to sintering include mass ratios of 70:30, 85:15, 90:10, and 95:15.

When sintering diamond on a substrate with an interface boundary layer, no solvent-catalyst metal from the substrate is available to sweep into the diamond table and participate in the sintering process. In this case, the boundary layer material, if composed of a suitable material, metal or alloy that can function as a solvent-catalyst, may serve as the sweep material mediating the diamond sintering process. In other cases where the desired boundary material cannot serve as a solvent-catalyst, a suitable amount of solvent-catalyst metal powder as described herein is added to the diamond crystal feed stock as described above. In the absence of a substrate metal source, the solvent-catalyst metal for the diamond sintering process must be supplied entirely from the added metal powder. The boundary material bonds chemically to the substrate material, and bonds chemically to the diamond table and/or the added solvent-catalyst metal in the diamond table. The remainder of the sintering and fabrication process are the same as with the conventional solvent-catalyst sweep sintering and fabrication process.

For the sake of simplicity and clarity in this patent, the substrate, transition zone, and diamond table have been discussed as distinct layers. However, it is important to realize that the finished sintered object consists of a composite structure characterized by a continuous gradient transition from substrate material to diamond table rather than as distinct layers with clear and discrete boundaries, hence the term "compact".

In addition to the sintering processes described above, diamond parts suitable for use as bearings for such applications may also be fabricated as solid polycrystalline diamond structures without a substrate. These are formed by placing the diamond powder combined with a suitable amount of added solvent-catalyst metal powder as described above in a refractory metal can (typically Ta, Nb, Zr, or Mo) with a shape approximating the shape of the final part desired. This assembly is then taken through the sintering process. However, in the absence of a substrate metal source, the solvent-catalyst metal for the diamond sintering process must be supplied entirely from the added metal powder. After processing in the high pressure high temperature press and finishing, bearings thus formed may be used as is, or bonded to metal substrates to function as total bearing component articulations.

Sintering is the preferred method of creating a diamond table with a strong and durable bond to a substrate material. Other methods of producing a diamond table bonded to a substrate are possible. At present, these typically are not as strong or durable as those fabricated with the sintering process. It is also possible to use these methods to form diamond structures directly onto substrates suitable for use as bearing component bearings. A table of polycrystalline diamond either with or without a substrate may be manufactured and later attached to a bearing component in a location such that it will form a bearing surface. The attachment could be performed with any suitable method, including welding, brazing, sintering, diffusion welding, diffusion bonding, inertial welding, adhesive bonding, or the use of fasteners such as screws, bolts, or rivets. In the case of attaching a diamond table without a substrate to another object, the use of such methods as brazing, diffusion welding/bonding or inertia welding may be most appropriate.

2. Alternative Methods for Creating a Diamond Bearing Surface

Although high pressure/high temperature sintering is the preferred method for creating a diamond bearing surface, other methods for producing a volume of diamond may be employed as well. For example, either chemical vapor deposition (CVD), or physical vapor deposition (PVD) processes may be used. CVD produces a diamond layer by thermally cracking an organic molecule and depositing carbon radicals on a substrate. PVD produces a diamond layer by electrically causing carbon radicals to be ejected from a source material and to deposit on a substrate where they build a diamond crystal structure.

The CVD and PVD processes have some advantages over sintering. Sintering is performed in large, expensive presses at high pressure (such as 40-68 kilobars) and at high temperatures (such as 1200 to 1500 degrees Celsius). It is difficult to achieve and maintain desired component shape using a sintering process because of deformation and flow of high pressure mediums used and possible deformation of substrate materials.

In contrast, CVD and PVD take place at atmospheric pressure or lower, so there no need for a pressure medium and there is no deformation of substrates.

Another disadvantage of sintering is that it is difficult to achieve some geometries in a sintered polycrystalline diamond compact. When CVD or PVD are used, however, the gas phase used for carbon radical deposition can completely conform to the shape of the object being coated, making it easy to achieve a desired non-planar shape.

Another potential disadvantage of sintering polycrystalline diamond compacts is that the finished component will tend to have large residual stresses caused by differences in the coefficient of thermal expansion and modulus between the diamond and the substrate. While residual stresses can be used to improve strength of a part, they can also be disadvantageous. When CVD or PVD is used, residual stresses can be minimized because CVD and PVD processes do not involve a significant pressure transition (such from about 40-68 Kbar to atmospheric pressure in high pressure and high temperature sintering) during manufacturing.

Another potential disadvantage of sintering polycrystalline diamond compacts is that few substrates have been found that are suitable for sintering. In the prior art, the typical substrate used was tungsten carbide. In the invention, non-planar components have been made using other substrates. When CVD or PVD are used, however, synthetic diamond can be placed on many substrates, including titanium, most carbides, silicon, molybdenum and others. This is because the temperature and pressure of the CVD and PVD coating processes are low enough that differences in coefficient of thermal expansion and modulus between diamond and the substrate are not as critical as they are in a high temperature and high pressure sintering process.

A further difficulty in manufacturing sintered polycrystalline diamond compacts is that as the size of the part to be manufactured increases, the size of the press must increase as well. Sintering of diamond will only take place at certain pressures and temperatures, such as those described herein. In order to manufacture larger sintered polycrystalline diamond compacts, ram pressure of the press (tonnage) and size of tooling (such as dies and anvils) must be increased in order to achieve the necessary pressure for sintering to take place. But increasing the size and capacity of a press is more difficult than simply increasing the dimensions of its components. There may be a practical physical size constraints on press size due to the manufacturing process used to produce press tooling.

Tooling for a press is typically made from cemented tungsten carbide. In order to make tooling, the cemented tungsten carbide is sintered in a vacuum furnace followed by pressing in a hot isosatic press ("HIP") apparatus. Hipping must be performed in a manner that maintains uniform temperature throughout the tungsten carbide in order to achieve uniform physical qualities and quality. These requirements impose a practical limit on the size tooling that can be produced for a press that is useful for sintering polycrystalline diamond compacts. The limit on the size tooling that can be produced also limits the size press that can be produced.

CVD and PVD manufacturing apparatuses may be scaled up in size with few limitations, allowing them to produce polycrystalline diamond compacts of almost any desired size.

CVD and PVD processes are also advantageous because they permit precise control of the thickness and uniformity of the diamond coating to be applied to a substrate. Temperature is adjusted within the range of 500 to 1000 degrees Celsius, and pressure is adjusted in a range of less than 1 atmosphere to achieve desired diamond coating thickness.

Another advantage of CVD and PVD processes is that they allow the manufacturing process to be monitored as it progresses. A CVD or PVD reactor can be opened before manufacture of a part is completed so that the thickness and quality of the diamond coating being applied to the part may be determined. From the thickness of the diamond coating that has already been applied, time to completion of manufacture can be calculated. Alternatively, if the coating is not of desired quality, the manufacturing processes may be aborted in order to save time and money.

In contrast, sintering of polycrystalline diamond compacts is performed as a batch process that cannot be interrupted, and progress of sintering cannot be monitored. The pressing process must be run to completion and the part may only be examined afterward.

CVD is performed in an apparatus called a reactor. A basic CVD reactor includes four components. The first component of the reactor is one or more gas inlets. Gas inlets may be chosen based on whether gases are premixed before introduction to the chamber or whether the gases are allowed to mix for the first time in the chamber. The second component of the reactor is one or more power sources for the generation of thermal energy. A power source is needed to heat the gases in the chamber. A second power source may be used to heat the substrate material uniformly in order to achieve a uniform coating of diamond on the substrate. The third component of the reactor is a stage or platform on which a substrate is placed. The substrate will be coated with diamond during the CVD process. Stages used include a fixed stage, a translating stage, a rotating stage and a vibratory stage. An appropriate stage must be chosen to achieved desired diamond coating quality and uniformity. The fourth component of the reactor is an exit port for removing exhaust gas from the chamber. After gas has reacted with the substrate, it must be removed from the chamber as quickly as possible so that it does not participate in other reactions, which would be deleterious to the diamond coating.

CVD reactors are classified according to the power source used. The power source is chosen to create the desired species necessary to carry out diamond thin film deposition. Some CVD reactor types include plasma-assisted microwave, hot filament, electron beam, single, double or multiple laser beam, arc jet and DC discharge. These reactors differ in the way they impart thermal energy to the gas species and in their efficiency in breaking gases down to the species necessary for deposition of diamond. It is possible to have an array of lasers to perform local heating inside a high pressure cell. Alternatively, an array of optical fibers could be used to deliver light into the cell.

The basic process by which CVD reactors work is as follows. A substrate is placed into the reactor chamber. Reactants are introduced to the chamber via one or more gas inlets. For diamond CVD, methane ($CH_4$) and hydrogen ($H_2$) gases are preferably brought into the chamber in premixed form. Instead of methane, any carbon-bearing gas in which the carbon has $sp_3$ bonding may be used. Other gases may be added to the gas stream in order to control quality of the diamond film, deposition temperature, gain structure and growth rate. These include oxygen, carbon dioxide, argon, halogens and others.

The gas pressure in the chamber is preferably maintained at about 100 torr. Flow rates for the gases through the chamber are preferably about 10 standard cubic centimeters per minute for methane and about 100 standard cubic centimeters per minute for hydrogen. The composition of the gas phase in the chamber is preferably in the range of 90-99.5% hydrogen and 0.5-10% methane.

When the gases are introduced into the chamber, they are heated. Heating may be accomplished by many methods. In a plasma-assisted process, the gases are heated by passing them through a plasma. Otherwise, the gases may be passed over a series of wires such as those found in a hot filament reactor.

Heating the methane and hydrogen will break them down into various free radicals. Through a complicated mixture of reactions, carbon is deposited on the substrate and joins with other carbon to form crystalline diamond by $sp_3$ bonding. The atomic hydrogen in the chamber reacts with and removes hydrogen atoms from methyl radicals attached to the substrate surface in order to create molecular hydrogen, leaving a clear solid surface for further deposition of free radicals.

If the substrate surface promotes the formation of $sp_2$ carbon bonds, or if the gas composition, flow rates, substrate temperature or other variables are incorrect, then graphite rather than diamond will grow on the substrate.

There are many similarities between CVD reactors and processes and PVD reactors and processes. PVD reactors differ from CVD reactors in the way that they generate the deposition species and in the physical characteristics of the deposition species. In a PVD reactor, a plate of source material is used as a thermal source, rather than having a separate thermal source as in CVD reactors. A PVD reactor generates electrical bias across a plate of source material in order to generate and eject carbon radicals from the source material. The reactor bombards the source material with high energy ions. When the high energy ions collide with source material, they cause ejection of the desired carbon radicals from the source material. The carbon radicals are ejected radially from the source material into the chamber. The carbon radicals then deposit themselves onto whatever is in their path, including the stage, the reactor itself, and the substrate.

Figure 4C:
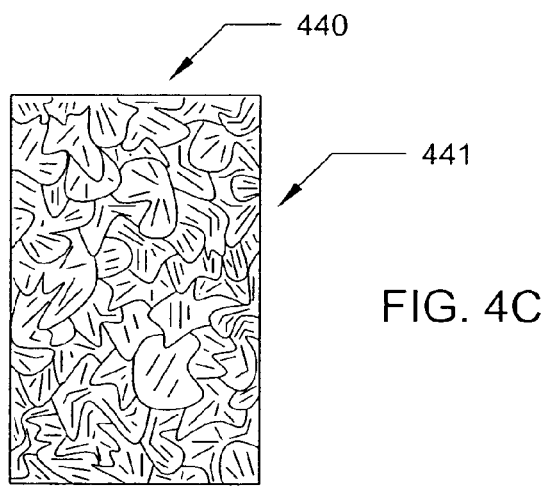
FIG. 4C depicts a substrate prior to use of a CVD or PVD process for form a volume of diamond on the substrate.
Figure 4D:
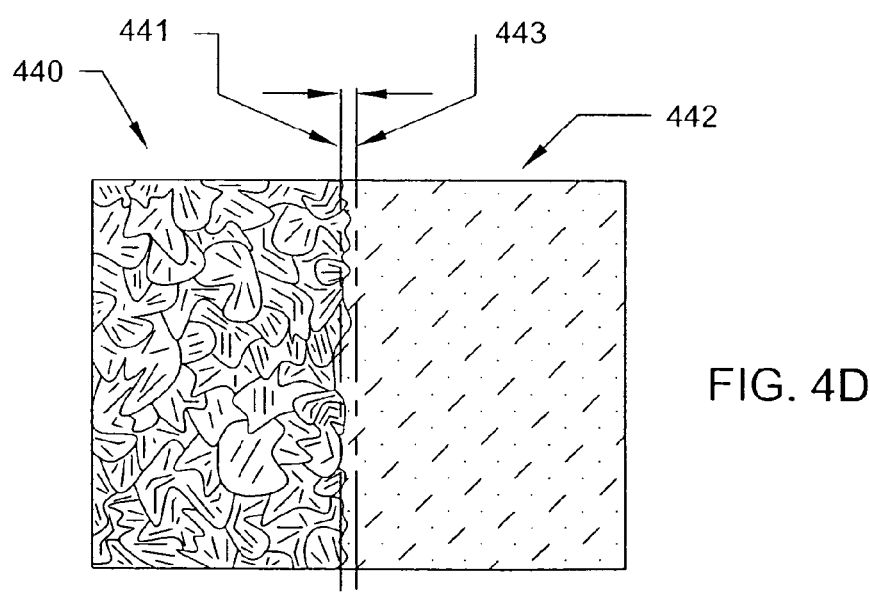
FIG. 4D depicts a diamond compact formed by a CVD or PVD process.

Referring to FIG. 4C, a substrate 440 of appropriate material is depicted having a deposition face 441 on which diamond may be deposited by a CVD or PVD process. FIG. 4D depicts the substrate 440 and the deposition face 441 on which a volume of diamond 442 has been deposited by CVD or PVD processes. A small transition zone 443 is present in which both diamond and substrate are located. In comparison to FIG. 4B, it can be seen that the CVD or PVD diamond deposited on a substrate lacks the more extensive gradient transition zone of sintered polycrystalline diamond compacts because there is no sweep of solvent-catalyst metal through the diamond table in a CVD or PVD process.

Both CVD and PVD processes achieve diamond deposition by line of sight. Means (such as vibration and rotation) are provided for exposing all desired surfaces for diamond deposition. If a vibratory stage is to be used, the bearing surface will vibrate up and down with the stage and thereby present all bearing surfaces to the free radical source.

There are several methods, which may be implemented in order to coat cylindrical objects with diamond using CVD or PVD processes. If a plasma assisted microwave process is to be used to achieve diamond deposition, then the object to receive the diamond must be directly under the plasma in order to achieve the highest quality and most uniform coating of diamond. A rotating or translational stage may be used to present every aspect of the bearing surface to the plasma for diamond coating. As the stage rotates or translates, all portions of the bearing surface may be brought directly under the plasma for coating in such a way to achieve sufficiently uniform coating.

If a hot filament CVD process is used, then the bearing surface should be placed on a stationary stage. Wires or filaments (typically tungsten) are strung over the stage so that their coverage includes the bearing surface to be coated. The distance between the filaments and the bearing surface and the distance between the filaments themselves may be chosen to achieve a uniform coating of diamond directly under the filaments.

Diamond bearing surfaces can be manufactured by CVD and PVD process either by coating a substrate with diamond or by creating a free standing volume of diamond, which is later mounted for use. A free standing volume of diamond may be created by CVD and PVD processes in a two-step operation. First, a thick film of diamond is deposited on a suitable substrate, such as silicon, molybdenum, tungsten or others. Second, the diamond film is released from the substrate.

As desired, segments of diamond film may be cut away, such as by use of a Q-switched YAG laser. Although diamond is transparent to a YAG laser, there is usually a sufficient amount of $sp_2$ bonded carbon (as found in graphite) to allow cutting to take place. If not, then a line may be drawn on the diamond film using a carbon-based ink. The line should be sufficient to permit cutting to start, and once started, cutting will proceed slowly.

After an appropriately-sized piece of diamond has been cut from a diamond film, it can be attached to a desired object in order to serve as a bearing surface. For example, the diamond may be attached to a substrate by welding, diffusion bonding, adhesion bonding, mechanical fixation or high pressure and high temperature bonding in a press.

Although CVD and PVD diamond on a substrate do not exhibit a gradient transition zone that is found in sintered polycrystalline diamond compacts, CVD and PVD process can be conducted in order to incorporate metal into the diamond table. As mentioned elsewhere herein, incorporation of metal into the diamond table enhances adhesion of the diamond table to its substrate and can strengthen the polycrystalline diamond compact. Incorporation of diamond into the diamond table can be used to achieve a diamond table with a coefficient of thermal expansion and compressibility different from that of pure diamond, and consequently increasing fracture toughness of the diamond table as compared to pure diamond. Diamond has a low coefficient of thermal expansion and a low compressibility compared to metals. Therefore the presence of metal with diamond in the diamond table achieves a higher and more metal-like coefficient of thermal expansion and the average compressibility for the diamond table than for pure diamond. Consequently, residual stresses at the interface of the diamond table and the substrate are reduced, and delamination of the diamond table from the substrate is less likely.

A pure diamond crystal also has low fracture toughness. Therefore, in pure diamond, when a small crack is formed, the entire diamond component fails catastrophically. In comparison, metals have a high fracture toughness and can accommodate large cracks without catastrophic failure. Incorporation of metal into the diamond table achieves a greater fracture toughness than pure diamond. In a diamond table having interstitial spaces and metal within those interstitial spaces, if a crack forms in the diamond and propagates to an interstitial space containing metal, the crack will terminate at the metal and catastrophic failure will be avoided. Because of this characteristic, a diamond table with metal in its interstitial spaces is able to sustain much higher forces and workloads without catastrophic failure compared to pure diamond.

Diamond-diamond bonding tends to decrease as metal content in the diamond table increases. CVD and PVD processes can be conducted so that a transition zone is established. However, it is preferred for the bearing surface to be essentially pure polycrystalline diamond for low wear properties.

Generally CVD and PVD diamond is formed without large interstitial spaces filled with metal. Consequently, most PVD and CVD diamond is more brittle or has a lower fracture toughness than sintered polycrystalline diamond compacts. CVD and PVD diamond may also exhibit the maximum residual stresses possible between the diamond table and the substrate. It is possible, however, to form CVD and PVD diamond film that has metal incorporated into it with either a uniform or a functionally gradient composition.

One method for incorporating metal into a CVD or PVD diamond film it to use two different source materials in order to simultaneously deposit the two materials on a substrate in a CVD of PVD diamond production process. This method may be used regardless of whether diamond is being produced by CVD, PVD or a combination of the two.

Another method for incorporating metal into a CVD diamond film chemical vapor infiltration. This process would first create a porous layer of material, and then fill the pores by chemical vapor infiltration. The porous layer thickness should be approximately equal to the desired thickness for either the uniform or gradient layer. The size and distribution of the pores can be sued to control ultimate composition of the layer. Deposition in vapor infiltration occurs first at the interface between the porous layer and the substrate. As deposition continues, the interface along which the material is deposited moves outward from the substrate to fill pores in the porous layer. As the growth interface moves outward, the deposition temperature along the interface is maintained by moving the sample relative to a heater or by moving the heater relative to the growth interface. It is imperative that the porous region between the outside of the sample and the growth interface be maintained at a temperature that does not promote deposition of material (either the pore-filling material or undesired reaction products). Deposition in this region would close the pores prematurely and prevent infiltration and deposition of the desired material in inner pores. The result would be a substrate with open porosity an poor physical properties.

Another alternative manufacturing process that may be used to produce bearing surfaces and components of the invention involves use of energy beams, such as laser energy, to vaporize constituents in a substrate and redeposit those constituents on the substrate in a new form, such as in the form of a diamond coating. As an example, a metal, polymeric or other substrate may be obtained or produced containing carbon, carbides or other desired constituent elements. Appropriate energy, such as laser energy, may be directed at the substrate to cause constituent elements to move from within the substrate to the surface of the substrate adjacent the area of application of energy to the substrate. Continued application of energy to the concentrated constituent elements on the surface of the substrate can be used to cause vaporization of some of those constituent elements. The vaporized constituents may then be reacted with another element to change the properties and structure of the vaporized constituent elements.

Next, the vaporized and reacted constituent elements (which may be diamond) may be diffused into the surface of the substrate. A separate fabricated coating may be produced on the surface of the substrate having the same or a different chemical composition than that of the vaporized and reacted constituent elements. Alternatively, some of the changed constituent elements which were diffused into the substrate may be vaporized and reacted again and deposited as a coating on the. By this process and variations of it, appropriate coatings such as diamond, cubic boron nitride, diamond like carbon, $B_4C$, SiC, TiC, TiN, TiB, cCN, $Cr_3C_2$, and $Si_3N_4$ may be formed on a substrate.

In other manufacturing environments, high temperature laser application, electroplating, sputtering, energetic laser excited plasma deposition or other methods may be used to place a volume of diamond, diamond-like material, a hard material or a superhard material in a location in which will serve as a bearing surface.

In light of the disclosure herein, those of ordinary skill in the art will comprehend the apparatuses, materials and process conditions necessary for the formation and use of high quality diamond on a substrate using any of the manufacturing methods described herein in order to create a diamond bearing surface.

Manufacturing the Diamond Portion of Preferred Structures

This section provides information related to manufacturing some preferred structures of the invention. The principles discussed herein may be applied to manufacture nearly any type of bearing surface.

The Nature of the Problem

In areas outside of bearing components, in particular in the field of rock drilling cutters, polycrystalline diamond compacts have been used for some time. Historically those cutters have been cylindrical in shape with a planar diamond table at one end. The diamond surface of a cutter is much smaller than the bearing surface needed in most bearing components. Thus, polycrystalline diamond cutter geometry and manufacturing methods are not directly applicable to bearing components.

The particular problem posed by the manufacture of a bearing component is how to produce a polycrystalline diamond compact with a complex shape, such as concave or convex spherical, cylindrical, etc. For discussion purposes herein, manufacture of concave and convex spherical parts is primarily discussed. In the manufacture of a spherical polycrystalline diamond compact, symmetry becomes a dominant consideration in performing loading, sealing, and pressing/sintering procedures. The spherical component design requires that pressures be applied radially in making the part. During the high pressure sintering process, described in detail below, all displacements must be along a radian emanating from the center of the sphere that will be produced in order to achieve the spherical geometry. To achieve this in high temperature/high pressure pressing, an isostatic pressure field must be created. During the manufacture of such spherical parts, if there is any deviatoric stress component, it will result in distortion of the part and may render the manufactured part useless.

Special considerations that must be taken into account in making spherical polycrystalline diamond compacts are discussed below.

Modulus

Most polycrystalline diamond compacts include both a diamond table and a substrate. The material properties of the diamond and the substrate may be compatible, but the high pressure and high temperature sintering process in the formation of a polycrystalline diamond compact may result in a component with excessively high residual stresses. For example, for a polycrystalline diamond compact using tungsten carbide as the substrate, the sintered diamond has a Young's modulus of approximately 120 million p.s.i., and cobalt cemented tungsten carbide has a modulus of approximately 90 million p.s.i. Modulus refers to the slope of the curve of the stress plotted against the stress for a material. Modulus indicates the stiffness of the material. Bulk modulus refers to the ratio of isostatic strain to isostatic stress, or the unit volume reduction of a material versus the applied pressure or stress.

Because diamond and most substrate materials have such a high modulus, a very small stress or displacement of the polycrystalline diamond compact can induce very large stresses. If the stresses exceed the yield strength of either the diamond or the substrate, the component will fail. The strongest polycrystalline diamond compact is not necessarily stress free. In a polycrystalline diamond compact with optimal distribution of residual stress, more energy is required to induce a fracture than in a stress free component. Thus, the difference in modulus between the substrate and the diamond must be noted and used to design a component that will have the best strength for its application with sufficient abrasion resistance and fracture toughness.

b. Coefficient of Thermal Expansion

The extent to which diamond and its substrate differ in how they deform relative to changes in temperature also affects their mechanical compatibility. Coefficient of thermal expansion ("CTE") is a measure of the unit change of a dimension with unit change in temperature or the propensity of a material to expand under heat or to contract when cooled. As a material experiences a phase change, calculations based on CTE in the initial phase will not be applicable. It is notable that when compacts of materials with different CTE's and moduluses are used, they will stress differently at the same stress.

Polycrystalline diamond has a coefficient of thermal expansion (as above and hereafter referred to as "CTE") on the order of 24 micro inches per inch ($10^{-5}$ inches) of material per degree ($\mu in/in^\circ$ C.). In contrast, carbide has a CTE on the order of 6-8 $\mu in/in^\circ$ C. Although these values appear to be close numerically, the influence of the high modulus creates very high residual stress fields when a temperature gradient of a few hundred degrees is imposed upon the combination of substrate and diamond. The difference in coefficient of thermal expansion is less of a problem in prior art cylindrical polycrystalline diamond compacts with a planar diamond table than in the manufacture of spherical components or components with other complex geometries for bearing components. When a spherical polycrystalline diamond compact is manufactured, differences in the CTE between the diamond and the substrate can cause high residual stress with subsequent cracking and failure of the diamond table, the substrate or both at any time during or after high pressure/high temperature sintering.

c. Dilatoric and Deviatoric Stresses

The diamond and substrate assembly will experience a reduction of free volume during the sintering process. The sintering process, described in detail below, involves subjecting the substrate and diamond assembly to pressure ordinarily in the range of about 40 to about 68 kilobar. The pressure will cause volume reduction of the substrate. Some geometrical distortion of the diamond and/or the substrate may also occur. The stress that causes geometrical distortion is called deviatoric stress, and the stress that causes a change in volume is called dilatoric stress. In an isostatic system, the deviatoric stresses sum to zero and only the dilatoric stress component remains. Failure to consider all of these stress factors in designing and sintering a polycrystalline diamond component with complex geometry (such as concave and convex spherical polycrystalline diamond compacts) will likely result in failure of the process.

d. Free Volume Reduction of Diamond Feedstock

As a consequence of the physical nature of the feedstock diamond, large amounts of free volume are present unless special preparation of the feedstock is undertaken prior to sintering. It is necessary to eliminate as much of the free volume in the diamond as possible, and if the free volume present in the diamond feedstock is too great, then sintering may not occur. It is also possible to eliminate the free volume during sintering if a press with sufficient ram displacement is employed. Is important to maintain a desired uniform geometry of the diamond and substrate during any process which reduces free volume in the feedstock, or a distorted or faulty component may result.

e. Selection of Solvent-Catalyst Metal

Formation of synthetic diamond in a high temperature and high pressure press without the use of a solvent-catalyst metal is not a viable method at this time. A solvent-catalyst metal is required to achieve desired crystal formation in synthetic diamond. The solvent-catalyst metal first solvates carbon preferentially from the sharp contact points of the diamond feedstock crystals. It then recrystallizes the carbon as diamond in the interstices of the diamond matrix with diamond-diamond bonding sufficient to achieve a solid. That solid distributed over the substrate surface is referred to herein as a polycrystalline diamond table. The solvent-catalyst metal also enhances the formation of chemical bonds with substrate atoms.

A preferred method for adding the solvent-catalyst metal to diamond feedstock is by causing it to sweep from the substrate that contains solvent-catalyst metal during high pressure and high temperature sintering. Powdered solvent-catalyst metal may also be added to the diamond feedstock before sintering, particularly if thicker diamond tables are desired. An attritor method may also be used to add the solvent-catalyst metal to diamond feedstock before sintering. If too much or too little solvent-catalyst metal is used, then the resulting part may lack the desired mechanical properties, so it is important to select an amount of solvent-catalyst metal and a method for adding it to diamond feedstock that is appropriate for the particular part to be manufactured.

f. Diamond Feedstock Particle Size and Distribution

The wear characteristics of the finished diamond product are integrally linked to the size of the feedstock diamond and also to the particle distribution. Selection of the proper size(s) of diamond feedstock and particle distribution depends upon the service requirement of the specimen and also its working environment. The wear resistance of polycrystalline diamond is enhanced if smaller diamond feedstock crystals are used and a highly diamond-diamond bonded diamond table is achieved.

Although polycrystalline diamond may be made from single modal diamond feedstock, use of multi-modal feedstock increases both impact strength and wear resistance. The use of a combination of large crystal sizes and small crystal sizes of diamond feedstock together provides a part with high impact strength and wear resistance, in part because the interstitial spaces between the large diamond crystals may be filled with small diamond crystals. During sintering, the small crystals will solvate and reprecipitate in a manner that binds all of the diamond crystals into a strong and tightly bonded compact.

9. Diamond Feedstock Loading Methodology

Contamination of the diamond feedstock before or during loading will cause failure of the sintering process. Great care must be taken to ensure the cleanliness of diamond feedstock and any added solvent-catalyst metal or binder before sintering.

In order to prepare for sintering, clean diamond feedstock, substrate, and container components are prepared for loading. The diamond feedstock and the substrate are placed into a refractory metal container called a "can" which will seal its contents from outside contamination. The diamond feedstock and the substrate will remain in the can while undergoing high pressure and high temperature sintering in order to form a polycrystalline diamond compact. The can will preferably be sealed by electron beam welding at high temperature and in a vacuum.

Enough diamond aggregate (powder or grit) is loaded to account for linear shrinkage during high pressure and high temperature sintering. The method used for loading diamond feedstock into a can for sintering affects the general shape and tolerances of the final part. In particular, the packing density of the feedstock diamond throughout the can should be as uniform as possible in order to produce a good quality sintered polycrystalline diamond compact structure. In loading, bridging of diamond can be avoided by staged addition and packing.

The degree of uniformity in the density of the feedstock material after loading will affect geometry of the polycrystalline diamond compact. Loading of the feedstock diamond in a dry form versus loading diamond combined with a binder and the subsequent process applied for the removal of the binder will also affect the characteristics of the finished polycrystalline diamond compact. In order to properly pre-compact diamond for sintering, the pre-compaction pressures should be applied under isostatic conditions.

h. Selection of Substrate Material

The unique material properties of diamond and its relative differences in modulus and CTE compared to most potential substrate materials diamond make selection of an appropriate polycrystalline diamond substrate a formidable task. When the additional constraints of biocompatibility is placed on the substrate, the choice is even more difficult. Most biocompatible metals are not compatible with the material properties of synthetic diamond. A great disparity in material properties between the diamond and the substrate creates challenges successful manufacture of a polycrystalline diamond component with the needed strength and durability. Even very hard substrates appear to be soft compared to polycrystalline diamond. The substrate and the diamond must be able to withstand not only the pressure and temperature of sintering, but must be able to return to room temperature and atmospheric pressure without delaminating, cracking or otherwise failing. Further, even among those materials that are believed to be biocompatible, it is expedient to use only those which meet governmental regulatory guidelines for products such as bearing components.

Selection of substrate material also requires consideration of the intended application for the part, impact resistance and strengths required, and the amount of solvent-catalyst metal that will be incorporated into the diamond table during sintering. Substrate materials must be selected with material properties that are compatible with those of the diamond table to be formed.

i. Substrate Geometry

In the invention, it is preferred to manufacture spherical, hemispherical, partially spherical, arcuate and other complex concave and convex geometries of polycrystalline diamond compacts, which may later be cut, machined and otherwise finished to serve as heads, cup or races, other bearing component surfaces, other bearing surfaces, and other wear-resistant surfaces. Formation of such parts requires consideration of the unique geometry of the substrate. In particular, the spherical geometry of the desired finished product requires that forces applied to the substrate and diamond feedstock during sintering be along a radian emanating from the center of the sphere to be produced.

Further, it is important to consider whether to use a substrate which has a smooth surface or a surface with topographical features. Substrate surfaces may be formed with a variety of topographical features so that the diamond table is fixed to the substrate with both a chemical bond and a mechanical grip. Use of topographical features on the substrate provides a greater surface area for chemical bonds and with the mechanical grip provided by the topographical features, can result in a stronger and more durable component.

2. Preferred Materials and Manufacturing Processes

The inventors have discovered and determined materials and manufacturing processes for constructing the preferred polycrystalline diamond compacts for use in a bearing component. It is also possible to manufacture the invented bearing surfaces by methods and using materials other than those listed below.

The steps described below, such as selection of substrate material and geometry, selection of diamond feedstock, loading and sintering methods, will affect each other, so although they are listed as separate steps that must be taken to manufacture a polycrystalline diamond compact, no step is completely independent of the others, and all steps must be standardized to ensure success of the manufacturing process.

Select Substrate Material

In order to manufacture any polycrystalline diamond component, an appropriate substrate should be selected. For the manufacture of a polycrystalline diamond component to be used in a bearing component, the inventors prefer use of the substrates listed in the table below.

TABLE 2

SOME SUBSTRATES FOR BEARING APPLICATIONS

| SUBSTRATE | ALLOY NAME | REMARKS |
|---|---|---|
| Titanium | Ti6/4 (TiAlVa) ASTM F-1313 (TiNbZr) ASTM F-620 ASTM F-1580 TiMbHf Nitinol (TiNi + other) | A thin tantalum barrier is preferably placed on the titanium substrate before loading diamond feedstock. |
| Cobalt chrome | ASTM F-799 | Contains cobalt, chromium and molybdenum. Wrought product. |
| Cobalt chrome | ASTM F-90 | Contains cobalt, chromium, tungsten and nickel. |
| Cobalt chrome | ASTM F-75 | Contains cobalt, chromium and molybdenum. Cast product. |
| Cobalt chrome | ASTM F-562 | Contains cobalt, chromium, molybdenum and nickel. |
| Cobalt chrome | ASTM F-563 | Contains cobalt, chromium, molybdenum, tungsten, iron and nickel. |

TABLE 2-continued

SOME SUBSTRATES FOR BEARING APPLICATIONS

| SUBSTRATE | ALLOY NAME | REMARKS |
|---|---|---|
| Tantalum | ASTM F-560 (unalloyed) | Refractory metal. |
| Platinum | various | |
| Niobium | ASTM F-67 (unalloyed) | Refractory metal. |
| Maganese | Various | May include Cr, Ni, Mg, molybdenum. |
| Cobalt cemented tungsten carbide | WC | |
| Cobalt chrome cemented tungsten carbide | CoCr cemented WC | |
| Cobalt chrome cemented chrome carbide | CoCr cemented CrC | |
| Cobalt chrome cemented silicon carbide | CoCr cemented SiC | |
| Fused silicon carbide | SiC | |
| Cobalt chrome molybdenum | CoCrMo | A thin tungsten or tungsten/cobalt layer is placed on the substrate before loading diamond feedstock. |
| Stainless steel | Various | |

The CoCr used is preferably either CoCrMo or CoCrW. The preceding substrates are examples only. In addition to these substrates, other materials may be appropriate for use as substrates for construction of bearing components and other bearing surfaces.

When titanium is used as the substrate, it is sometimes preferred by the inventors to place a thin tantalum barrier layer on the titanium substrate. The tantalum barrier prevents mixing of the titanium alloys with cobalt alloys used in the diamond feedstock. If the titanium alloys and the cobalt alloys mix, it possible that a detrimentally low melting point eutectic inter-metallic compound will be formed during the high pressure and high temperature sintering process. The tantalum barrier bonds to both the titanium and cobalt alloys, and to the polycrystalline diamond that contains cobalt solvent-catalyst metals. Thus, a polycrystalline diamond compact made using a titanium substrate with a tantalum barrier layer and diamond feedstock that has cobalt solvent-catalyst metals can be very strong and well formed. Alternatively, the titanium substrate may be provided with an alpha case oxide coating, an oxidation layer or an oxide composite forming a barrier which prevents formation of a eutectic metal.

If a cobalt chrome molybdenum substrate is used, it is preferred to place either a thin tungsten layer or a thin tungsten and cobalt layer on the substrate before loading of the diamond feedstock in order to control formation of chrome carbide (CrC) during sintering.

In addition to those listed, other appropriate substrates may be used for forming polycrystalline diamond compact bearing surfaces. Further, it is possible within the scope of the invention to form a diamond bearing surface for use without a substrate. It is also possible to form a bearing surface from any of the superhard materials and other bearing materials listed herein, in which case a substrate may not be needed. Additionally, if it is desired to use a type of diamond or carbon other than polycrystalline diamond, substrate selection may differ. For example, if a diamond bearing surface is to be created by use of chemical vapor deposition or physical vapor deposition, then use of a substrate appropriate for those manufacturing environments and for the compositions used will be necessary.

In some embodiments of the invention, the difference in physical properties of the substrate and the diamond layer will result in substantial expansion of the substrate during the sintering process and subsequent shrinkage of the substrate at the conclusion of sintering. Consequently, after sintering, in some instances the substrate may be 0.01% to 1.0% smaller in dimension that it was prior to sintering, Such a result can provide the beneficial effect of the substrate pulling away from the diamond table as desired in some applications, such as a bearing cup. Or it can result in residual stresses between the substrate and the diamond table which, if managed correctly, strengthen the finished part.

Determination of Substrate Geometry

1. General Substrate Configuration

A substrate geometry appropriate for the compact to be manufactured and appropriate for the materials being used should be selected. In order to manufacture a concave spherical cup or race or a convex spherical head as preferred in some embodiments of the invention, it is necessary to select a substrate geometry that will facilitate the manufacture of those parts. In order to ensure proper diamond formation and avoid compact distortion, forces acting on the diamond and the substrate during sintering must be strictly radial. Therefore the preferred substrate geometry at the contact surface with diamond feedstock for manufacturing an cup or race, a head, or any other spherical component is generally spherical.

As mentioned previously, there is a great disparity in the material characteristics of synthetic diamond and most available substrate materials. In particular, modulus and CTE are of concern. But when applied in combination with each other, some substrates can form a stable and strong spherical polycrystalline diamond compact. The table below lists physical properties of some preferred substrate materials.

TABLE 3

MATERIAL PROPERTIES OF SOME PREFERRED SUBSTRATES

| SUBSTRATE MATERIAL | YOUNG'S MODULUS ($\times 10^6$ psi) | BULK MODULUS ($\times 10^6$ psi) | CTE ($\times 10^6$ in/in ° C.) |
|---|---|---|---|
| Ti 6/4 | 15-17 | 11-20 | 5.4 |
| CoCrMo | 33-35 | 27-30 | 16.9 |
| CoCrW | 35.5 | 35 | 16.3 |

Use of either titanium or cobalt chrome substrates alone for the manufacture of spherical polycrystalline diamond compacts may result in cracking of the diamond table or separation of the substrate from the diamond table. In particular, it appears that titanium's dominant property during high pressure and high temperature sintering is compressibility while cobalt chrome's dominant property during sintering is CTE. In some embodiments of the invention, a substrate of two or more layers may be used in order to achieve dimensional stability during and after manufacturing.

Referring to the table below, some combinations of substrate materials that may be used for making spherical polycrystalline diamond compacts are listed.

TABLE 4

SPHERICAL SUBSTRATE COMBINATIONS FOR MAKING CONVEX PCD SPHERES

| SUBSTRATE CORE | SUBSTRATE SHELL | REMARKS |
| --- | --- | --- |
| Ti 6/4 ASTM F-136 sphere | CoCr ASTM F-799 | Alpha case oxide coating on titanium or tantalum barrier layer on titanium. |
| Ti 6/4 ASTM F-136 sphere | CoCr ASTM F-90 | Alpha case oxide coating on titanium or tantalum barrier layer on titanium. |
| CoCr ASTM F-799 sphere | Ti 6/4 ASTM F-136 | Tantalum barrier layer on titanium. |
| CoCr ASTM F-90 sphere | Ti 6/4 ASTM F-136 | Tantalum barrier layer on titanium. |
| CoCr ASTM F-799 sphere | None | Substrate surface topographical features used, as described below. |
| $Al_2O_3$ ceramic core sphere | None | |

The alpha case oxide coating is used to seal the titanium from reacting with the cobalt chrome. The tantalum barrier layer can be in the range of about 0.002 to 0.010 inches thick with 0.008 believed to be optimal.

A two piece substrate as mentioned above may be used to achieve dimensional stability in spherical parts. A two piece substrate may overcome differences in CTE and modulus between diamond and the substrate. It appears that use of a substrate with a plurality of layers overcomes the tendencies of the materials to expand and contract at different rates, which if not addressed will cause cracking of the diamond.

A spherical substrate having at least two distinct layers of different substrate materials can be employed to stabilize the component and prevent the substrate from shrinking away from the diamond table, thus resulting in the successful manufacture of spherical polycrystalline diamond compacts.

Figure 5A:
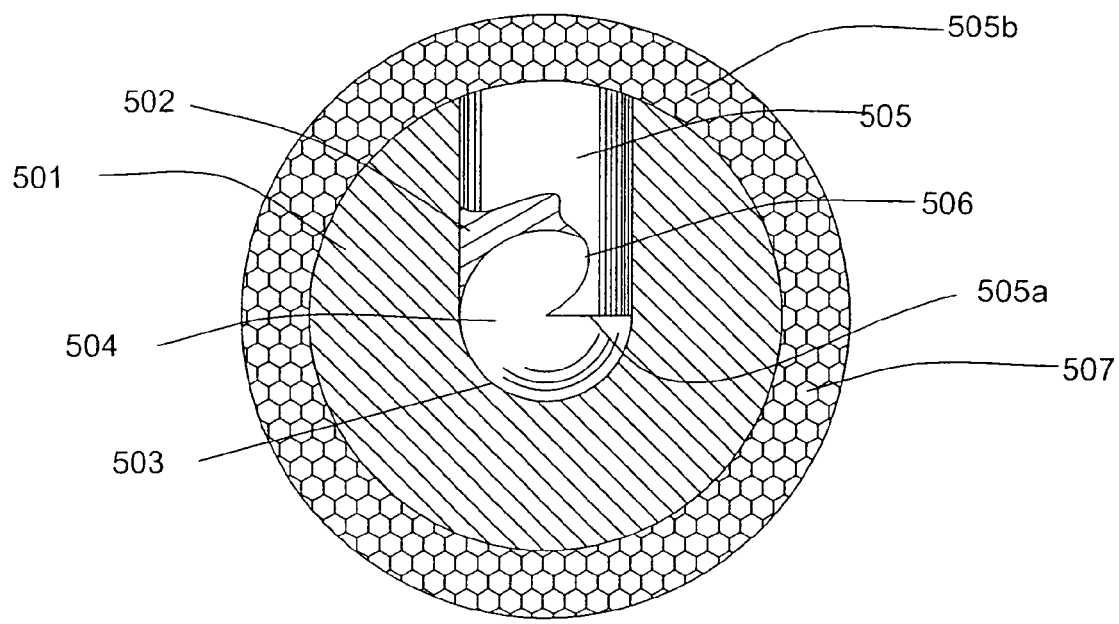
FIGS. 5A and 5B depict two-layer substrates useful for making spherical or partially spherical polycrystalline diamond compacts.
Figure 5B:
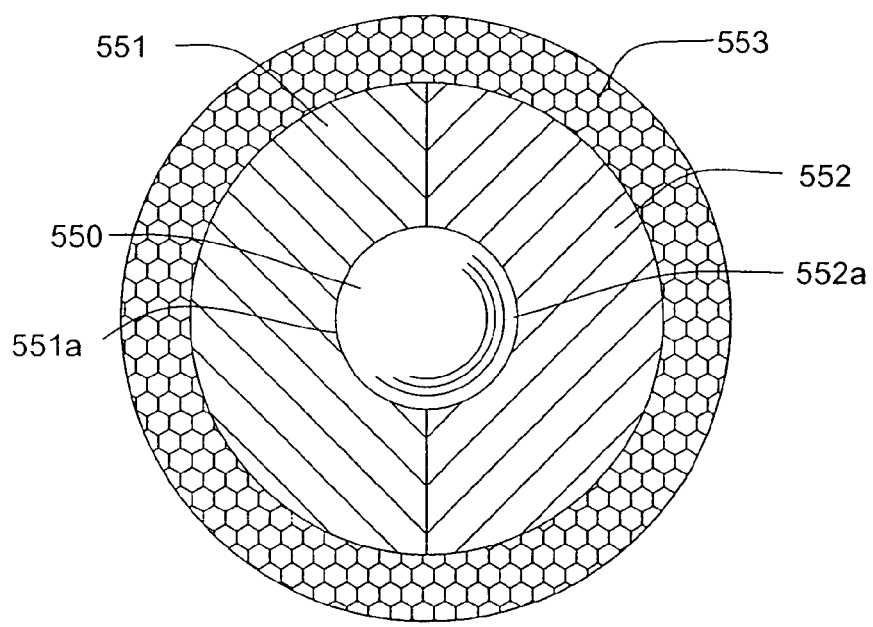

Referring to FIGS. 5A-5F, various substrate structures of the invention for making a generally spherical polycrystalline diamond compact are depicted. FIGS. 5A and 5B depict two-layer substrates.

In FIG. 5A, a solid first sphere 501 of a substrate material intended to be used as the substrate shell or outer layer was obtained. The dimensions of the first sphere 501 are such that the dimension of the first sphere 501 with a diamond table on its exterior will approximate the intended dimension of the component prior to final finishing. Once the first sphere 501 of the substrate is obtained, a hole 502 is bored into its center. The hole 502 is preferably bored, drilled, cut, blasted or otherwise formed so that the terminus 503 of the hole 502 is hemispherical. This is preferably achieved by using a drill bit or end mill with a round or ball end having the desired radius and curvature.

Then a second sphere 504 of a substrate material is obtained. The second sphere 504 is smaller than the first sphere 501 and is be placed in hole 502 in the first sphere 501. The substrates materials of spheres 501 and 504 are preferably selected form those listed in the tables above. They may also be of other appropriate materials. The second sphere 504 and the hole 502 and its terminus 503 should fit together closely without excessive tolerance or gap.

A plug 505 preferably of the same substrate material as first sphere 501 is formed or obtained. The plug 505 has a first end 505a and a second end 505b and substrate material therebetween in order to fill the hole 502 except for that portion of the hole 502 occupied by the second sphere 504 adjacent the hole terminus 503. The plug 505 preferably has a concave hemispherical receptacle 506 at its first end 505a so that plug 505 will closely abut second sphere 504 across about half the spherical surface of second sphere 504. The plug 505 is generally cylindrical in shape. The substrate assembly including one substrate sphere placed inside of another may then be loaded with diamond feedstock 507 and sintered under high pressure at high temperature to form a spherical polycrystalline diamond compact.

Referring to FIG. 5B, another substrate geometry for manufacturing spherical polycrystalline diamond compacts of the invention is depicted. An inner core sphere 550 of appropriate substrate material is selected. Then an outer substrate first hemisphere 551 and outer substrate second hemisphere 552 are selected. Each of the outer substrate first and second hemispheres 551 and 552 are formed so that they each have a hemispherical receptacle 551a and 552a shaped and sized to accommodate placement of the hemispheres about the exterior of the inner core sphere 550 and thereby enclose and encapsulate the inner core sphere 550. The substrates materials of inner core sphere 550 and hemispheres 551 and 552 are preferably selected form those listed in the tables above or other appropriate materials.

With the hemispheres and inner core sphere assembled, diamond feedstock 553 may be loaded about the exterior of the hemispheres and high temperature and high pressure sintering may proceed in order to form a spherical polycrystalline diamond compact.

Although FIGS. 5A and 5B depict two-layer substrates, it is possible to use multiple layer substrates (3 or more layers) for the manufacture of polycrystalline diamond compacts or polycrystalline cubic boron nitride compacts. The selection of a substrate material, substrate geometry, substrate surface topographical features, and substrates having a plurality of layers (2 or more layers) of the same or different materials depend at least in part on the thermo-mechanical properties of the substrate, the baro-mechanical properties of the substrate, and the baro-mechanical properties of the substrate.

Figure 5C:
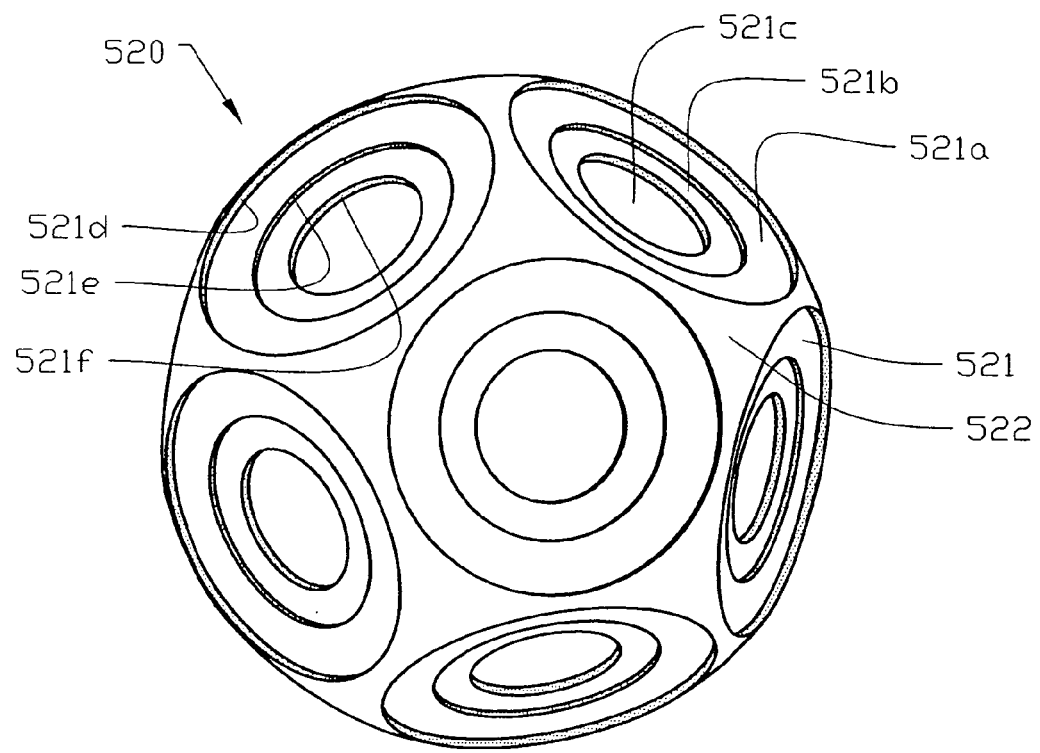
FIGS. 5C-5G depict alternative substrate configurations for making spherical or partially spherical polycrystalline diamond compacts with continuous and segmented bearing surfaces.

Referring to FIG. 5C, another substrate configuration for making generally spherical polycrystalline diamond compacts is depicted. The substrate 520 is in the general form of a sphere. The surface of the sphere includes substrate surface topography intended to enhance fixation of a diamond table to the substrate. The substrate has a plurality of depressions 521 formed on its surface. Each depression 521 is formed as three different levels of depression 521a, 521b and 521c. The depressions are depicted as being concentric circles, each of approximately the same depth, but their depths could vary, the circles need not be concentric, and the shape of the depressions need not be circular. The depression walls 521d, 521e and 521f are depicted as being parallel to a radial axis of the depressions which axis is normal to a tangent to the theoretical spherical extremity of the sphere, but could have a different orientation if desired. As depicted, the surface of the substrate sphere 522 has no topographical features other than the depressions already mentioned, but could have protrusions, depressions or other modifications as desired. The width and depth dimensions of the depressions 521 may be varied according to the polycrystalline diamond compact that is being manufactured.

Diamond feedstock may be loaded against the exterior of the substrate sphere 520 and the combination may be sintered at diamond stable pressures to produce a spherical polycrystalline diamond compact. Use of substrate surface topographical features on a generally spherical substrate provides a superior bond between the diamond table and the substrate as described above and permits a polycrystalline diamond compact to be manufactured using a single layer substrate. That is because of the gripping action between the substrate and the diamond table achieved by use of substrate surface topographical features.

Figure 5D:
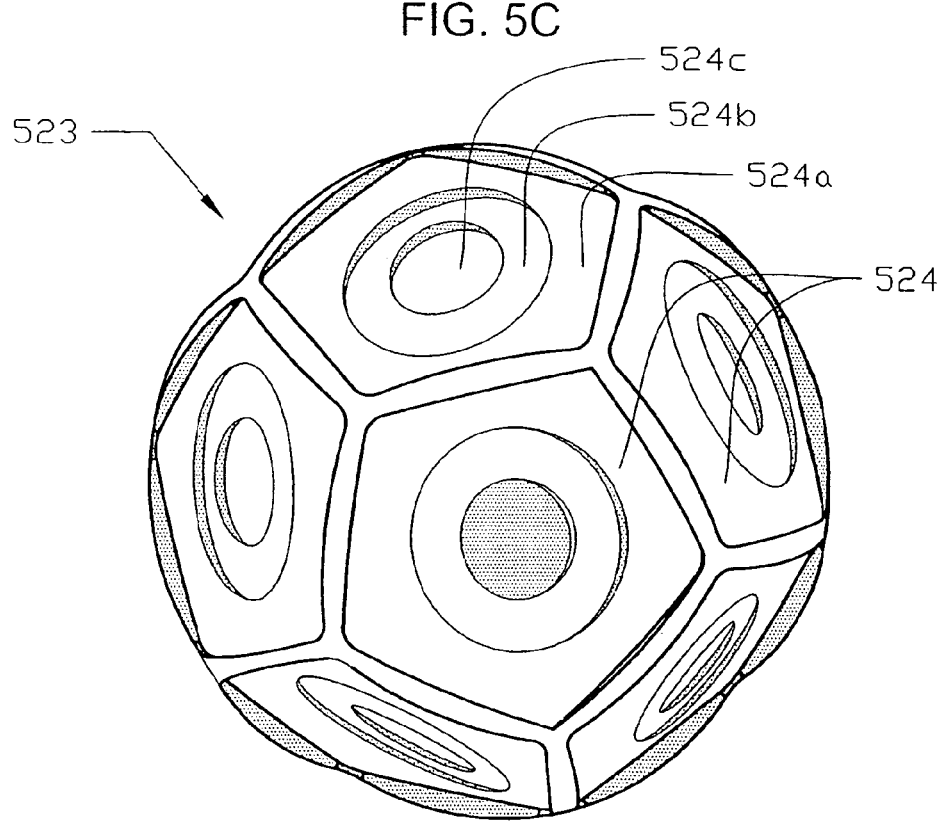

Referring to FIG. 5D, a segmented spherical substrate 523 is depicted. The substrate has a plurality of surface depressions 524 equally spaced about its exterior surface. These depressions as depicted are formed in levels of three different depths. The first level 524a is formed to a predetermined depth and is of pentagonal shape about its outer periphery. The second level 524b is round in shape and is formed to a predetermined depth which may be different from the predetermined depth of the pentagon. The third level 524c is round in shape in is formed to a predetermined depth which may be different from each of the other depths mentioned above. Alternatively, the depressions may be formed to only one depth, may all be pentagonal, or may be a mixture of shapes. The depressions may be formed by machining the substrate sphere.

Figure 5E:
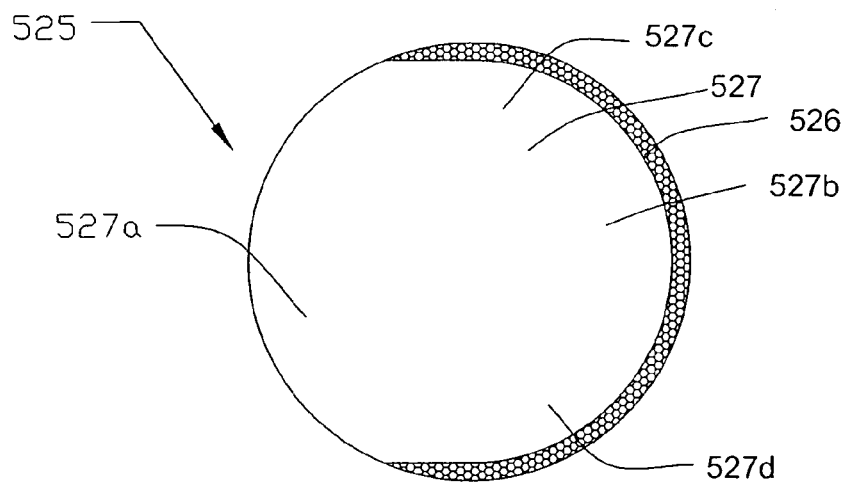

Referring to FIG. 5E, a cross section of an alternative substrate configuration for making a polycrystalline diamond compact is shown. A polycrystalline diamond compact 525 is shown. The compact 525 is spherical. The compact 525 includes a diamond table 526 sintered to a substrate 527. The substrate is partially spherical in shape at its distal side 527a and is dome-shaped on its proximal side 527b. Alternatively, the proximal side 527b of the substrate 527 may be described as being partially spherical, but the sphere on which it is based has a radius of smaller dimension than the radius of the sphere on which the distal side 527a of the substrate is based. Each of the top 527c and bottom 527d are formed in a shape convenient to transition from the proximal side 527b substrate partial sphere to the distal side 527a substrate partial sphere. This substrate configuration has advantages in that it leaves a portion of substrate exposed for drilling and attaching fixation components without disturbing residual stress fields of the polycrystalline diamond table. It also provides a portion of the substrate that does not have diamond sintered to it, allowing dilatation of the substrate during sintering without disruption of the diamond table. More than 180 degrees of the exterior of the substrate sphere has diamond on it, however, so the part is useful as a head or other articulation surface.

Figure 5F:
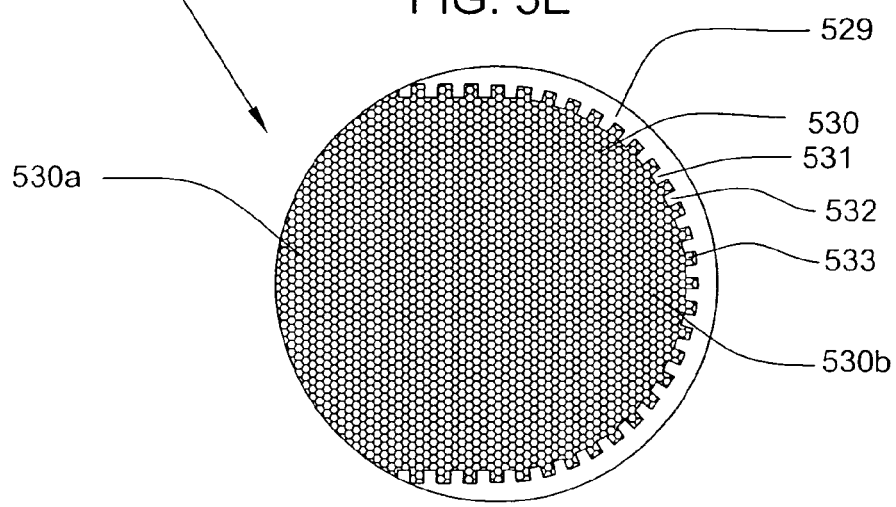

Referring to FIG. 5F, a cross section of an alternative substrate configuration for making a polycrystalline diamond compact is shown. A polycrystalline diamond compact 528 is depicted having a diamond table 529 and a substrate 530. The substrate has topographical features 531 for enhancing strength of the diamond to substrate interface. The topographical features may include rectangular protrusions 532 spaced apart by depressions 533 or corridors. The distal side of the substrate is formed based on a sphere of radius r. The proximal side of the substrate 530b is formed based on a sphere of radius r', where r>r'. Usually the surface modifications will be found beneath substantially all of the diamond table.

Figure 5G:
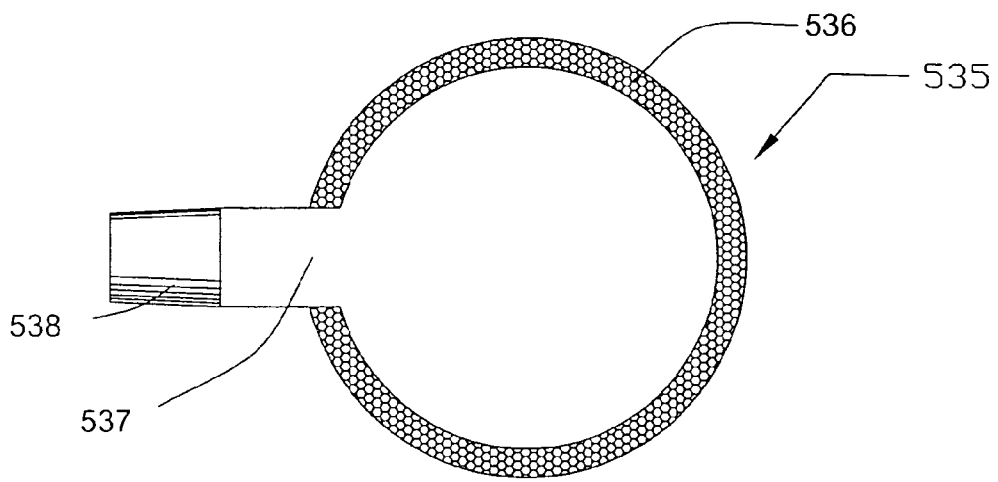
Figures 1, 6A:
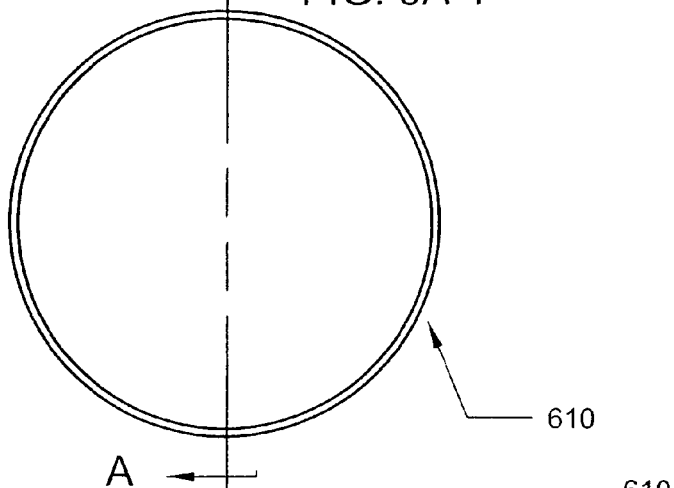
Figures 2, 6A:
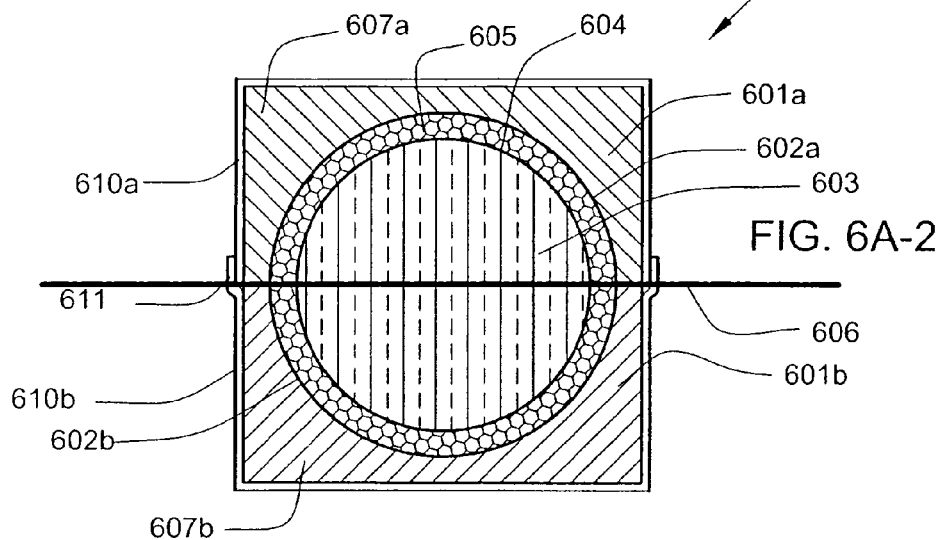
Figures 1, 6B:
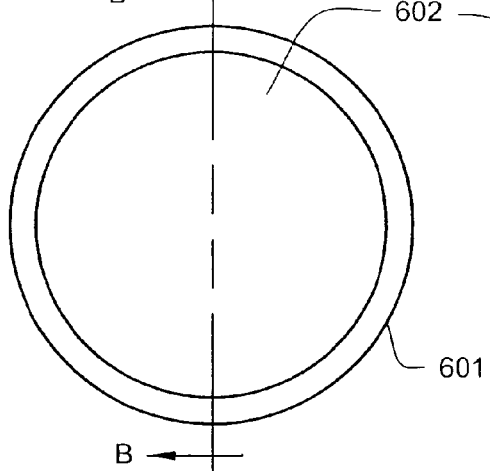
Figures 2, 6B:
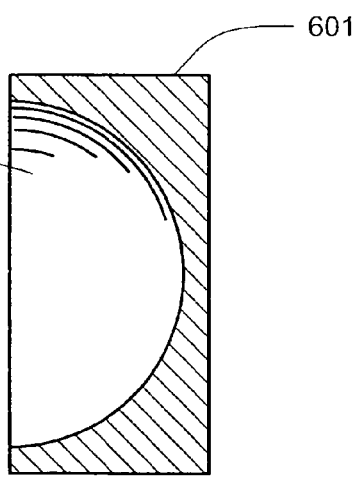

Referring to FIG. 5G, a head 535 of a bearing component is depicted. The head 535 that includes a diamond table 536 sintered to a substrate 536. The substrate is configured as a sphere with a protruding cylindrical shape. The head 535 is formed so that a quantity of substrate protrudes from the spherical shape of the head to form a neck 538 and attachment 537 which may be attached to an appropriate body by any known attachment method, such as by self-locking taper fit, welding, threads or other attachment mechanisms. The use of a neck 538 preformed on the substrate that is used to manufacture a polycrystalline diamond compact 535 provides an attachment point on the polycrystalline diamond compact that may be utilized without disturbing the residual stress field of the compact.

Any of the previously mentioned substrate configurations and substrate topographies and variations and derivatives of them may be used to manufacture a polycrystalline diamond compact for use in a load bearing or articulation surface environment.

In various embodiments of the invention, a single layer substrate may be utilized. In other embodiments of the invention, a two-layer substrate may be utilized, as discussed. Depending on the properties of the components being used, however, it may be desired to utilize a substrate that includes three, four or more layers. Such multi-layer substrates are intended to be comprehended within the scope of the invention.

The preferred substrate geometry for manufacturing an cup or race or other concave spherical, hemispherical or partially spherical polycrystalline diamond compact of the invention differs from that used to manufacture a convex spherical polycrystalline diamond compact. Referring to FIGS. 6A-1, 6A-2, 6B-1 and 6B-2-6C below, the preferred assembly for manufacturing a concave spherical polycrystalline diamond compact (such as that used in an cup or race) are depicted. The substrate 601 (and 601a and 601b) is preferably in the form of a cylinder with a hemispherical receptacle 602 (and 602a and 602b) formed into one of its ends.

Two substrate cylinders 601a and 601b are placed so that their hemispherical receptacles 602a and 602b are adjacent each other, thus forming a spherical cavity 604 between them. A sphere 603 of an appropriate substrate material is located in the cavity 604. Diamond feedstock 605 is located in the cavity 604 between the exterior of the sphere 603 and the concave surfaces of the receptacles 602a and 602b of the substrate cylinders 601a and 601b. The assembly is placed into a refractory metal can 610 for sintering. The can has a first cylinder 610a and a second cylinder 601b. The two cylinders join at a lip 611.

After such an assembly is sintered, the assembly may be slit, cut or ground along the center line 606 in order to form a first cup or race assembly 607a and a second cup or race assembly 607b. The preferred substrate materials for the cylinders 602a and 602b are CoCrMo (ASTM F-799) and CoCrW (ASTM F-90), and the preferred substrate material for the sphere 603 is preferably CoCrMo (ASTM F-799), although any appropriate substrate material may be used, including some of those listed in the tables.

While two layer substrates have been discussed above for manufacturing concave and convex spherical polycrystalline diamond compacts, it is also possible to use substrates consisting of more than two layers of material or substrates of a single type of material in manufacturing spherical polycrystalline diamond compacts.

2. Substrate Surface Topography

Depending on the application, it may be advantageous to include substrate surface topographical features on a substrate that is to be formed into a polycrystalline diamond compact. Regardless whether a one-piece, a two-piece of a multi-piece substrate is used, it may be desirable to modify the surface of the substrate or provide topographical features on the substrate in order to increase the total surface area of diamond to enhance substrate to diamond contact and to provide a mechanical grip of the diamond table.

The placement of topographical features on a substrate serves to modify the substrate surface geometry or contours from what the substrate surface geometry or contours would be if formed as a simple planar or non-planar figure. Substrate surface topographical features may include one or more different types of topographical features which result in protruding, indented or contoured features that serve to increase surface, mechanically interlock the diamond table to the substrate, prevent crack formation, or prevent crack propagation.

Substrate surface topographical features or substrate surface modifications serve a variety of useful functions. Use of substrate topographical features increases total substrate surface area of contact between the substrate and the diamond table. This increased surface area of contact between diamond table and substrate results in a greater total number of chemical bonds between diamond table and substrate than if the substrate surface topographical features were absent, thus achieving a stronger polycrystalline diamond compact.

Substrate surface topographical features also serve to create a mechanical interlock between the substrate and the diamond table. The mechanical interlock is achieved by the nature of the substrate topographical features and also enhances strength of the polycrystalline diamond compact.

Substrate surface topographical features may also be used to distribute the residual stress field of the polycrystalline diamond compact over a larger surface area and over a larger volume of diamond and substrate material. This greater distribution can be used to keep stresses below the threshold for crack initiation and/or crack propagation at the diamond table/substrate interface, within the diamond itself and within the substrate itself.

Substrate surface topographical features increase the depth of the gradient interface or transition zone between diamond table and substrate, in order to distribute the residual stress field through a longer segment of the composite compact structure and to achieve a stronger part.

Substrate surface modifications can be used to created a sintered polycrystalline diamond compact that has residual stresses that fortify the strength of the diamond layer and yield a more robust polycrystalline diamond compact with greater resistance to breakage than if no surface topographical features were used. This is because in order to break the diamond layer, it is necessary to first overcome the residual stresses in the part and then overcome the strength of the diamond table.

Substrate surface topographical features redistribute forces received by the diamond table. Substrate surface topographical features cause a force transmitted through the diamond layer to be re-transmitted from single force vector along multiple force vectors. This redistribution of forces travelling to the substrate avoids conditions that would deform the substrate material at a more rapid rate than the diamond table, as such differences in deformation can cause cracking and failure of the diamond table.

Substrate surface topographical features may be used to mitigate the intensity of the stress field between the diamond and the substrate in order to achieve a stronger part.

Substrate surface topographical features may be used to distribute the residual stress field throughout the polycrystalline diamond compact structure in order to reduce the stress per unit volume of structure.

Substrate surface topographical features may be used to mechanically interlock the diamond table to the substrate by causing the substrate to compress over an edge of the diamond table during manufacturing. Dovetailed, hemispherical and lentate modifications act to provide force vectors that tend to compress and enhance the interface of diamond table and substrate during cooling as the substrate dilitates radially.

Substrate surface topographical features may also be used to achieve a manufacturable form. As mentioned herein, differences in coefficient of thermal expansion and modulus between diamond and the chosen substrate may result in failure of the polycrystalline diamond compact during manufacturing. For certain parts, the stronger interface between substrate and diamond table that may be achieved when substrate topographical features are used can achieve a polycrystalline diamond compact that can be successfully manufactured. But if a similar part of the same dimensions is to be made using a substrate with a simple substrate surface rather than specialized substrate surface topographical features, the diamond table may crack or separate from the substrate due to differences in coefficient of thermal expansion or modulus of the diamond and the substrate.

Examples of useful substrate surface topographical features include waves, grooves, ridges, other longitudinal surface features (any of which may be arranged longitudinally, lattitudinally, crossing each other at a desired angle, in random patterns, and in geometric patterns), three dimensional textures, spherical segment depressions, spherical segment protrusions, triangular depressions, triangular protrusions, arcuate depressions, arcuate protrusions, partially spherical depressions, partially spherical protrusions, cylindrical depressions, cylindrical protrusions, rectangular depressions, rectangular protrusions, depressions of n-sided polygonal shapes where n is an integer, protrusions of n-sided polygonal shapes, a waffle pattern of ridges, a waffle iron pattern of protruding structures, dimples, nipples, protrusions, ribs, fenestrations, grooves, troughs or ridges that have a cross-sectional shape that is rounded, triangular, arcuate, square, polygonal, curved, or otherwise, or other shapes. Machining, pressing, extrusion, punching, injection molding and other manufacturing techniques for creating such forms may be used to achieve desired substrate topography. Although for illustration purposes, some sharp corners are depicted on substrate topography or other structures in the drawings, in practice it is expected that all corners will have a small radius to achieve a component with superior durability.

Figure 3:
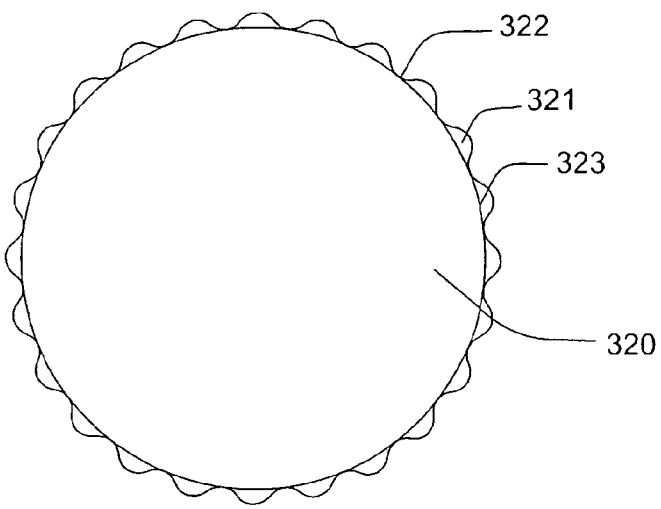
FIGS. 3A-3U depict substrate surface topographical features desirable in some embodiments of the invention.
Figure 3J:
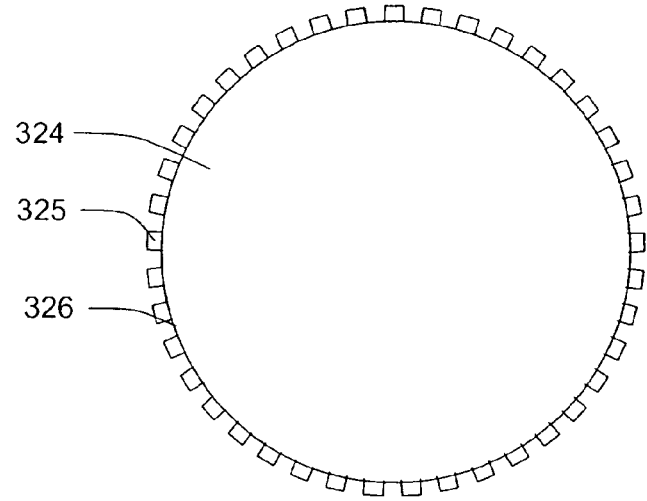
Figure 3K:
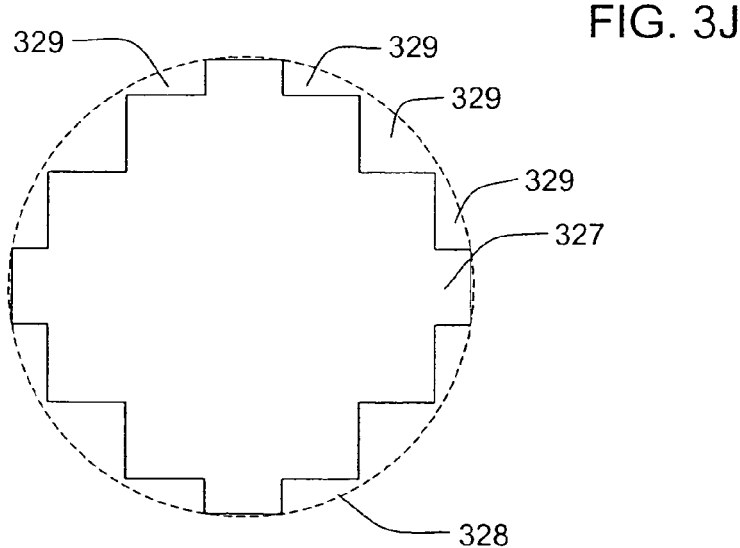
Figure 3L:
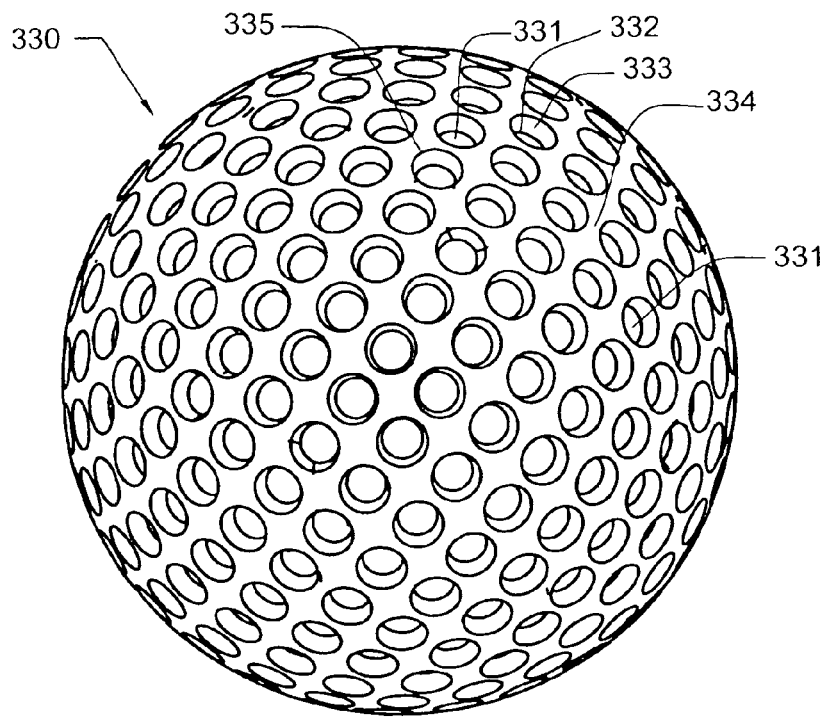
Figure 3M:
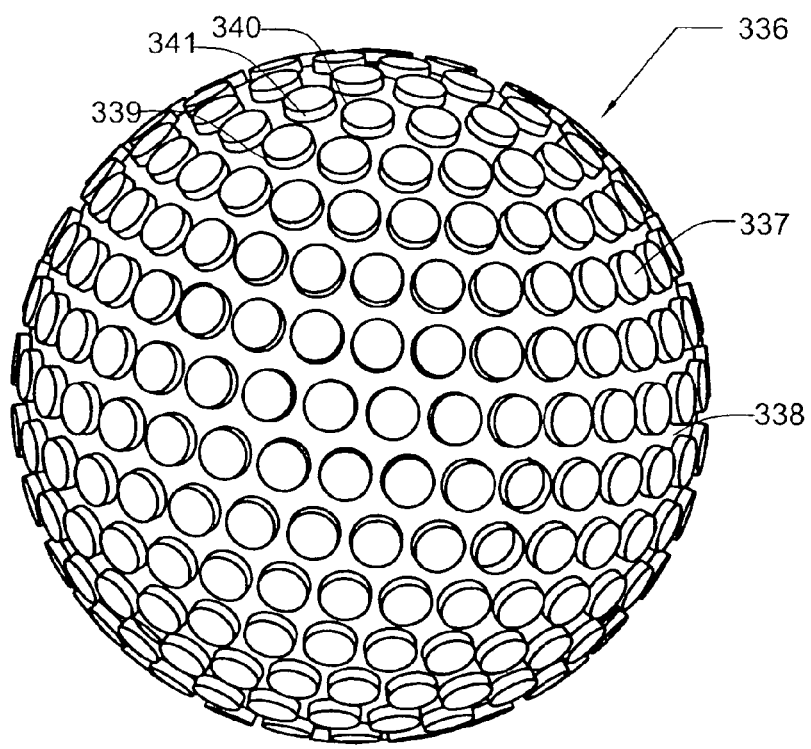
Figure 3N:
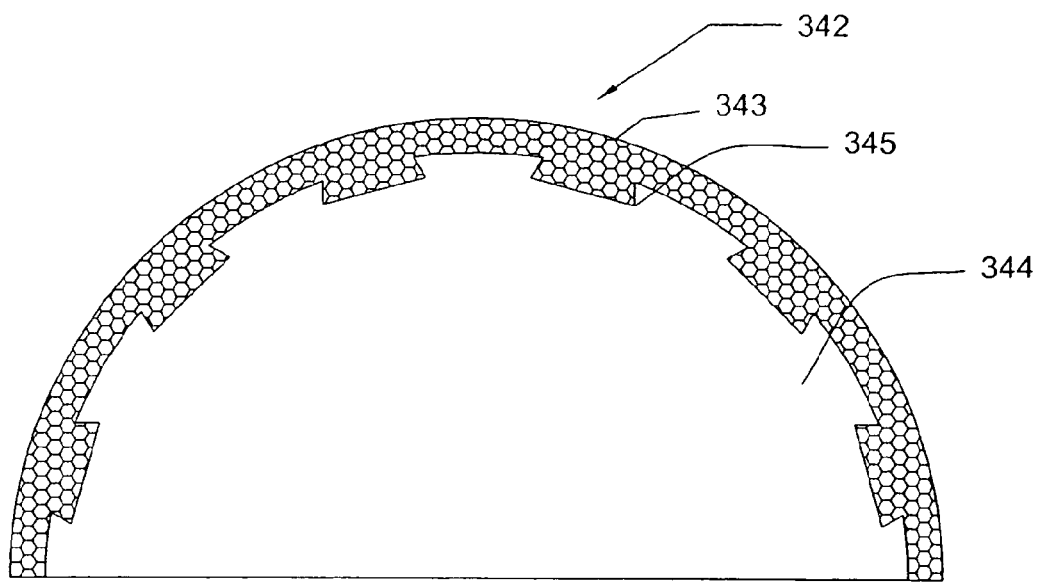
Figure 3:
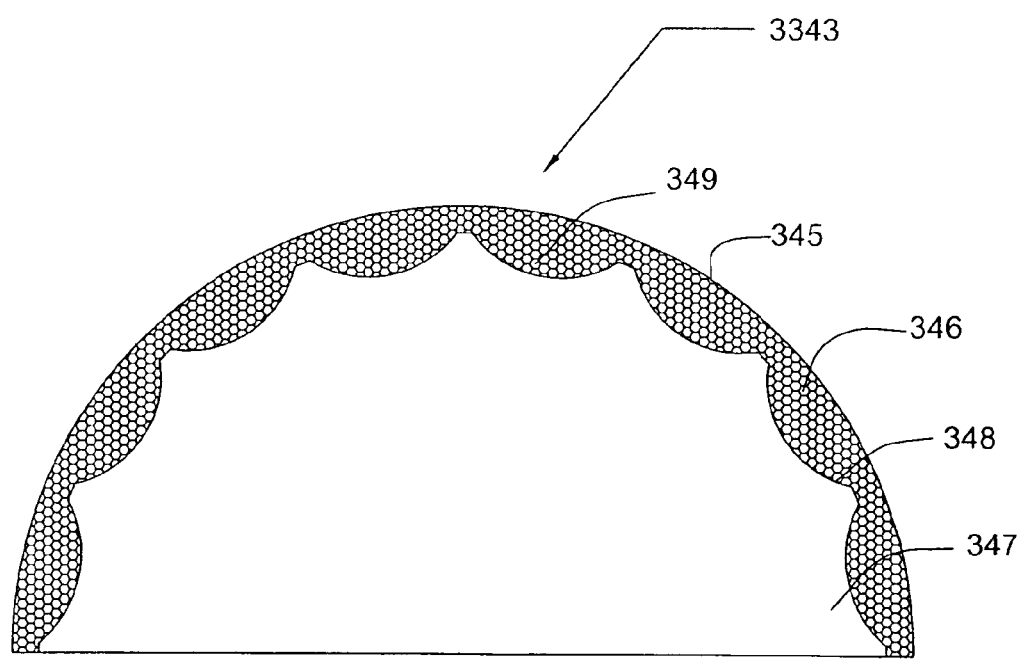
Figure 3P:
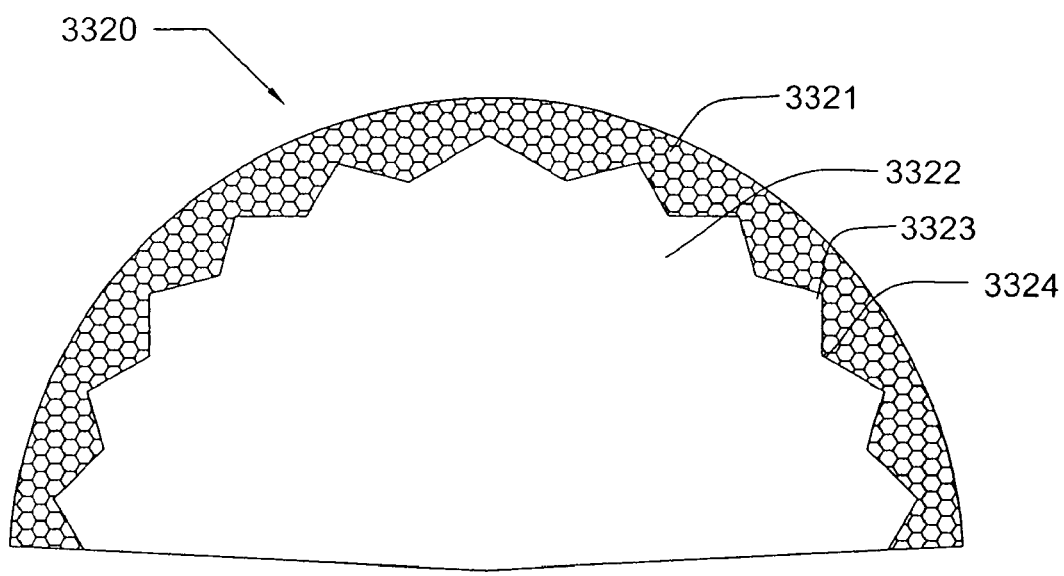
Figure 3Q:
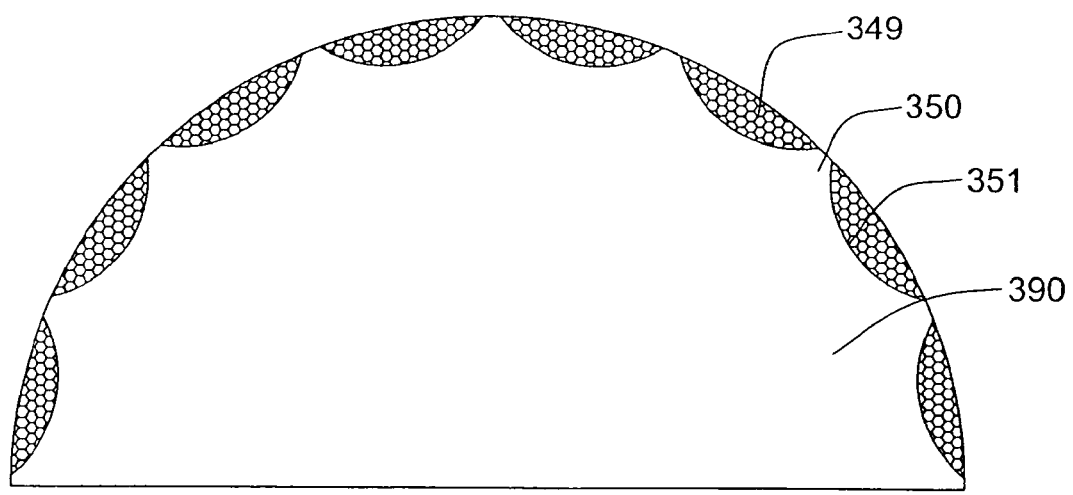
Figure 3R:
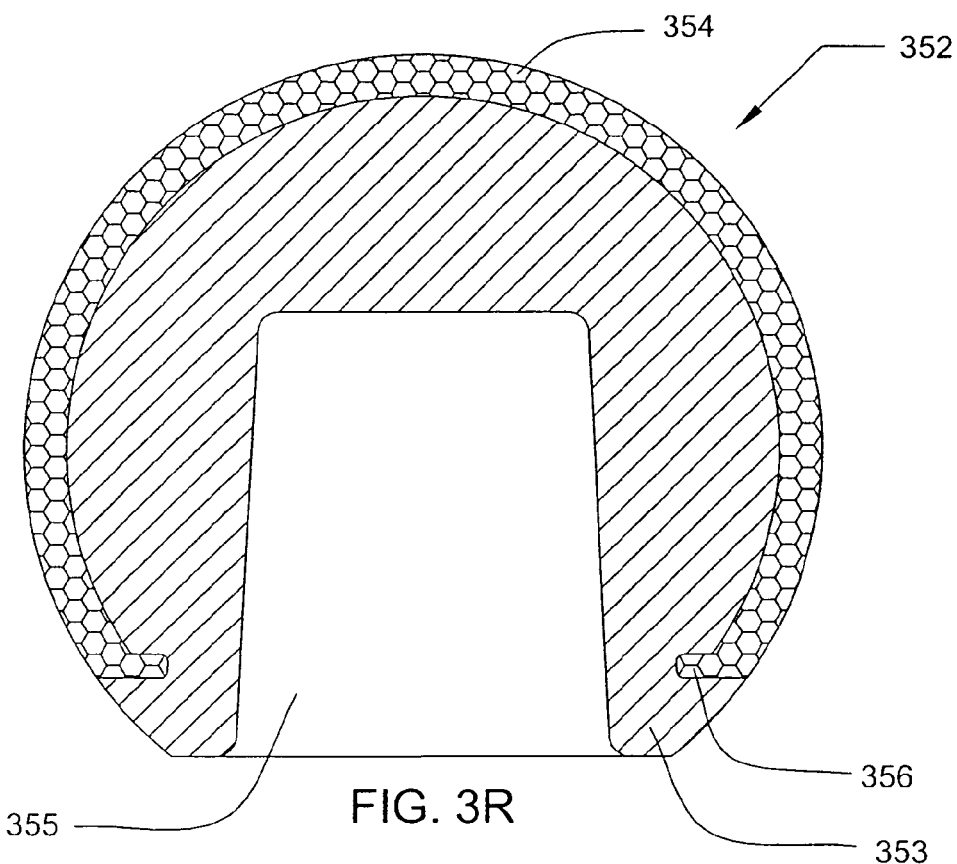
Figure 3S:
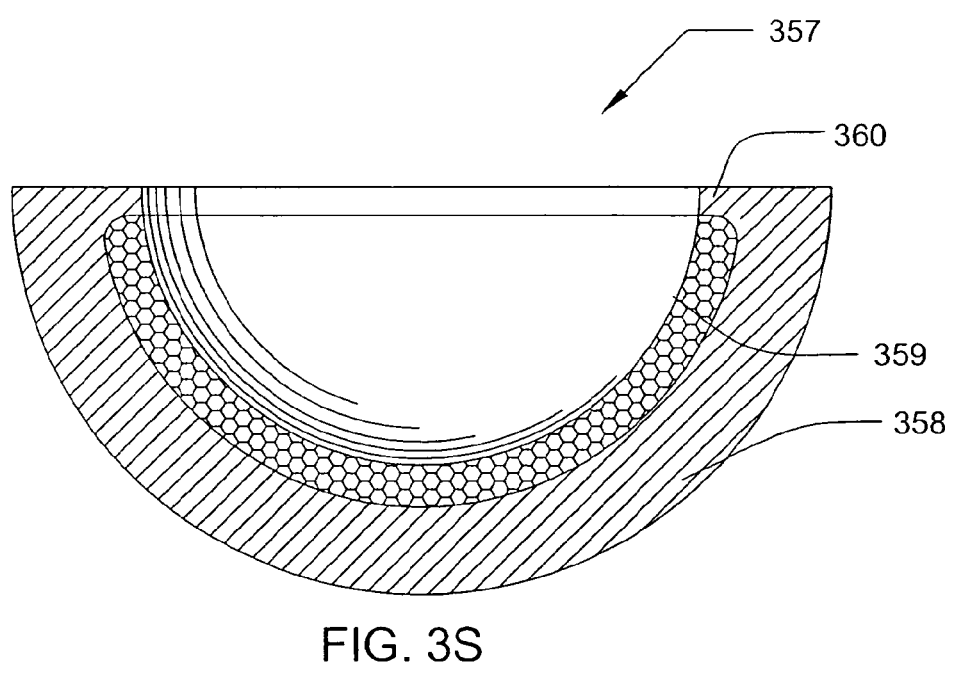
Figure 3T:
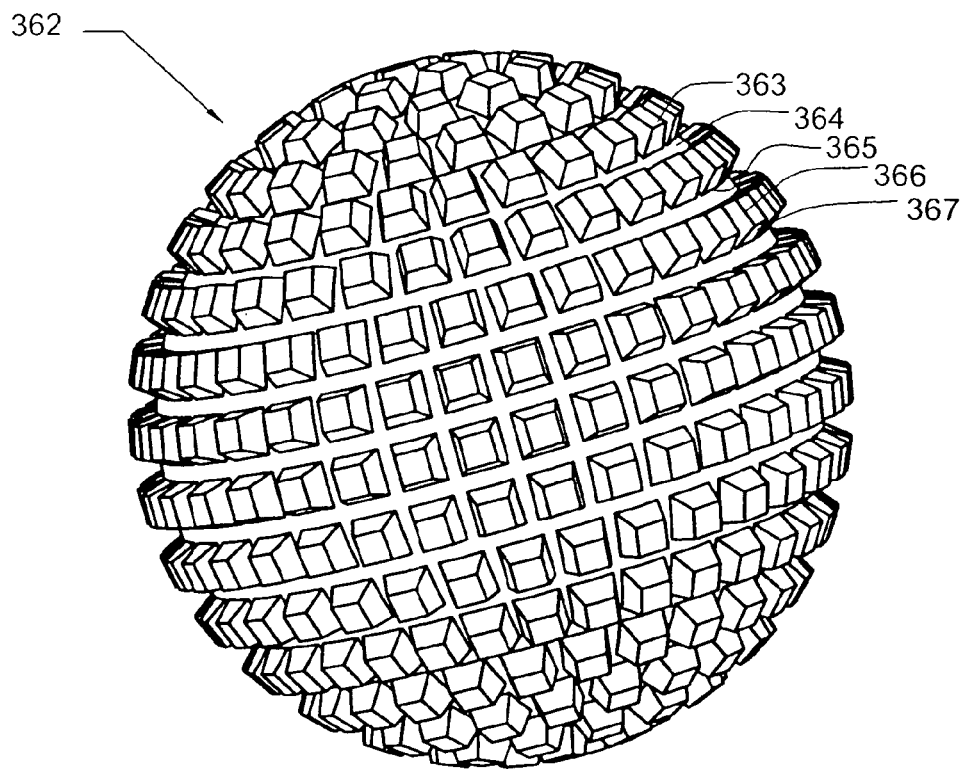
Figure 3U:
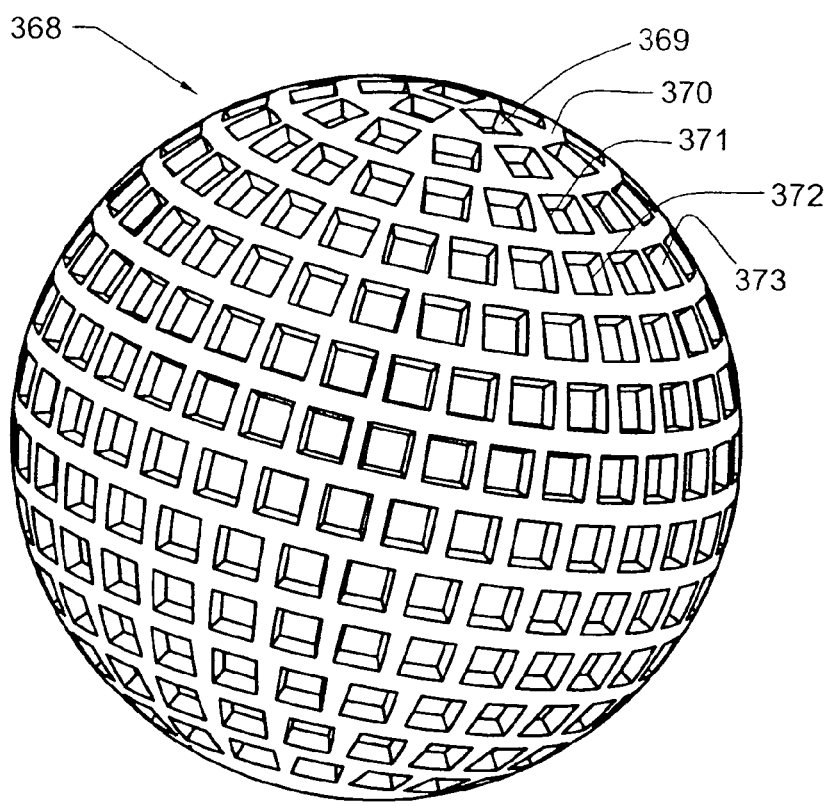

FIGS. 3A-3U depict a few possible substrate surface modifications. Referring to FIG. 3A, a ball structure on a stem is depicted that features concave and convex substrate surface topographical features. A head 380 is shown that has a diamond table 382 sintered to a substrate 383. The substrate 383 has surface topography that includes concave arcuate grooves 384 and convex arcuate ridges 385 radiating from a point on the substrate. The diamond 382 covers the substrate topographical features, resulting in a greater surface area of contact between the diamond table and the substrate than if a simple rounded substrate were employed.

FIG. 3B shows redistribution of a force applied to the head 380 of FIG. 3A. When a force F1 is applied to the head 380, that force F1 is redistributed along force vectors F2 and F3, as shown. Thus, although on the diamond table 382 a single force vector is received, that force vector is broken down into smaller forces and transmitted through the substrate 383. This redistribution of forces decreases the possibility of a differential in rates of deformation of the diamond table and the substrate and therefore reduces the chance of the diamond table cracking and failing.

FIG. 3C depicts use of substrate topographical features on a head in a ball and cup or race bearing assembly. The cup or race 386 is mounted in a desired structure 387. The cup or race 386 has a polycrystalline diamond table 388 attached to a substrate 389. The head 390 includes a table of polycrystalline diamond 391 on a substrate 392.

The substrate 392 has surface topography including grooves 393 oriented so that they will be generally vertical when the bearing component is in use. The primary force vector F1 is generally parallel to the grooves 393. The force zone 394 due to use is shown above the cup or race. Use of substrate surface topography that includes grooves that are generally vertically oriented when the bearing is in use achieves wider redistribution of forces.

FIG. 3D depicts a convex sphere 350 of appropriate substrate material. The sphere 350 has a polar axis 351 and an equator 352. A plurality of surface modifications 353 were formed in the surface of the sphere 350. The surface modifications are arranged in a close offset configuration. The surface modifications can range from less than about 0.001 inch to more than about 0.750 inch diameter cylindrical depressions having a depth of from less than about 0.001 inch to more than about 0.750 inch or otherwise as desired. Very small surface topographical features can be created by use of a laser. In most embodiments of the invention, substrate surface topographical features will cover from about 1% to about 99% of the surface of the substrate beneath the diamond table. The substrate surface topographical features will have a depth of from about 1% of the radius of the part to about 50% of the radius of the part. Discrete substrate surface topographical features will have a dimension measured along a tangent to the substrate surface of from about 1% to about 50% of the radius of the part.

FIG. 3E depicts a cross section of a polycrystalline diamond compact formed using a spherical substrate with a modified substrate surface, such as that depicted in FIG. 3A. The compact 360 has a diamond layer 361 sintered to a substrate 362. The substrate 362 has surface modifications 363 in which diamond 361 is found. The substrate in the vicinity of the surface modification 363 tends to grip the diamond at force lines F1 and F2, thus adding a mechanical gripping advantage to the chemical bonds of the polycrystalline diamond compact, and resulting in a very strong part.

FIG. 3F depicts substrate surface convex rounded protrusions 379 or nipples on a substrate 378. The nipples or protrusions are depicted as being rounded or arcuate. FIG. 3G depicts substrate surface protruding ridges 377 and grooves 376 on a substrate 375. FIG. 3H depicts a substrate 374 having elevated ridges 273 and rounded or arcuate grooves 372 between the ridges. This substrate surface configuration may be made by machining grooves that are round in cross section in a spherical substrate. The ridges 377 are substrate material left between the grooves that have been machined.

FIG. 3I depicts a convex spherical substrate 320. Absent specialized substrate surface topographical features, the substrate 320 would be in the form of a simple sphere as depicted by circle 323. This substrate 320 includes rounded or arcuate wavelike forms on its exterior surface that take the shape of protruding ridges 322 and depressed grooves 321.

FIG. 3J depicts a convex spherical substrate 324. The substrate 324 includes protruding rectangular forms 325 which form a waffle-like pattern on the surface of the substrate 324. Between each protruding form 325 is a gap, groove, trough, or alley 326.

FIG. 3K depicts a substrate 327. Such a substrate may have been simple convex spherical as indicated by dashed circle 328, but has been machined to have its present form. The substrate 327 has had polygonal shapes 329 formed into its surface to create specialized topographical features for an interface with a diamond table.

FIG. 3L depicts a generally spherical substrate 330 having a plurality of depressions 331 formed in its surface. The surface 334 of the substrate sphere 330 is spherical in shape except for the depressions 331. The depressions have a circular upper rim 335, a circular bottom 332, and a sidewall 333 of a desired depth. As desired, the maximum diameter of the rim 335 of a depression may have the same or greater dimension than the maximum diameter of the bottom 332 of the same depression. If the two diameters are the same, then the depression will have a cylindrical shape. If the rim 335 has a greater diameter than the bottom 333, then the depression will have a frusto-conical shape. Diamond may be bonded on a substrate as depicted in FIG. 3L in table that has a thickness that completely covers the outside surface of the substrate. In that case, the diamond table will be thicker in areas above a depression than in other areas. If such a diamond table is used, then from outward appearance, the substrate surface topographical features will not be discernible. Alternatively, diamond may be bonded in the depressions only, leaving the substrate between depressions exposed. Such a configuration is discussed in more detail with respect to FIG. 3Q.

FIG. 3M depicts a generally spherical substrate 336 having a plurality of protrusions 337 on its surface. The surface 338 of the substrate sphere 336 is spherical in shape except for the protrusions 337. The protrusions have a circular lower rim 339, a circular upper rim 340, and a sidewall 341 of a desired height. The protrusion tops 342 may be of any desired shape, such as flat, domed, partially spherical, arcuate, or otherwise. As desired, the maximum diameter of the lower rim 339 and the upper rim 340 may differ. If the two diameters are the same and the sidewall 341 is straight, then the protrusion will have a generally cylindrical shape. If the rim 339 has a greater diameter than the rim 340, then the protrusion will have a generally frusto-conical shape. A diamond table may be attached to the substrate of FIG. 3M to that the diamond table completely covers the substrate surface modifications and the areas between them. In such a configuration, from outward appearance the substrate surface modifications would not be discernible. Alternatively, diamond may be attached to the substrate only between the substrate surface modifications, creating a web or network of exposed diamond having discontinuous areas of exposed substrate material.

FIG. 3N depicts a spherical polycrystalline diamond compact 342 including a diamond table 343 and a substrate 344. The substrate 344 includes topographical surface modifications. The surface modifications include dovetail depressions 345 formed in the substrate. Polycrystalline diamond has formed in the dovetail to create a tight mechanical interlock between the diamond table and the substrate. This structure may be achieved by forming depressions in the surface of a substrate that do not have a dovetail shape. During sintering, the dovetail interlock between the substrate and the diamond table can be formed due to differences in the coefficient of thermal expansion and modulus between diamond and the substrate material.

FIG. 3O depicts a partially spherical polycrystalline diamond compact 3343 having a diamond table 346 and a substrate 347. The diamond table 346 presents a continuous diamond load bearing and articulation surface. The substrate 347 has been formed with surface topography intended to effect a stronger bond with the diamond table. The substrate 347 includes hemispherical or lentate modifications 348 formed on the substrate outer surface. The modifications depicted are concave partially spherical depressions on the substrate surface. Polycrystalline diamond forms in the depressions 349. During sintering, as the polycrystalline diamond compact cools, the substrate tends to dilatate radially. The hemispherical depressions of this surface modification provide force vectors that compress and enhance the interface between the diamond table and the substrate, to achieve a much stronger bond between the diamond table and the substrate. Thus, a mechanical grip or interlock is created between the diamond table and the substrate both as a result of the differences in CTE between the diamond and the substrate and as a result of the substrate topographical features.

FIG. 3P depicts a partially spherical polycrystalline diamond compact 3320. The compact 3320 includes a diamond table 3321 and a substrate 3322. The substrate 3322 has topographical features that include ridges 3323 and troughs 3324 that are triangular in cross section. The use of substrate topographical features such as these provides a gradient interface or transition zone between the diamond and the substrate as described elsewhere herein. The gradient interface I found in a polycrystalline diamond compact that has substrate topographical features is typically of greater depth than that found in a polycrystalline diamond compact that has a substrate with a simple surface. Consequently, the residual stress field in a polycrystalline diamond compact that has substrate topographical features is distributed through a longer segment of the composite compact structure, and is distributed over a greater volume of diamond and substrate materials. The result is a polycrystalline diamond compact that is stronger and more stable than that which may be achieved without the use of substrate topographical features.

FIG. 3Q depicts a partially spherical polycrystalline diamond compact. The compact includes a substrate 390 formed with diamond receptacles, depressions or indentations 351. On sintering, polycrystalline diamond 349 is formed in the depressions 351 in order to create a load bearing and articulation surface that includes discontinuous or segmented areas of diamond. Between the diamond areas 349, there is exposed substrate material 350 on the load bearing and articulation surface. During finish polishing, the lesser hardness of the substrate material compared to diamond will tend to cause the exposed substrate 350 to be relieved, presenting a load bearing and articulation surface on which the primary contact and articulation is provided by the diamond patches 349. If desired, the exposed substrate 350 may be machined or polished to provide sufficient relief to serve as a channel for communicating lubricating fluids to the load bearing and articulation surface.

FIG. 3R depicts a spherical ball 352 that has a substrate 353 and a diamond table 354. The substrate 353 includes a receptacle 355 for receiving an attachment mechanism. The diamond table 354 covers less than the entire surface of the substrate 353. As depicted, the diamond table 354 has a hemispherical configuration. The substrate 353 has been prepared with an annular groove or ring 356 about its equator. The diamond table 354 is thicker in the area of the annular groove 356 and occup or raceies the annular groove 356 in order to provide strong bonding at the edge of the diamond table 354.

FIG. 3S depicts a cup or race 357 having a substrate 358 and a diamond table load bearing and articulation surface 359. The substrate 358 includes a lip 360 which interlocks the diamond table 359 in place in the cup or race 357. Although the lip 360 structure may be formed in the substrate 358 prior to sintering of the polycrystalline diamond compact, the lip 360 structure may also be formed or enhanced by dilatation of the substrate material during sintering. The lip reduces or eliminates edge effect at the extreme radial interface of the diamond table 359 and the substrate 358 in order to provide a stronger and more durable component.

FIG. 3T depicts a generally spherical substrate 362 having a plurality of truncated pyramid-like or polygonal protrusions 363 on its surface. The surface 364 of the substrate sphere 362 is generally spherical in shape except for the protrusions 363. The protrusions have a square or rectangular lower perimeter 365, a square or rectangular upper perimeter 366 and a side wall 364 of desired height. The protrusion tops 366 may differ to form a plurality of different angles between the lower and upper perimeters. If the two perimeters are the same dimension and the sidewall 367 is straight, then the protrusions will have a generally square or rectangular shape. If the upper perimeter 366 has a smaller dimension than the lower perimeter, then the protrusion will have a generally truncated pyramid shape. If the upper perimeter 366 is larger than the lower perimeter 365, the protrusion will have a generally inverted truncated pyramid shape. A diamond table may attach to the substrate of FIG. 3T so that the diamond table completely covers the substrate surface modifications and the areas between them. In such a configuration, from outward appearance, the substrate surface modifications would not be discernable. Alternatively, diamond may be attached to the substrate only between the substrate surface modifications, creating a web or network of exposed diamond having discontinuous areas of exposed substrate material.

FIG. 3U depicts a generally spherical substrate 368 having a plurality of depressions 369 formed into its surface. The surface 370 of the substrate sphere 368 is spherical in shape except for the depressions 369. The depressions have a square or rectangular upper perimeter 371, a square or rectangular bottom 372, and a sidewall 373 of a desired depth. As desired, the maximum upper perimeter 371 of a depression may have the same dimension of the bottom perimeter 372 of the same depression. If the perimeters are the same, then the depression will have a rectangular square shape. If the upper perimeter 371 has a greater dimension than the bottom perimeter 352, then the depression will have an inverted truncated pyramid shape. Diamond may be bonded on a substrate as depicted in FIG. 3U in a table that has a thickness that completely covers the outside surface of the substrate. In that case the diamond table will be thicker in areas above a depression than in other areas. If such a diamond table is used, then from outward appearance, the substrate surface topographical features will not be discernible. Alternatively, diamond may be bonded in the depressions only, leaving the substrate between depressions exposed.

Although many substrate topographies have been depicted in convex spherical substrates, those surface topographies may be applied to convex spherical substrate surfaces, other non-planar substrate surfaces, and flat substrate surfaces. Substrate surface topographies which are variations or modifications of those shown, and other substrate topographies which increase component strength or durability may also be used.

Diamond Feedstock Selection

It is anticipated that typically the diamond particles used will be in the range of less than 1 micron to more than 100 microns. In some embodiments of the invention, however, diamond particles as small as 1 nanometer may be used. Smaller diamond particles are preferred for smoother bearing surfaces. Commonly, diamond particle sizes will be in the range of 0.5 to 2.0 microns or 0.1 to 10 microns. It is preferred that the diamond particles will be roughly spherical in some embodiments of the invention. The diamond feedstock may include the addition of various metals as desired and as discussed elsewhere, such as SiC, $SiN_2$, TiN, $TB_2$ and others. A preferred diamond feedstock is shown in the table below.

TABLE 3

EXAMPLE BIMODAL DIAMOND FEEDSTOCK

| MATERIAL | AMOUNT |
|---|---|
| 4 to 8 micron diamond | about 90% |
| 0.5 to 1.0 micron diamond | about 9% |
| Titanium carbonitride powder | about 1% |

This formulation mixes some smaller and some larger diamond crystals so that during sintering, the small crystals may dissolve and then recrystallize in order to form a lattice structure with the larger diamond crystals. Titanium carbonitride powder may optionally be included in the diamond feedstock in order to prevent excessive diamond grain growth during sintering in order to produce a finished product that has smaller diamond crystals.

Another diamond feedstock example is provided in the table below.

TABLE 4

EXAMPLE TRIIMODAL DIAMOND FEEDSTOCK

| MATERIAL | AMOUNT |
|---|---|
| Size x diamond crystals | about 90% |
| Size 0.1x diamond crystals | about 9% |
| Size 0.01x diamond crystals | about 1% |

The trimodal diamond feedstock described above can be used with any suitable diamond feedstock having a first size or diameter "x", a second size 0.1x and a third size 0.01x. This ratio of diamond crystals allows packing of the feedstock to about 89% theoretical density, closing most interstitial spaces and providing the densest diamond table in the finished polycrystalline diamond compact.

Another diamond feedstock example is provided in the table below.

TABLE 5

EXAMPLE TRIIMODAL DIAMOND FEEDSTOCK

| MATERIAL | AMOUNT |
|---|---|
| Size x diamond crystals | about 88-92% |
| Size 0.1x diamond crystals | about 8-12% |
| Size 0.01x diamond crystals | about 0.8-1.2% |

Another diamond feedstock example is provided in the table below.

TABLE 6

EXAMPLE TRIIMODAL DIAMOND FEEDSTOCK

| MATERIAL | AMOUNT |
|---|---|
| Size x diamond crystals | about 85-95% |
| Size 0.1x diamond crystals | about 5-15% |
| Size 0.01x diamond crystals | about 0.5-1.5% |

Another diamond feedstock example is provided in the table below.

TABLE 7

EXAMPLE TRIIMODAL DIAMOND FEEDSTOCK

| MATERIAL | AMOUNT |
|---|---|
| Size x diamond crystals | about 80-90% |
| Size 0.1x diamond crystals | about 10-20% |
| Size 0.01x diamond crystals | about 0-2% |

In some embodiments of the invention, the diamond feedstock used will be diamond powder having a greatest dimension of about 100 nanometers or less. In some embodiments of the invention it is preferred to include some solvent-catalyst metal with the diamond feedstock to aid in the sintering process, although in many applications there will be a significant solvent-catalyst metal sweep from the substrate during sintering as well.

Solvent Metal Selection

It has already been mentioned that solvent metal will sweep from the substrate through the diamond feedstock during sintering in order to solvate some diamond crystals so that they may later recrystallize and form a diamond-diamond bonded lattice network that characterizes polycrystalline diamond. It is preferred, however, to include some solvent-catalyst metal in the diamond feedstock only when required to supplement the sweep of solvent-catalyst metal from the substrate.

Traditionally, cobalt, nickel and iron have been used as solvent metals for making polycrystalline diamond. In bearing components, however, the solvent metal must be biocompatible. The inventors prefer use of a solvent metal such as CoCrMo or CoCrW. Platinum and other materials could also be used for a binder.

It is important not just to add the solvent metal to diamond feedstock, but also to include solvent metal in an appropriate proportion and to mix it evenly with the feedstock. The inventors prefer the use of about 86% diamond feedstock and 15% solvent metal by mass (weight), but anticipate that useful ratios of diamond feedstock to solvent metal will include 5:95, 10:90, 20:80, 30:70, 40:60, 50:50, 60:40, 65:35, 75:25, 80:20, 90:10, 95:5, 97:3, 98:2, 99:1, 99.5:0.5, 99.7:0.3, 99.8:0.2, 99.9:0.1 and others.

In order to mix the diamond feedstock with solvent-catalyst metal, first the amounts of feedstock and solvent metal to be mixed may be placed together in a mixing bowl, such as a mixing bowl made of the desired solvent-catalyst metal. Then the combination of feedstock and solvent metal may be mixed at an appropriate speed (such as 200 rpm) with dry methanol and attritor balls for an appropriate time period, such as 30 minutes. The attritor balls, the mixing fixture and the mixing bowl are preferably made from the solvent-catalyst metal. The methanol may then be decanted and the diamond feedstock separated from the attritor balls. The feedstock may then be dried and cleaned by firing in a molecular hydrogen furnace at about 1000 degrees Celsius for about 1 hour. The feedstock is then ready for loading and sintering. Alternatively, it may be stored in conditions which will preserve its cleanliness. Appropriate furnaces which may be used for firing also include hydrogen plasma furnaces and vacuum furnaces.

Loading Diamond Feedstock

The loading technique for diamond feedstock used is critical to the success of the final product. As mentioned previously, the diamond feedstock must be loaded to uniform density in order to produce a component that lacks unwanted distortion.

Figure 7:
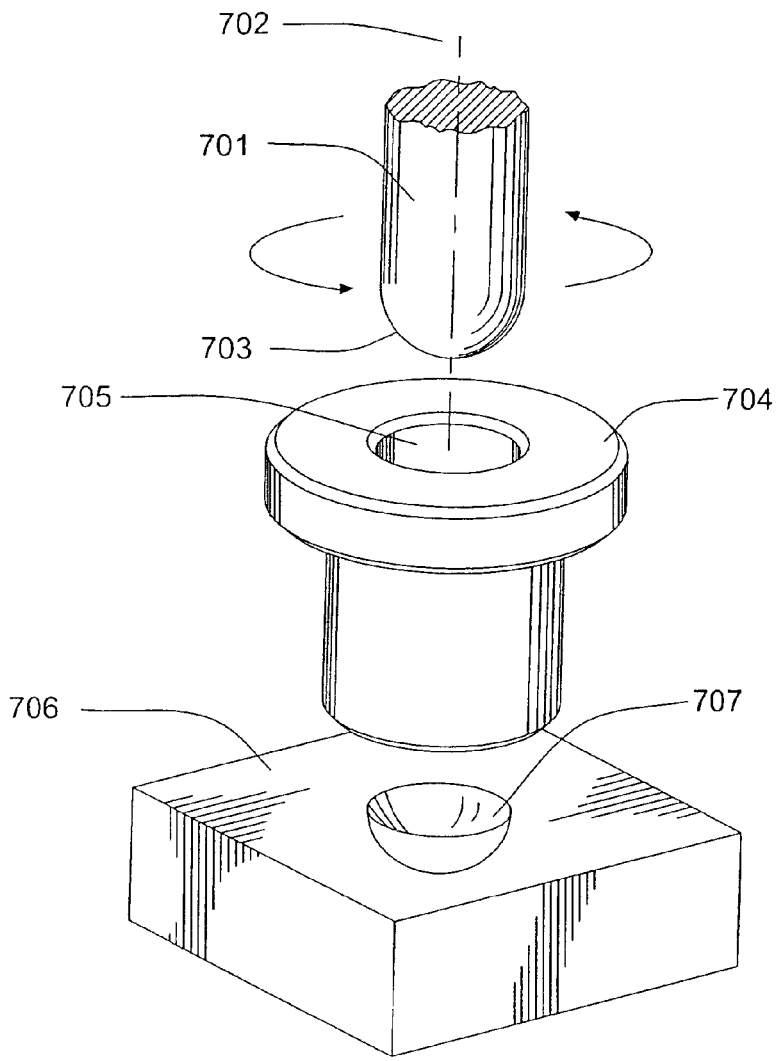
FIG. 7 depicts a device, which may be used for loading diamond feedstock prior to sintering.

Referring to FIG. 7, an apparatus for carrying out a preferred loading technique is depicted. The apparatus includes a spinning rod 701 with a longitudinal axis 702, the spinning rod being capable of spinning about its longitudinal axis. The spinning rod 701 has an end 703 matched to the size and shape of the part to be manufactured. For example, if the part to be manufactured is a head or an cup or race, the spinning rod end 703 should be hemispherical.

A compression ring 704 is provided with a bore 705 through which the spinning rod 701 may project. A die 706 or can is provided with a cavity 707 also matched to the size and shape of the part to be made.

In order to load diamond feedstock, the spinning rod is placed into a drill chuck and the spinning rod is aligned with the center point of the die. The depth to which the spinning rod stops in relation to the cavity of the die is controlled with a set screw and monitored with a dial indicator.

The die is charged with a known amount of diamond feedstock material. The spinning rod is then spun about its longitudinal axis and lowered into the die cavity to a predetermined depth. The spinning rod contacts and rearranges the diamond feedstock during this operation. Then the spinning of the spinning rod is stopped and the spinning rod is locked in place.

The compression ring is then lowered around the outside of the spinning rod to a point where the compression ring contacts diamond feedstock in the cavity of the die. The part of the compression ring that contacts the diamond is annular. The compression ring is tamped up and down to compact the diamond. This type of compaction is used to distribute diamond material throughout the cavity to the same density and may be done in stages to prevent bridging. Packing the diamond with the compaction ring causes the density of the diamond around the equator of the sample caused to be very uniform and the same as that of the polar region in the cavity. In this configuration, the diamond sinters in a truly spherical fashion and the resulting part maintains its sphericity to close tolerances.

Another method which may be employed to maintain a uniform density of the feedstock diamond is the use of a binder. A binder is added to the correct volume of feedstock diamond, and then the combination is pressed into a can. Some binders which might be used include polyvinyl butyryl, polymethyl methacrylate, polyvinyl formol, polyvinyl chloride acetate, polyethylene, ethyl cellulose, methylabietate, paraffin wax, polypropylene carbonate and polyethyl methacrylate.

In a preferred embodiment of the invention, the process of binding diamond feedstock includes four steps. First, a binder solution is prepared. A binder solution may be prepared by adding about 5 to 25% plasticizer to pellets of poly(propylene carbonate), and dissolving this mixture in solvent such as 2-butanone to make about a 20% solution by weight.

Plasticizers that may be used include nonaqueous binders generally, glycol, dibutyl phthalate, benzyl butyl phthalate, alkyl benzyl phthalate, diethylhexyl phthalate, diisoecyl phthalate, diisononyl phthalate, dimethyl phthalate, dipropylene glycol dibenzoate, mixed glycols dibenzoate, 2-ethylhexyl diphenyl dibenzoate, mixed glycols dibenzoate, 2-ethylhexyl diphenyl phosphate, isodecyl diphenyl phosphate, isodecyl diphenl phosphate, tricrestyl phosphate, tributoxy ethyl phosphate, dihexyl adipate, triisooctyl trimellitate, dioctyl phthalate, epoxidized linseed oil, epoxidized soybean oil, acetyl triethyl citrate, propylene carbonate, various phthalate esters, butyl stearate, glycerin, polyalkyl glycol derivatives, diethyl oxalate, paraffin wax and triethylene glycol. Other appropriate plasticizers may be used as well.

Solvents that may be used include 2-butanone, methylene chloride, chloroform, 1,2-dichloroethne, trichlorethylene, methyl acetate, ethyl acetate, vinyl acetate, propylene carbonate, n-propyl acetate, acetonitrile, dimethylformamide, propionitrile, n-methyl-2-pyrrolidene, glacial acetic acid, dimethyl sulfoxide, acetone, methyl ethyl ketone, cyclohexanone, oxysolve 80a, caprotactone, butyrolactone, tetrahydrofuran, 1,4 dioxane, propylene oxide, cellosolve acetate, 2-methoxy ethyl ether, benzene, styrene, xylene, ethanol, methanol, toluene, cyclohexane, chlorinated hydrocarbons, esters, ketones, ethers, ethyl benzene and various hydrocarbons. Other appropriate solvents may be used as well.

Second, diamond is mixed with the binder solution. Diamond may be added to the binder solution to achieve about a 2-25% binder solution (the percentage is calculated without regard to the 2-butanone).

Third, the mixture of diamond and binder solution is dried. This may be accomplished by placing the diamond and binder solution mixture in a vacuum oven for about 24 hours at about 50 degrees Celsius in order to drive out all of the solvent 2-butanone. Fourth, the diamond and binder may be pressed into shape. When the diamond and binder is removed from the oven, it will be in a clump that may be broken into pieces which are then pressed into the desired shape with a compaction press. A pressing spindle of the desired geometry may be contacted with the bound diamond to form it into a desired shape. When the diamond and binder have been pressed, the spindle is retracted. The preferred final density of diamond and binder after pressing is at least about 2.6 grams per cubic centimeter.

Figure 7A:
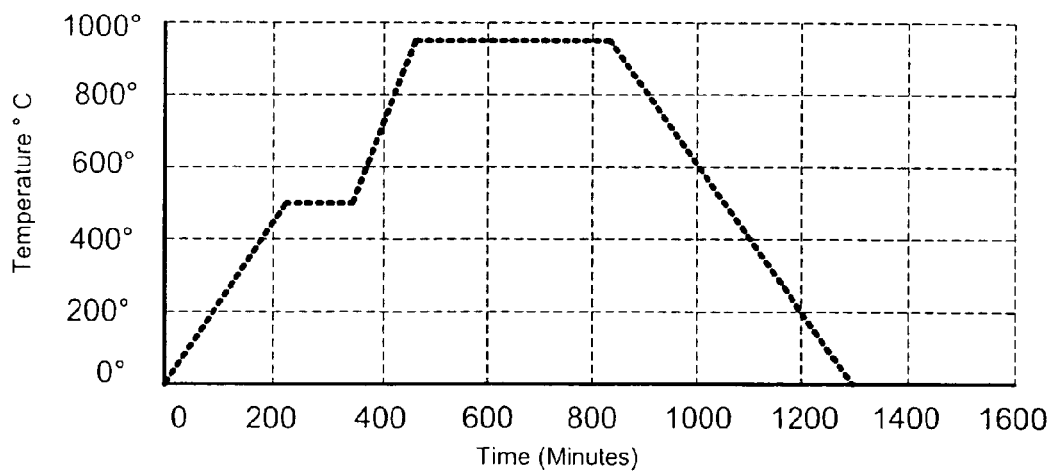
FIG. 7A depicts a furnace cycle for removal of a binder material from diamond powder or grit feedstock prior to sintering.

If a volatile binder is used, it should be removed from the shaped diamond prior to sintering. The shaped diamond is placed into a furnace and the binding agent is either gasified or pyrolized for a sufficient length of time such that there is no binder remaining. Polycrystalline diamond compact quality is reduced by foreign contamination of the diamond or substrate, and great care must be taken to ensure that contaminants and binder are removed during the furnace cycle. Ramp up and the time and temperature combination are critical for effective pyrolization of the binder. For the binder example given above, the debinding process preferably used to remove the binder is as follows. Reviewing FIG. 7A while reading this description may be helpful.

First, the shaped diamond and binder are heated to from ambient temperature to about 500 degrees Celsius. The temperature is preferably increased by about 2 degrees Celsius per minute until about 500 degrees Celsius is reached. Second, the temperature of the bound and shaped diamond is maintained at about 500 degrees Celsius for about 2 hours. Third, the temperature of the diamond is increased again. The temperature is preferably increased from about 500 degrees Celsius by about 4 degrees per minute until a temperature of about 950 degrees Celsius is reached. Fourth, the diamond is maintained at about 950 degrees Celsius for about 6 hours. Fifth, the diamond is then permitted to return to ambient temperature at a temperature decrease of about 2 degrees per minute.

In some embodiments of the invention, it may be desirable to preform bound diamond feedstock by an appropriate process, such as injection molding. The diamond feedstock may include diamond crystals of one or more sizes, solvent-catalyst metal, and other ingredients to control diamond recrystallization and solvent-catalyst metal distribution. Handling the diamond feedstock is not difficult when the desired final curvature of the part is flat, convex dome or conical. However, when the desired final curvature of the part has complex contours, such as illustrated herein, providing uniform thickness and accuracy of contours of the polycrystalline diamond compact is more difficult when using powder diamond feedstock. In such cases it may be desirable to perform the diamond feedstock before sintering.

If it is desired to perform diamond feedstock prior to loading into a can for sintering, rather than placing powder diamond feedstock into the can, the steps described herein and variations of them may be followed. First, as already described, a suitable binder is added to the diamond feedstock. Optionally, powdered solvent-catalyst metal and other components may be added to the feedstock as well. The binder will typically be a polymer chosen for certain characteristics, such as melting point, solubility in various solvents, and CTE. One or more polymers may be included in the binder. The binder may also include an elastomer and/or solvents as desired in order to achieve desired binding, fluid flow and injection molding characteristics. The working volume of the binder to be added to a feedstock preferably will be equal to or slightly more than the measured volume of empty space in a quantity of lightly compressed powder. Since binders typically consist of materials such as organic polymers with relatively high CTE's, the working volume should be calculated for the injection molding temperatures expected. The binder and feedstock should be mixed thoroughly to assure uniformity of composition. When heated, the binder and feedstock will have sufficient fluid character to flow in high pressure injection molding. The heated feedstock and binder mixture is then injected under pressure into molds of desired shape. The molded part then cools in the mold until set, and the mold can then be opened and the part removed. Depending on the final polycrystalline diamond compact geometry desired, one or more molded diamond feedstock component can be created and placed into a can for polycrystalline diamond compact sintering. Further, use of this method permits diamond feedstock to be molded into a desired form and then stored for long periods of time prior to use in the sintering process, thereby simplifying manufacturing and resulting in more efficient production.

As desired, the binder may be removed from the injection molded diamond feedstock form. A variety of methods are available to achieve this. For example, by simple vacuum or hydrogen furnace treatment, the binder may be removed from the diamond feedstock form. In such a method, the form would be brought up to a desired temperature in a vacuum or in a very low pressure hydrogen (reducing) environment. The binder will then volatilize with increasing temperature and will be removed from the form. The form may then be removed from the furnace. When hydrogen is used, it helps to maintain extremely clean and chemically active surfaces on the diamond crystals of the diamond feedstock form.

An alternative method for removing the binder from the form involves utilizing two or polymer (such as polyethylene) binders with different molecular weights. After initial injection molding, the diamond feedstock form is placed in a solvent bath which removes the lower molecular weight polymer, leaving the higher molecular weight polymer to maintain the shape of the diamond feedstock form. Then the diamond feedstock form is placed in a furnace for vacuum or very low pressure hydrogen treatment for removal of the higher molecular weight polymer.

Partial or complete binder removal from the diamond feedstock form may be performed prior to assembly of the form in a pressure assembly for polycrystalline diamond compact sintering. Alternatively, the pressure assembly including the diamond feedstock form may be placed into a furnace for vacuum or very low pressure hydrogen furnace treatment and binder removal.

Diamond feedstock may be selected and loaded in order to create different types of gradients in the diamond table. These include an interface gradient diamond table, an incremental gradient diamond table, and a continuous gradient diamond table.

If a single type or mix of diamond feedstock is loaded adjacent a substrate, as discussed elsewhere herein, sweep of solvent-catalyst metal through the diamond will create an interface gradient in the gradient transition zone of the diamond table.

An incremental gradient diamond table may be created by loading diamond feedstocks of differing characteristics (diamond particle size, diamond particle distribution, metal content, etc.) in different strata or layers before sintering. For example, a substrate is selected, and a first diamond feedstock containing 60% solvent-catalyst metal by weight is loaded in a first strata adjacent the substrate. Then a second diamond feedstock containing 40% solvent-catalyst metal by weight is loaded in a second strata adjacent the first strata. Optionally, additional strata of diamond feedstock may be used. For example, a third strata of diamond feedstock containing 20% solvent-catalyst metal by weight may be loaded adjacent the second strata.

A continuous gradient diamond table may be created by loading diamond feedstock in a manner that one or more of its characteristics continuously vary from one depth in the diamond table to another. For example, diamond particle size may vary from large near a substrate (in order to create large interstitial spaces in the diamond for solvent-catalyst metal to sweep into) to small near the diamond bearing surface in order to create a part that is strongly bonded to the substrate but that has a very low friction bearing surface.

The diamond feedstocks of the different strata may be of the same or different diamond particle size and distribution. Solvent-catalyst metal may be included in the diamond feedstock of the different strata in weight percentages of from about 0% to more than about 80%. In some embodiments, diamond feedstock will be loaded with no solvent-catalyst metal in it, relying on sweep of solvent-catalyst metal from the substrate to achieve sintering. Use of a plurality of diamond feedstock strata, the strata having different diamond particle size and distribution, different solvent-catalyst metal by weight, or both, allows a diamond table to be made that has different physical characteristics at the interface with the substrate than at the load bearing and articulation surface. This allows a polycrystalline diamond compact to be manufactured which has a diamond table very firmly bonded to its substrate, and which has very favorable characteristics at the load bearing and articulation surface in order to achieve low friction articulation, impact resistance, and durability.

Reduction of Free Volume in Diamond Feedstock

As mentioned earlier, it may be desirable to remove free volume in the diamond feedstock before sintering is attempted. The inventors have found this is a useful procedure when producing spherical concave and convex parts. If a press with sufficient anvil travel is used for high pressure and high temperature sintering, however, this step may not be necessary. Preferably free volume in the diamond feedstock will be reduced so that the resulting diamond feedstock is at least about 95% theoretical density and preferably closer to about 97% of theoretical density.

Referring to FIGS. 8 and 8A, an assembly used for pre-compressing diamond to eliminate free volume is depicted. In the drawing, the diamond feedstock is intended to be used to make a convex spherical polycrystalline diamond part. The assembly may be adapted for precompressing diamond feedstock for making polycyrstalline diamond compacts of other complex shapes.

The assembly depicted includes a cube 801 of a pressure transfer medium. A cube is made from pyrophillite or other appropriate pressure transfer material such as a synthetic pressure medium and is intended to undergo pressure from a cubic press with anvils simultaneously pressing the six faces of the cube. A cylindrical cell rather than a cube would be used if a belt press were utilized for this step.

The cube 801 has a cylindrical cavity 802 or passage through it. The center of the cavity 802 will receive a spherical refractory metal can 810 loaded with diamond feedstock 806 that is to be precompressed. The diamond feedstock 806 may have a substrate with it.

The can 810 consists of two hemispherical can halves 810*a* and 810*b*, one of which overlaps the other to form a slight lip 812. The can is preferably an appropriate refractory metal such as niobium, tantalum, molybdenum, etc. The can is typically two hemispheres, one which is slightly larger to accept the other being slid inside of it to fully enclosed the diamond feedstock. A rebated area or lip is provided in the larger can so that the smaller can will satisfactorily fit therein. The seam of the can is sealed with an appropriate sealant such as dry hexagonal boronitride or a synthetic compression medium. The sealant forms a barrier that prevents the salt pressure medium from penetrating the can. The can seam may also be welded by plasma, laser, or electron beam processes.

An appropriately shaped pair of salt domes 804 and 807 surround the can 810 containing the diamond feedstock 806. In the example shown, the salt domes each have a hemispherical cavity 805 and 808 for receiving the can 810 containing the spherical diamond feedstock 806. The salt domes and the can and diamond feedstock are assembled together so that the salt domes encase the diamond feedstock. A pair of cylindrical salt disks 803 and 809 are assembled on the exterior of the salt domes 804 and 807. All of the aforementioned components fit within the bore 802 of the pressure medium cube 801.

The entire pyrocube assembly is placed into a press and pressurized under appropriate pressure (such as about 40-68 Kbar) and for an appropriate although brief duration to pre-compress the diamond and prepare it for sintering. No heat is necessary for this step.

g. Prepare Heater Assembly

In order to sinter the assembled and loaded diamond feedstock described above into polycrystalline diamond, both heat and pressure are required. Heat is provided electrically as the part undergoes pressure in a press. A prior art heater assembly is used to provide the required heat.

A refractory metal can containing loaded and precompressed diamond feedstock is placed into a heater assembly. Salt domes are used to encase the can. The salt domes used are preferably white salt (NaCl) that is precompressed to at least about 90-95% of theoretical density. This density of the salt is desired to preserve high pressures of the sintering system and to maintain geometrical stability of the manufactured part. The salt domes and can are placed into a graphite heater tube assembly. The salt and graphite components of the heater assembly are preferably baked in a vacuum oven at greater than 100 degrees Celsius and at a vacuum of at least 23 torr for about 1 hour in order to eliminate adsorbed water prior to loading in the heater assembly. Other materials which may be used in construction of a heater assembly include solid or foil graphite, amorphous carbon, pyrolitic carbon, refractory metals and high electrical resistant metals.

Once electrical power is supplied to the heater tube, it will generate heat required for polycrystalline diamond formation in the high pressure/high temperature pressing operation.

h. Preparation of Pressure Assembly for Sintering

Once a heater assembly has been prepared, it is placed into a pressure assembly for sintering in a press under high pressure and high temperature. A cubic press or a belt press may be used for this purpose, with the pressure assembly differing somewhat depending on the type of press used. The pressure assembly is intended to receive pressure from a press and transfer it to the diamond feedstock so that sintering of the diamond may occur under isostatic conditions.

If a cubic press is used, then a cube of suitable pressure transfer media such as pyrophillite will contain the heater assembly. Cell pressure medium would be used if sintering were to take place in a belt press. Salt may be used as a pressure transfer media between the cube and the heater assembly. Thermocouples may be used on the cube to monitor temperature during sintering. The cube with the heater assembly inside of it is considered a pressure assembly, and is place into a press a press for sintering.

i. Sintering of Feedstock into Polycrystalline Diamond

Figure 8B:
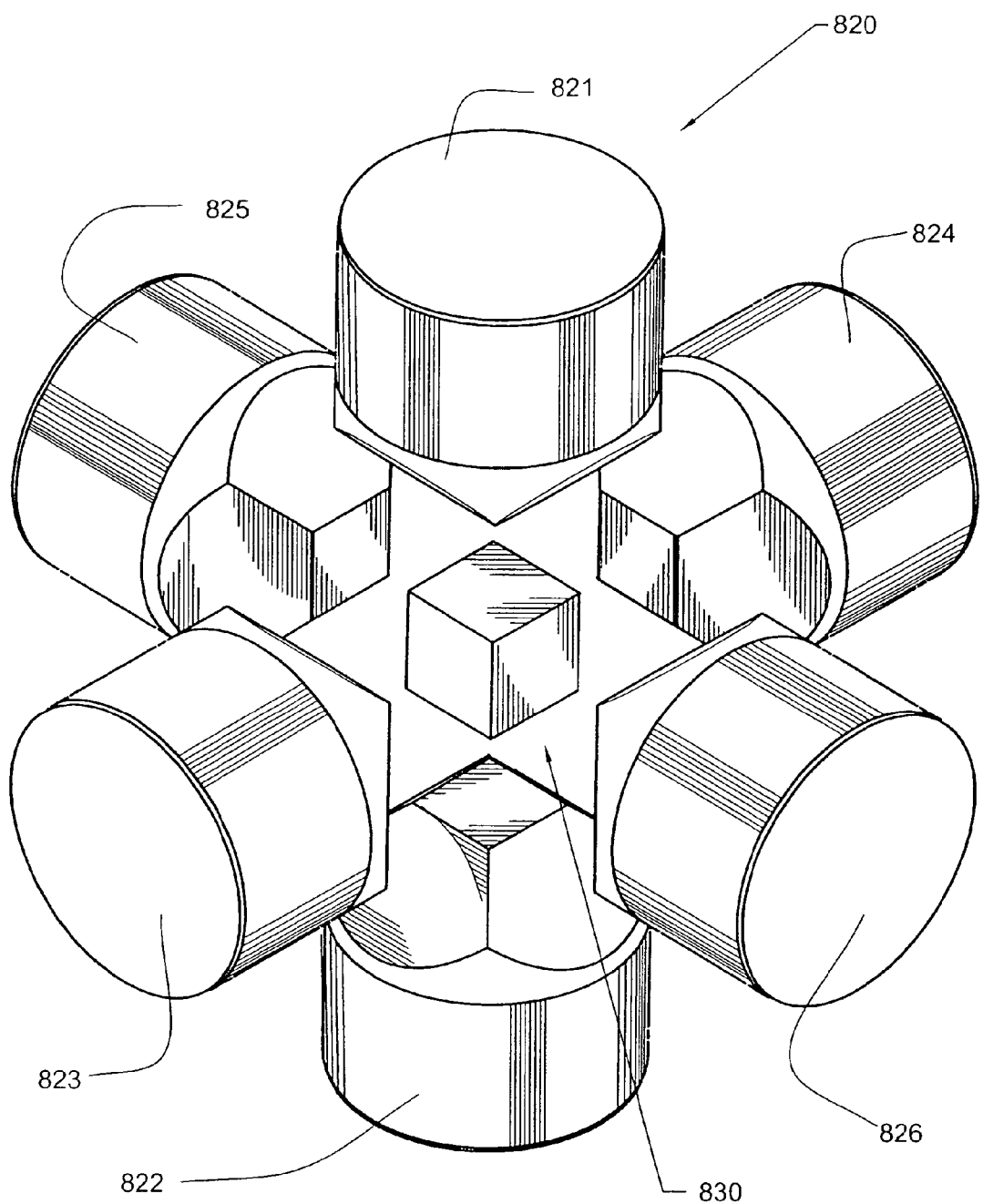
FIG. 8B depicts anvils of a cubic press that could be used to sinter diamond.

The pressure assembly described above containing a refractory metal can that has diamond feedstock loaded and precompressed within is placed into an appropriate press. The type of press preferably used at the time of the invention is a cubic press (i.e., the press has six anvil faces) for transmitting high pressure to the assembly along 3 axes from six different directions. Alternatively, a belt press and a cylindrical cell can be used to obtain similar results. Referring to FIG. 8B, a representation of the 6 anvils of a cubic press 820 is provided. The anvils 821, 822, 823, 824, 825 and 826 are situated around a pressure assembly 830.

To prepare for sintering, the entire pressure assembly is loaded into a cubic press and initially pressurized to about 40-68 Kbars. The pressure to be used depends on the product to be manufactured and must be determined empirically. Then electrical power is added to the pressure assembly in order to reach a temperature preferably in the range of less than about 1145 or 1200 to more than about 1500 degrees Celsius. Preferably about 5800 watts of electrical power is available at two opposing anvil faces, creating the current flow required for the heater assembly to generate the desired level of heat. Once the desired temperature is reached, the pressure assembly is subjected to pressure of about 1 million pounds per square inch at the anvil face. The components of the pressure assembly transmit pressure to the diamond feedstock. These conditions are maintained for preferably about 3-12 minutes, but could be from less than 1 minute to more than 30 minutes. The sintering of polycrystalline diamond compacts takes place in an isostatic environment where the pressure transfer components are permitted only to change in volume but are not permitted to otherwise deform. Once the sintering cycle is complete, about a 90 second cool down period is allowed, and then pressure is removed. The polycrystalline diamond compact is then removed for finishing.

Removal of a sintered polycrystalline diamond compact having a curved, compound or complex shape from a pressure assembly is simple due to the differences in material properties between diamond and the surrounding metals in preferred embodiments of the invention. This is generally referred to as the mold release system of the invention.

One or more of the following component processes is incorporated into the mold release system:

An intermediate layer of material between the polycrystalline diamond compact part and the mould that prevents bonding of the polycrystalline diamond compact to the mould surface.

A mold material that does not bond to the polycrystalline diamond compact under the conditions of synthesis.

A mold material that, in the final stages of, or at the conclusion of, the polycrystalline diamond compact synthesis cycle either contracts away from the polycrystalline diamond compact in the case of a net concave polycrystalline diamond compact geometry, or expands away from the polycrystalline diamond compact in the case of a net convex polycrystalline diamond compact geometry.

The mold shape can also act, simultaneously as a source of sweep metal useful in the polycrystalline diamond compact synthesis process.

As an example, below is a discussion of use of a mold release system in manufacturing a polycrystalline diamond compact by employing a negative shape of the desired geometry to produce hemispherical cup or races. The mold surface contracts away from the final net concave geometry, the mold surface acts as a source of solvent-catalyst metal for the polycrystalline diamond compact synthesis process, and the mold surface has poor bonding properties to polycrystalline diamond compacts.

In the case of forming concave hemispherical cup or races such as are used for articulating surfaces in ball and socket bearing components, two different methods have been employed. In the first method, one, a mold consisting of a cobalt chrome (ASTM F-799) ball is used as a substrate around which a layer of polycrystalline diamond compact feedstock material is placed, contained by an outer can. A separator ring composed of a material such as mica or compressed hexagonal boron nitride (HBN) is positioned at the hemisphere of the mold ball to allow separation of the two concave hemispherical polycrystalline diamond compact parts at the conclusion of the synthesis process. During the polycrystalline diamond compact synthesis process, the cobalt-chrome ball expands in size due to the increase in temperature intrinsic to the process. It also can supply solvent-catalyst sweep metal to the polycrystalline diamond compact synthesis process.

After the polycrystalline diamond compact shell has formed around the mold ball, the ball separates from the two hemispherical polycrystalline diamond compact cup or races as it contracts on cooling and pressure reduction. The forces of the shrinking CoCr ball will exceed the bond strength of diamond to the CoCr, providing a fairly clean separation and a smooth polycrystalline diamond cup or race adjacent a detached spherical CoCr ball.

As an alternative, it is possible to use an intermediate layer of material between the polycrystalline diamond compact part and the mold surface. The intermediate material should be a material which contracts away from the final net concave polycrystalline diamond compact geometry to achieve mold separation with the polycrystalline diamond compact.

The second mold release method for use in forming a hemispherical cup or race is similar to the first method. However, in the second method, the mold is a cobalt-cemented tungsten carbide ball or sphere that has been coated with a thin layer of hexagonal boron nitride. During the polycrystalline diamond compact synthesis process, the tungsten carbide ball expands in size due to the increase in temperature intrinsic to the process. After the polycrystalline diamond compact shell has formed around the mold ball, the mold ball separates from the two hemispherical polycrystalline diamond compact cup or races as it contracts on cooling. The hexagonal boron nitride prevents bonding between the polycrystalline diamond compact layer and the tungsten carbide ball and a clean separation is achieved.

j. Removal of Solvent-Catalyst Metal from PCD

If desired, the solvent-catalyst metal remaining in interstitial spaces of the sintered polycrystalline diamond may be removed. Such removal is accomplished by chemical leaching as is known in the art. After solvent-catalyst metal has been removed from the interstitial spaces in the diamond table, the diamond table will have greater stability at high temperatures. This is because there is no catalyst for the diamond to react with and break down. Removal of solvent-catalyst metal from interstitial spaces in the diamond may also be desirable if the solvent-catalyst material is not biocompatible.

After leaching solvent-catalyst metal from the diamond table, it may be replaced by another metal, metal or metal compound in order to form thermally stable diamond that is stronger than leached polycrystalline diamond. If it is intended to weld synthetic diamond or a polycrystalline diamond compact to a substrate or to another surface such as by inertia welding, it may be desirable to use thermally stable diamond due to its resistance to heat generated by the welding process.

3. Finishing Methods and Apparatuses

Once a polycrystalline diamond compact has been sintered, a mechanical finishing process is preferably employed to prepare the final product. The preferred finishing steps explained below are described with respect to finishing a polycrystalline diamond compact, but they could be used to finish any other bearing surface or any other type of component.

Prior to the invention herein, the synthetic diamond industry was faced with the problem of finishing flat surfaces and thin edges of diamond compacts. Methods for removal of large amounts of diamond from spherical surfaces or finishing those surfaces to high degrees of accuracy for sphericity, size and surface finish had not been developed in the prior art.

a. Finishing of Superhard Cylindrical and Flat Forms

In order to provide a greater perspective on the most preferred finishing techniques for curved and spherical superhard surfaces, a description of other finishing techniques is provided.

1. Lapping

A wet slurry of diamond grit on cast iron or copper rotating plates are used to remove material on larger flat surfaces (e.g., up to about 70 mm. in diameter). End coated cylinders of size ranging from about 3 mm to about 70 mm may also be lapped to create flat surfaces. Lapping is generally slow and not dimensionally controllable for depth and layer thickness, although flatness and surface finishes can be held to very close tolerances.

2. Grinding

Diamond impregnated grinding wheels are used to shape cylindrical and flat surfaces. Grinding wheels are usually resin bonded in a variety of different shapes depending on the type of material removal required (i.e., cylindrical centerless grinding or edge grinding). Polycrystalline diamond compacts are difficult to grind, and large polycrystalline diamond compact surfaces are nearly impossible to grind. Consequently, it is desirable to keep grinding to a minimum, and grinding is usually confined to a narrow edge or perimeter or to the sharpening of a sized PDC end-coated cylinder or machine tool insert.

3. Electro Spark Discharge Grinding (EDG)

Rough machining of polycrystalline diamond compact may be accomplished with electro spark discharge grinding ("EDG") on large diameter (e.g., up to about 70 mm.) flat surfaces. This technology typically involves the use of a rotating carbon wheel with a positive electrical current running against a polycrystalline diamond compact flat surface with a negative electrical potential. The automatic controls of the EDG machine maintain proper electrical erosion of the polycrystalline diamond compact material by controlling variables such as spark frequency, voltage and others. EDG is typically a more efficient method for removing larger volumes of diamond than lapping or grinding. After EDG, the surface must be finish lapped or ground to remove what is referred to as the heat affected area or re-cast layer left by EDG.

4. Wire Electrical Discharge Machining (WEDM)

WEDM is used to cut superhard parts of various shapes and sizes from larger cylinders or flat pieces. Typically, cutting tips and inserts for machine tools and re-shaping cutters for oil well drilling bits represent the greatest use for WEDM in PDC finishing.

5. Polishing

Polishing superhard surfaces to very high tolerances may be accomplished by diamond impregnated high speed polishing machines. The combination of high speed and high friction temperatures tends to burnish a PDC surface finished by this method, while maintaining high degrees of flatness, thereby producing a mirror-like appearance with precise dimensional accuracy.

b. Finishing a Spherical Geometry.

Finishing a spherical surface (concave spherical or convex spherical) presents a greater problem than finishing a flat surface or the rounded edge of a cylinder. The total surface area of a sphere to be finished compared to the total surface area of a round end of a cylinder of like radius is four (4) times greater, resulting in the need to remove four (4) times the amount of polycrystalline diamond compact material. The nature of a spherical surface makes traditional processing techniques such as lapping, grinding and others unusable because they are adapted to flat and cylindrical surfaces. The contact point on a sphere should be point contact that is tangential to the edge of the sphere, resulting in a smaller amount of material removed per unit of time, and a proportional increase in finishing time required. Also, the design and types of processing equipment and tooling required for finishing spherical objects must be more accurate and must function to closer tolerances than those for other shapes. Spherical finishing equipment also requires greater degrees of adjustment for positioning the workpiece and tool ingress and egress.

The following are steps that may be performed in order to finish a spherical, rounded or arcuate surface.

1. Rough Machining

It is preferred to initially rough out the dimensions of the surface using a specialized electrical discharge machining apparatus. Referring to FIG. 9, roughing a polycrystalline diamond compact sphere 903 is depicted. A rotator 902 is provided that is continuously rotatable about its longitudinal axis (the z axis depicted). The sphere 903 to be roughed is attached to a spindle of the rotator 902. An electrode 901 is provided with a contact end 901A that is shaped to accommodate the part to be roughed. In this case the contact end 901A has a partially spherical shape. The electrode 901 is rotated continuously about its longitudinal axis (the y axis depicted). Angular orientation of the longitudinal axis y of the electrode 901 with respect to the longitudinal axis z of the rotator 902 at a desired angle β is adjusted to cause the electrode 901 to remove material from the entire spherical surface of the ball 903 as desired.

Thus, the electrode 901 and the sphere 903 are rotating about different axes. Adjustment of the axes can be used to achieve near perfect spherical movement of the part to be roughed. Consequently, a nearly perfect spherical part results from this process. This method produces polycrystalline diamond compact spherical surfaces with a high degree of sphericity and cut to very close tolerances. By controlling the amount of current introduced to the erosion process, the depth and amount of the heat affected zone can be minimized. In the case of a polycrystalline diamond compact, the heat affected zone can be kept to about 3 to 5 microns in depth and is easily removed by grinding and polishing with diamond impregnated grinding and polishing wheels.

Referring to FIG. 10, roughing a convex spherical polycrystalline diamond compact 1003 such as an acetablular cup or race is depicted. A rotator 1002 is provided that is continuously rotatable about its longitudinal axis (the z axis depicted). The part 1003 to be roughed is attached to a spindle of the rotator 1002. An electrode 1001 is provided with a contact end 1001A that is shaped to accommodate the part to be roughed. The electrode 1001 is continuously rotatable about its longitudinal axis (the y axis depicted). Angular orientation of the longitudinal axis y of the electrode 1001 with respect to the longitudinal axis z of the rotator 1002 at a desired angle β is adjusted to cause the electrode 1001 to remove material from the entire spherical surface of the cup or race 1003 as desired.

In some embodiments of the invention, multiple electro discharge machine electrodes will be used in succession in order to machine a part. A battery of electro discharge machines may be employed to carry this out in assembly line fashion.

2. Finish Grinding and Polishing

Once the spherical surface (whether concave or convex) has been rough machined as described above or by other methods, finish grinding and polishing of a part can take place. Grinding is intended to remove the heat affected zone in the polycrystalline diamond compact material left behind by electrodes. Use of the same rotational geometry as depicted in FIGS. 9 and 10 allows sphericity of the part to be maintained while improving its surface finish characteristics.

Figure 11:
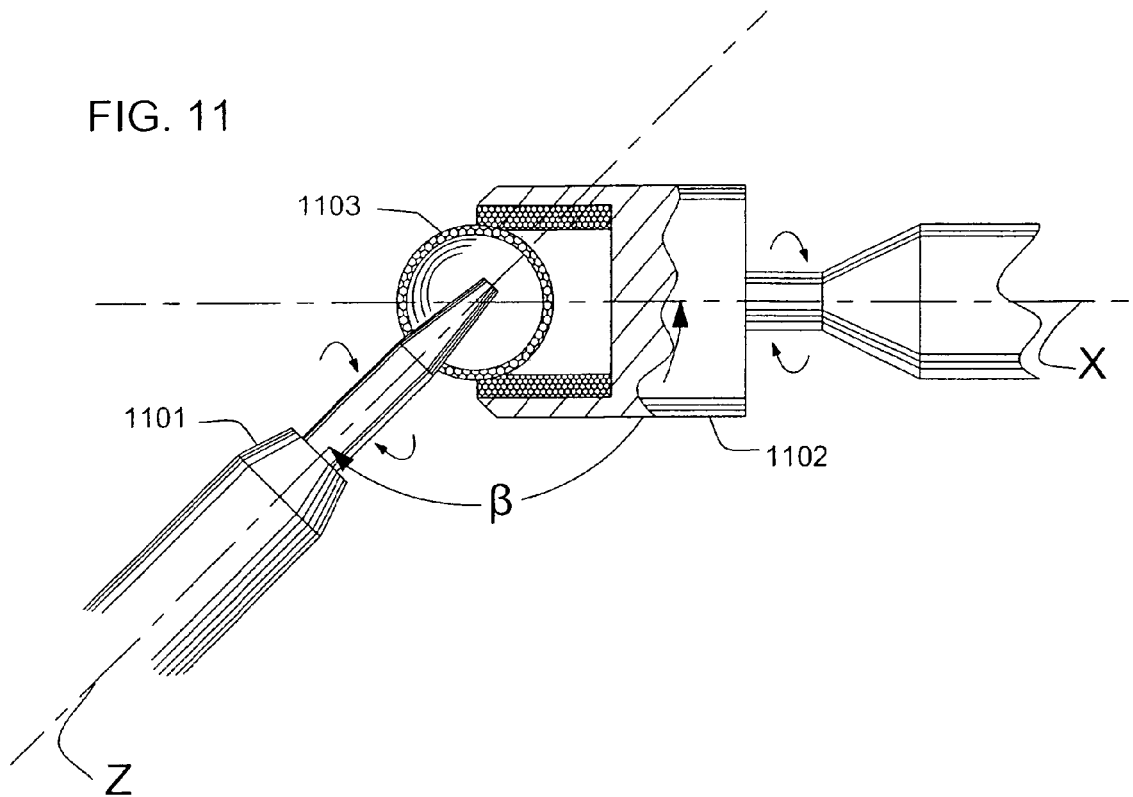
FIG. 11 depicts grinding and polishing of a convex spherical part, such as a ball bearing.

Referring to FIG. 11, it can be seen that a rotator 1101 holds a part to be finished 1103, in this case a convex sphere, by use of a spindle. The rotator 1101 is rotated continuously about its longitudinal axis (the z axis). A grinding or polishing wheel 1102 is provided is rotated continuously about its longitudinal axis (the x axis). The moving part 1103 is contacted with the moving grinding or polishing wheel 1102. The angular orientation β of the rotator 1101 with respect to the grinding or polishing wheel 1102 may be adjusted and oscillated to effect grinding or polishing of the part (ball or socket) across its entire surface and to maintain sphericity.

Figure 12:
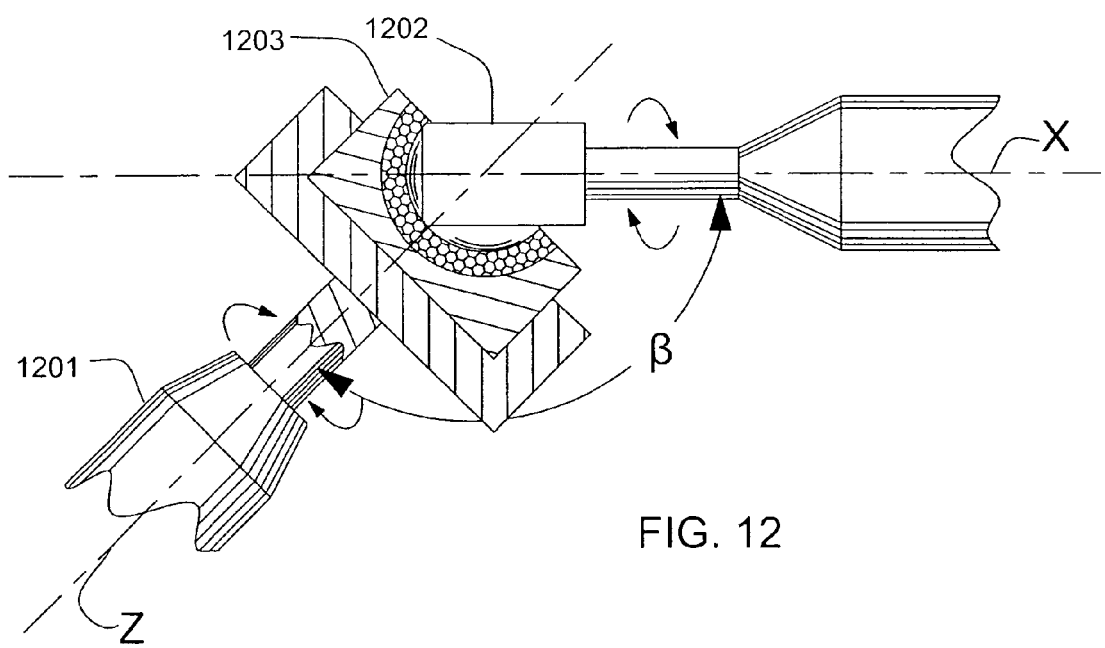
FIG. 12 depicts grinding and polishing of a concave spherical part, such as a race or a portion thereof.

Referring to FIG. 12, it can be seen that a rotator 1201 holds a part to be finished 1203, in this case a convex spherical cup or race, by use of the spindle. The rotator 1201 is rotated continuously about its longitudinal axis (the z axis). A grinding or polishing wheel 1202 is provided that is continuously rotatable about its longitudinal axis (the x axis). The moving part 1203 is contacted with the moving grinding or polishing wheel 1202. The angular orientation β of the rotator 1201 with respect to the grinding or polishing wheel 1202 may be adjusted and oscillated if required to effect grinding or polishing of the part across the spherical portion of it surface.

In the preferred embodiment of the invention, grinding utilizes a grit size ranging from 100 to 150 according to standard ANSI B74.16-1971 and polishing utilizes a grit size ranging from 240 to 1500, although grit size may be selected according to the user's preference. Wheel speed for grinding should be adjusted by the user to achieve a favorable material removal rate, depending on grit size and the material being ground. A small amount of experimentation can be used to determine appropriate wheel speed for grinding.

As desired in the invention, a diamond abrasive hollow grill may be used for polishing diamond or superhard bearing surfaces. A diamond abrasive hollow grill includes a hollow tube with a diamond matrix of metal, ceramic and resin (polymer) is found.

If a diamond surface is being polished, then the wheel speed for polishing preferably will be adjusted to cause a temperature increase or heat buildup on the diamond surface. This heat buildup will cause burnishing of the diamond crystals to create a very smooth and mirror-like low friction surface. Actual material removal during polishing of diamond is not as important as removal sub-micron sized asperities in the surface by a high temperature burnishing action of diamond particles rubbing against each other. A surface speed of 6000 feet per minute minimum is generally required together with a high degree of pressure to carry out burnishing. Surface speeds of 4000 to 10,000 feet per minute are believed to be the most desirable range.

Depending on pressure applied to the diamond being polished, polishing may be carried out at from about 500 linear feet per minute and 20,000 linear feet per minute.

Pressure must be applied to the workpiece in order to raise the temperature of the part being polished and thus to achieve the most desired mirror-like polish, but temperature should not be increased to the point that it causes complete degradation of the resin bond that holds the diamond polishing wheel matrix together, or resin will be deposited on the diamond. Excessive heat will also unnecessarily degrade the surface of the diamond.

Maintaining a constant flow of coolant (such as water) across the diamond surface being polished, maintaining an appropriate wheel speed such as 6000 linear feet per minute, applying sufficient pressure against the diamond to cause heat buildup but not so much as to degrade the wheel or damage the diamond, and timing the polishing appropriately are all important and must all be determined and adjusted according to the particular equipment being used and the particular part being polished. Generally the surface temperature of the diamond being polished should not be permitted to rise above 800 degrees Celsius or excessive degradation of the diamond will occur. Desirable surface finishing of the diamond, called burnishing, generally occurs between 650 and 750 degrees Celsius.

During polishing it is important to achieve a surface finish that has the lowest possible coefficient of friction, thereby providing a low friction and long-lasting articulation surface. Preferably, once a diamond or other superhard surface is formed in a bearing component, the surface is then polished to an Ra value of 0.3 to 0.005 microns. Acceptable polishing will include an Ra value in the range of 0.5 to 0.005 microns or less. The parts of the bearing component may be polished individually before assembly or as a unit after assembly. Other methods of polishing polycrystalline diamond compacts and other superhard materials could be adapted to work with the articulation surfaces of the invented bearing components, with the objective being to achieve a smooth surface, preferably with an Ra value of 0.01-0.005 microns.

Figure 13:
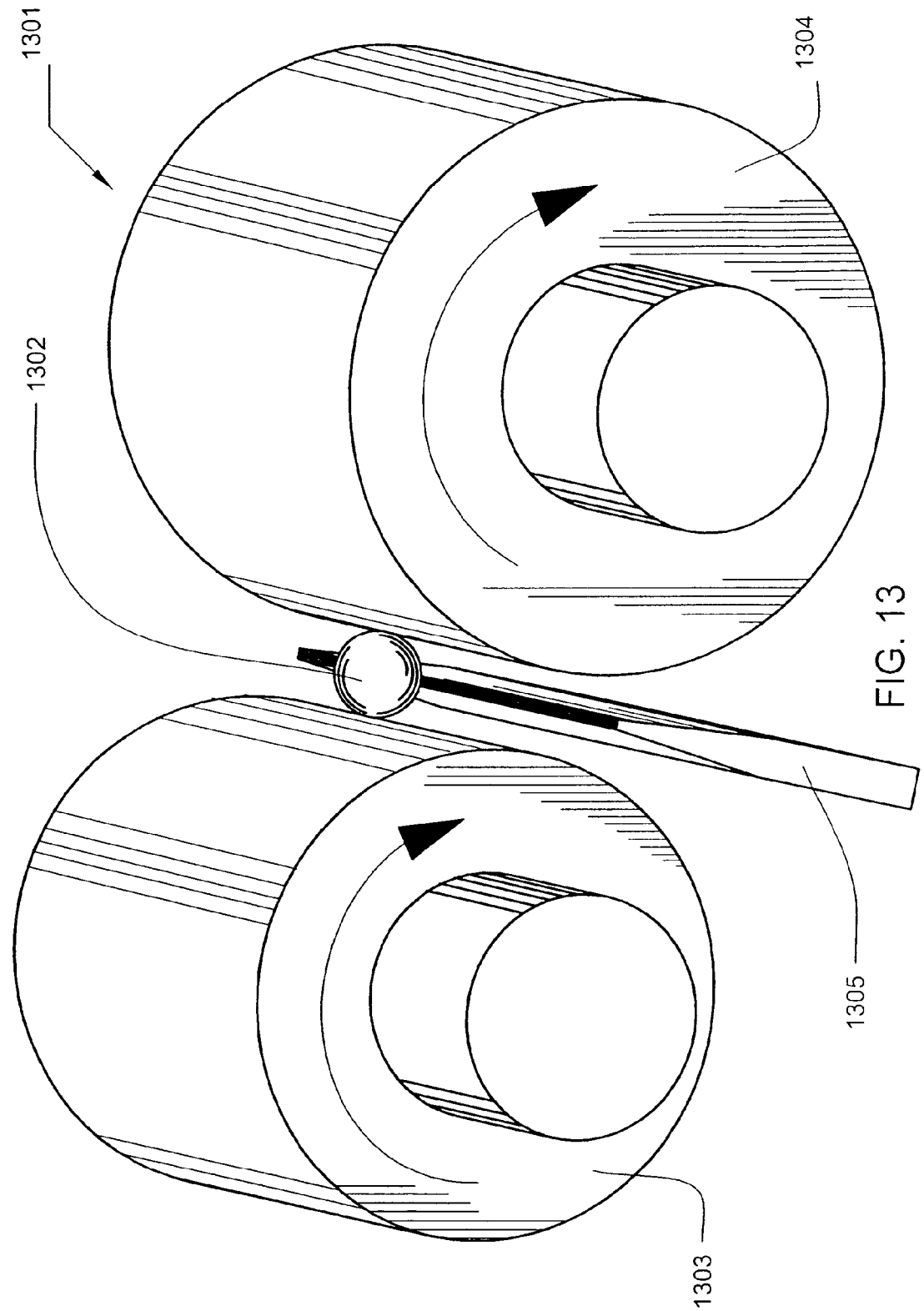
FIG. 13 depicts a diamond bearing being ground to spherical form and dimensions using a centerless grinding machine.

Referring to FIG. 13, a polycrystalline diamond compact bearing 1302 is being ground to spherical form and dimensions using a centerless grinding machine 1301. The bearing 1302 rests on a support rail 1305 and is kept in contact with a rotating diamond grinding wheel 1303 by a rubber composite regulating wheel 1304. The rotational motion of the grinding wheel 1303 and the regulating wheel 1304 cause the bearing 1302 to rotate against the surface of the grinding wheel 1303. The regulating wheel 1304, having a large frictional component because of its soft plastic surface, rotates the ball 1302 at high velocity and causes the ball 1302 to be pressed against the diamond grinding wheel 1303 with considerable pressure and thus effects removal of material from the surface of ball 1302 by abrasion. The small tangential contact point between the diamond grinding wheel 1303 and the ball 1302 causes high points on the ball 1302 to grind readily, and as the ball 1302 moves back and forth along the rail 1305, crossing paths are ground on the surface of the ball 1302. The feed rate of the regulating wheel 1304 toward the diamond grinding wheel 1303 determines the width of the ground path on the surface of the diamond ball 1302. High rates of feeding, such as 0.001 inch per minute generates a much wider path than a slower rate such as 0.0001 inch per minute. Therefore, roughing rates may vary from 0.0001 to 0.0040 and finishing rates from 0.00003 to 0.0005 inch per minute, or as otherwise selected by the user. The regulating wheel 1304 and the diamond grinding wheel 1303 may be modified with spiral grooves to facilitate the horizontal movement and rotation of the ball 1302 along the rail 1305. Those familiar with the art of centerless grinding can readily appreciate the various methodologies, machine settings and grinding wheel types useful for grinding diamond balls.

Structures manufactured according to the principles of the invention set forth above will provide strong and durable low friction bearing surfaces for a variety of uses including bearing components.

While the present invention has been described and illustrated in conjunction with a number of specific embodiments, those skilled in the art will appreciate that variations and modifications may be made without departing from the principles of the invention as illustrated herein and as claimed. The present invention may be embodied in other specific forms without departing from its spirit or essential characteristics. The described embodiments are to be considered in all respects as only illustrative, and not restrictive. The scope of the invention is, therefore, indicated by the appended claims, rather than by the foregoing description. All changes that come within the meaning and range of equivalency of the claims are to be embraced within their scope.

We claim:

1. A bearing comprising:
   a race having an articulation surface;
   a plurality of roller elements, each roller element having an articulation surface;
   wherein the plurality of roller elements are configured for rolling across the articulation surface of said race; and
   wherein at least one of said race and said roller elements comprises a sintered compact of superhard material forming the articulation surface thereof.

2. A bearing as recited in claim 1, wherein at least one of the race and the plurality of roller elements is formed from a continuous phase of polycrystalline diamond.

3. A bearing as recited in claim 1, further comprising a second race configured for rolling engagement with said plurality of roller bearing elements.

4. A bearing as recited in claim 3 wherein the second race articulation surface comprises sintered polycrystalline diamond.

5. A bearing as recited in claim 1, wherein the race and the plurality of roller elements comprise sintered polycrystalline diamond.

6. A bearing comprising:
   a first race, the first race having an articulation surface which comprises a sintered compact of superhard material selected from the group consisting of diamond and boron nitride; and
   a plurality of bearing roller elements, each of the plurality of bearing roller elements comprising an articulation surface which comprises a sintered compact of superhard material selected from the group consisting of diamond and boron nitride, and wherein the bearing roller elements roll across the first race articulation surface.

7. The bearing of claim 6, wherein the first race comprises a compact having a substrate and having the superhard material bonded to the surface of the substrate.

8. The bearing of claim 7, wherein only a portion of the race articulation surface is covered with the superhard material.

9. The bearing of claim 6, wherein the each of the plurality of bearing roller elements comprise a compact having a substrate and having the superhard material bonded to the surface of the substrate.

10. The bearing of claim 9, wherein only a portion of the bearing roller element articulation surface is covered with superhard material.

11. The bearing of claim 6, wherein each of the bearing roller elements has a circular cross section.

12. The bearing of claim 6, wherein each of the bearing roller elements is spherical.

13. The bearing of claim 6, further comprising a second race, the second race having an articulation surface which comprises a sintered compact of superhard material selected from the group consisting of diamond and boron nitride, and wherein the plurality of bearing roller elements roll across the second race articulation surface.

14. The bearing of claim 13, wherein the first race and the second race are disposed about a common axis of rotation such that the first race articulation surface faces towards the second race articulation surface and such that the plurality of bearing roller elements are disposed therebetween, and wherein each of the plurality of bearing roller element is in contact with the first race articulation surface and the second race articulation surface.

15. The bearing of claim 14, wherein the first race is rotatable about the common axis relative to the second race, and wherein the plurality of bearing roller elements roll between the first race and second race.

16. A bearing comprising:
   a plurality of bearing roller elements, each of the plurality of bearing roller elements comprising an articulation surface which is formed from a sintered compact of superhard material selected from the group consisting of diamond and boron nitride;
   a first race, the first race comprising a first circular articulation surface which is formed from a sintered compact of superhard material selected from the group consisting of diamond and boron nitride; and
   a second race, the second race comprising a second circular articulation surface which is formed from a sintered compact of superhard material selected from the group consisting of diamond and boron nitride; and
   wherein the first race and second race are disposed about a common rotational axis and wherein the plurality of bearing roller elements are disposed between the first circular articulation surface and the second circular articulation surface and in contact with the first circular articulation surface and second circular articulation surface, and wherein the plurality of bearing roller elements roll across the first circular articulation surface and the second circular articulation surface to facilitate the rotation of the first race relative to the second race.

17. The bearing of claim 16, wherein the first circular articulation surface and second circular articulation surface comprises a continuous layer of superhard material.

18. The bearing of claim 16, wherein the first circular articulation surface comprises segmented superhard material.

19. The bearing of claim 16, wherein the first race comprises a compact having a substrate and having the superhard material attached to the surface of the substrate.

20. The bearing of claim 19, wherein the substrate comprises metal, metal carbides, and mixtures thereof.

21. The bearing of claim 16, wherein the superhard material comprises bonded particles of superhard material and metal located between said particles of superhard material.

* * * * *